US007582222B2

(12) United States Patent
Punnoose

(10) Patent No.: US 7,582,222 B2
(45) Date of Patent: Sep. 1, 2009

(54) TRANSITION METAL-DOPED OXIDE SEMICONDUCTOR EXHIBITING ROOM-TEMPERATURE FERROMAGNETISM

(75) Inventor: Alex Punnoose, Boise, ID (US)

(73) Assignee: Boise State University, Boise, ID (US)

( * ) Notice: Subject to any disclaimer, the term of this patent is extended or adjusted under 35 U.S.C. 154(b) by 733 days.

(21) Appl. No.: 11/195,573

(22) Filed: Aug. 1, 2005

(65) Prior Publication Data

US 2006/0060815 A1    Mar. 23, 2006

Related U.S. Application Data

(60) Provisional application No. 60/612,708, filed on Sep. 23, 2004, provisional application No. 60/598,203, filed on Jul. 30, 2004.

(51) Int. Cl.
    *C09D 5/23* (2006.01)
(52) U.S. Cl. .................. 252/62.51 R; 252/520.1; 423/594.9; 423/594.5; 977/773; 977/811
(58) Field of Classification Search .............. 252/62.56, 252/62.51 R, 518.1; 423/592.1, 594.9; 977/773, 977/776
    See application file for complete search history.

(56) References Cited

U.S. PATENT DOCUMENTS

| | | | |
|---|---|---|---|
| 4,731,226 A | 3/1988 | Takahata et al. | 422/98 |
| 4,935,383 A | 6/1990 | Nouhi et al. | 437/81 |
| 4,957,615 A | 9/1990 | Ushizawa et al. | 204/415 |
| 5,296,048 A | 3/1994 | Chang et al. | 148/33 |
| 5,756,207 A | 5/1998 | Clough et al. | 428/375 |
| 5,788,887 A | 8/1998 | Swanson | 252/520.1 |
| 5,788,913 A | 8/1998 | Swanson | 525/520.1 |
| 6,132,524 A | 10/2000 | Akinaga et al. | 148/315 |
| 6,610,421 B2 | 8/2003 | Akinaga et al. | 428/642 |

OTHER PUBLICATIONS

Fitzgerald et al, "SnO2 doped with Mn, Fe or Co: Room temperature dilute magnetic semiconductors," J. Applied Physics, 2004, 95(11) pp. 7390-7392.*

D.H. Kim, et al. "Investigations on the nature of observed ferromagnetism and possible spin polarization on Co-doped anatase $TiO_2$ thin films", Journal of Applied Physics, vol. 93, No. 10, May 15, 2003, pp. 6125-6132.

S.B. Ogale, et al. "High Temperature Ferromagnetism with a Giant Magnetic Mount in Transport Co-doped $SnO_{2-6}$" Physical Review Letters, vol. 91, No. 7, week ending Aug. 15, 2003, pp. 077205-1 thru 077205-3.

J.M.D. Coey, et al. "Ferromagnetism in Fe-doped $SnO_2$ thin films", Applied Physics Letter, vol. 84, No. 8, Feb. 23, 2004, pp. 132-1334.

* cited by examiner

*Primary Examiner*—Stanley Silverman
*Assistant Examiner*—Kallambella Vjayakumar
(74) *Attorney, Agent, or Firm*—Pedersen & Co., PLLC; Ken J. Pedersen; Barbara S. Pedersen

(57) ABSTRACT

An oxide semiconductor doped with a transition metal and exhibiting room-temperature ferromagnetism is disclosed. The transition metal-doped oxide semiconductor is preferably manufactured in powder form, and the transition metal is preferably evenly distributed throughout the oxide semiconductor. The preferred embodiments are iron-doped tin dioxide and cobalt-doped tin dioxide. Gases may be detected by passing them across a material and measuring the change in magnetic properties of the material; the preferred material is iron-doped tin dioxide.

33 Claims, 35 Drawing Sheets

TRANSITION METAL-DOPED OXIDE SEMICONDUCTOR EXHIBITING ROOM-TEMPERATURE FERROMAGNETISM

This application claims priority based on U.S. Provisional Application No. 60/598,203, Ferromagnetic Powders of Tin Oxide Nanoparticles Doped with Cobalt and Magnetic Gas Sensor Utilizing Them, filed Jul. 30, 2004, and U.S. Provisional Application No. 60/612,708, Development of High Temperature Ferromagnetism in $SnO_2$ and Paramagnetism in SnO by Fe Doping, filed Sep. 23, 2004, the disclosures of both of which are hereby incorporated by reference.

BACKGROUND OF THE INVENTION

1. Field of the Invention

The present invention relates to semiconductors exhibiting room-temperature ferromagnetism.

2. Related Art

Solid materials are either crystalline or amorphous. A crystalline solid is one in which the atomic arrangement is regularly repeated, and which is likely to exhibit an external morphology of planes making characteristic angles with each other. In many materials, there are actually a variety of solid phases, each corresponding to a unique crystal structure. These varying crystal phases of the same substance are called "allotropes" or "polymorphs". The mechanical, thermal, optical, electronic, and magnetic properties of crystals are strongly influenced by the periodic arrangement of their atomic cores. A nanoscale particle is a particle having a measurement of 100 nm or less in at least one direction.

A crystal may be regarded as a three-dimensional diffraction grating for energetic electromagnetic waves (typically X-rays) of a wavelength comparable with the atomic spacing; the diffraction pattern will provide information about the periodic arrangements of the atoms. Constructive interference of the electromagnetic waves may occur where the following minimum condition (called the Bragg equation) is satisfied:

$$2d \sin \theta = n\lambda$$

where d is the spacing between crystalline planes, $\theta$ is the angle of incidence between the beam of X-rays and the parallel crystalline planes, n is an integer, and $\lambda$ is the wavelength of the X-rays. This equation will not be satisfied for most angles $\theta$; to investigate crystals of unknown orientation, the rotating crystal method is used, wherein $\theta$ is varied as a function of time while X-rays of a single wavelength are presented to a single crystal. A cylinder of photographic film records a spot whenever the Bragg condition is fulfilled.

In the Debye-Scherrer technique, instead of using a single X-ray wavelength and a time-dependent angle of incidence, a crystalline sample is presented with every $\theta$ simultaneously. This is achieved by using a finely powdered crystalline sample in which the crystalline orientations are random. Rays for which one crystallite or another satisfy the Bragg condition emerge from the sample as a series of cones concentric with the incident beam direction. Thus a photographic plate records a series of concentric circles. The spacing and pattern of these circles is used to determine the atomic structure of the crystal.

Particle-induced x-ray emission (PIXE) is an analytical technique capable of trace element detection sensitivity of a few parts per million. When ions pass through matter, they interact with the electrons in the atoms and occasionally a vacancy is produced by an excited electron. When this occurs in an inner shell, the vacancy is filled by an electron from an outer shell, and an x-ray photon of characteristic energy is emitted. By measuring the energy of the photon, one can determine the atomic number of the element and the amount of the element present that can be extracted from the area under the x-ray peak. For identification and quantification of trace elements, PIXE is 100 times more sensitive than electron micro-analysis systems.

Mossbauer spectroscopy is a spectroscopic technique based on the Mossbauer effect. In its most common form, Mossbauer Absorption Spectroscopy, a solid sample is exposed to a beam of gamma radiation, and a detector measures the intensity of the beam that is transmitted through the sample. The gamma-ray energy is varied by accelerating the gamma-ray source through a range of velocities with a linear motor. The relative motion between the source and the sample results in an energy shift due to the Doppler effect. In the resulting spectra, gamma-ray intensity is plotted as a function of the source velocity. At velocities responding to the resonant energy levels of the sample, some of the gamma-rays are absorbed, resulting in a dip in the measured intensity and a corresponding dip in the spectrum. The number, positions, and intensities of the dips (also called peaks) provide information about the chemical environment of the absorbing nuclei and can be used to characterize the sample.

In x-ray photoelectron spectroscopy, the sample is illuminated with soft x-radiation in an ultrahigh vacuum. The photoelectric effect leads to the production of photoelectrons, the energy spectrum of which can be determined in a beta-ray spectrometer. The difference between the x-ray photon energy, which is known, and the electron energy, which can be measured, results in the binding energy of the orbital from which the electron was expelled. Measurement of the relative areas of the photoelectron peaks allows the composition of the sample to be determined.

In discussing magnetic fields, the relationship between the magnetic field intensity H and the corresponding magnetic induction B is $$B = \mu_0(H + M)$$
$$= \mu_0(1 + \chi_m)H = \mu_0\mu_m H = \mu H$$

where M is the magnetization, $\chi_m$ is the magnetic susceptibility, $\mu_m$ is the relative permeability, $\mu$ is the absolute permeability, and $\mu_0 = 4\pi \times 10^{-7}$ H/m is the permeability of free space.

The magnetic response of most solids is dominated by the orientation of permanent dipoles. The response of a magnetic material is usually expressed in terms of either the magnetization M or the magnetic susceptibility $\chi$, where $$M = \chi H$$

and $$\chi = M/H$$

A spinning charged particle constitutes a magnetic dipole. The magnetic dipole moment of an electron is attributed to its "spin," and creates a magnetic field pointing in a direction perpendicular to the plane in which the electron is spinning, as shown in FIG. 1.

There are four different kinds of magnetic behavior which involve permanent dipoles in a solid, namely paramagnetic, antiferromagnetic, ferromagnetic, and ferrimagnetic. The low temperature ordering, if any, of neighboring dipoles, and the consequent behavior of spontaneous magnetization and/or susceptibility results in hysteresis loops (shown in FIG. 3) in ferromagnetic and ferromagnetic materials.

Paramagnetic behavior, shown in FIG. 2(a), occurs when the magnetic moments of the various atoms are uncorrelated in the absence of a magnetic field, and the sum total of the magnetic moments tends toward zero. The dipoles do tend to become aligned in a magnetic field. The magnetic susceptibility follows the Curie Law:

$$\chi_m = C/T$$

where C is the Curie constant of the solid, and T represents the temperature of the solid.

Antiferromagnetic behavior, shown in FIG. 2(b), occurs when the dipoles, or magnetic moments, alternate, causing the sum total of the magnetic moments to tend toward zero. This arrangement is very stable at low temperatures, and the magnetic susceptibility in an applied field is small. When the temperature rises, the efficiency of this dipole-dipole interaction decreases and the magnetic susceptibility increases, until the spins become "free" at the Neel temperature to respond to a field. At even higher temperatures the behavior becomes paramagnetic, and the magnetic susceptibility follows a modified Curie law $$\chi_m = C/(T+\theta)$$

A ferromagnetic solid, represented in FIG. 2(c), is ordered with parallel spins below the Curie temperature $T_c$, which results in a spontaneous magnetization $M_s$. The magnitude of this bulk polarization decreases to zero at the Curie temperature $T_c$ (which is well below room-temperature in most ferromagnetic solids), and the paramagnetic susceptibility for the disordered spin system at higher temperatures obeys the Curie-Weiss law $$\chi_m = C/(T-T_c)$$

Ferromagnetism involves the cooperative alignment of permanent atomic dipoles, which arise in atoms having unpaired electrons. The strength of each individual dipole is small, but a completely ordered array of such moments produces a large spontaneous magnetization $M_s$.

The low temperature ordering in a ferrimagnetic material, as shown in FIG. 2(d), is similar to that of an antiferromagnetic material, but the two opposing spin systems have magnetic moments of unequal magnitude, and a net spontaneous magnetization results. This magnetization declines to zero magnitude when the solid is warmed to the Curie point $T_f$, and the behavior is once again paramagnetic at higher temperatures.

Hysteresis loops demonstrate a phenomenon wherein a material that did not show any magnetization before the application of a magnetic field exhibits remanent magnetization after the applied magnetic field is removed, as shown in FIG. 3. The coercivity $H_c$ is the value of the magnetic field that must be applied to return the magnetization to zero after the magnetization has been caused to reach its saturation value; the remanence $B_r$ ($M_r$ in the text below) is the value of the magnetization of the material after the material has been caused to reach its saturation value and then had the applied magnetic field removed. Non-zero values for the coercivity and remanence of a sample imply that the sample is ferromagnetic.

Oxide semiconductors have been used to detect gases. However, these have all been non-magnetic oxide semiconductors. Their electrical and semiconducting properties (determined by electrical resistivity, carrier concentration, and carrier mobility) vary with oxygen stoichiometry. Oxygen stoichiometry can be changed by passing a reducing or oxidizing gas. Thus, traditionally, monitoring the changes in the electrical properties with the type and flow rates of gases has been used as a sensing method.

Tin Dioxide, $SnO_2$, is an oxide semiconductor with a wide band gap of ~3.6 eV. When prepared with oxygen vacancies, $SnO_2$ becomes an n-type semiconductor. When doped with iron (Fe) or cobalt (Co), $SnO_2$ remains an n-type semiconductor. Development of room-temperature ferromagnetism (RTFM) in conventional semiconductors is currently attracting intense interest due to their potential use in spintronics applications. However, most traditional transition metal-doped magnetic semiconductor systems exhibit ferromagnetism only at temperatures that are well below room temperature.

SUMMARY OF THE INVENTION

The present invention is a transition metal-doped semiconductor exhibiting room-temperature ferromagnetism. Preferably, it is manufactured in nanoscale particle form; it also preferably exhibits room-temperature ferromagnetism. The preferred embodiments are iron-doped tin dioxide and cobalt-doped tin dioxide, with the dopant evenly distributed throughout the lattice.

DESCRIPTION OF THE PREFERRED EMBODIMENTS

Figure 1:
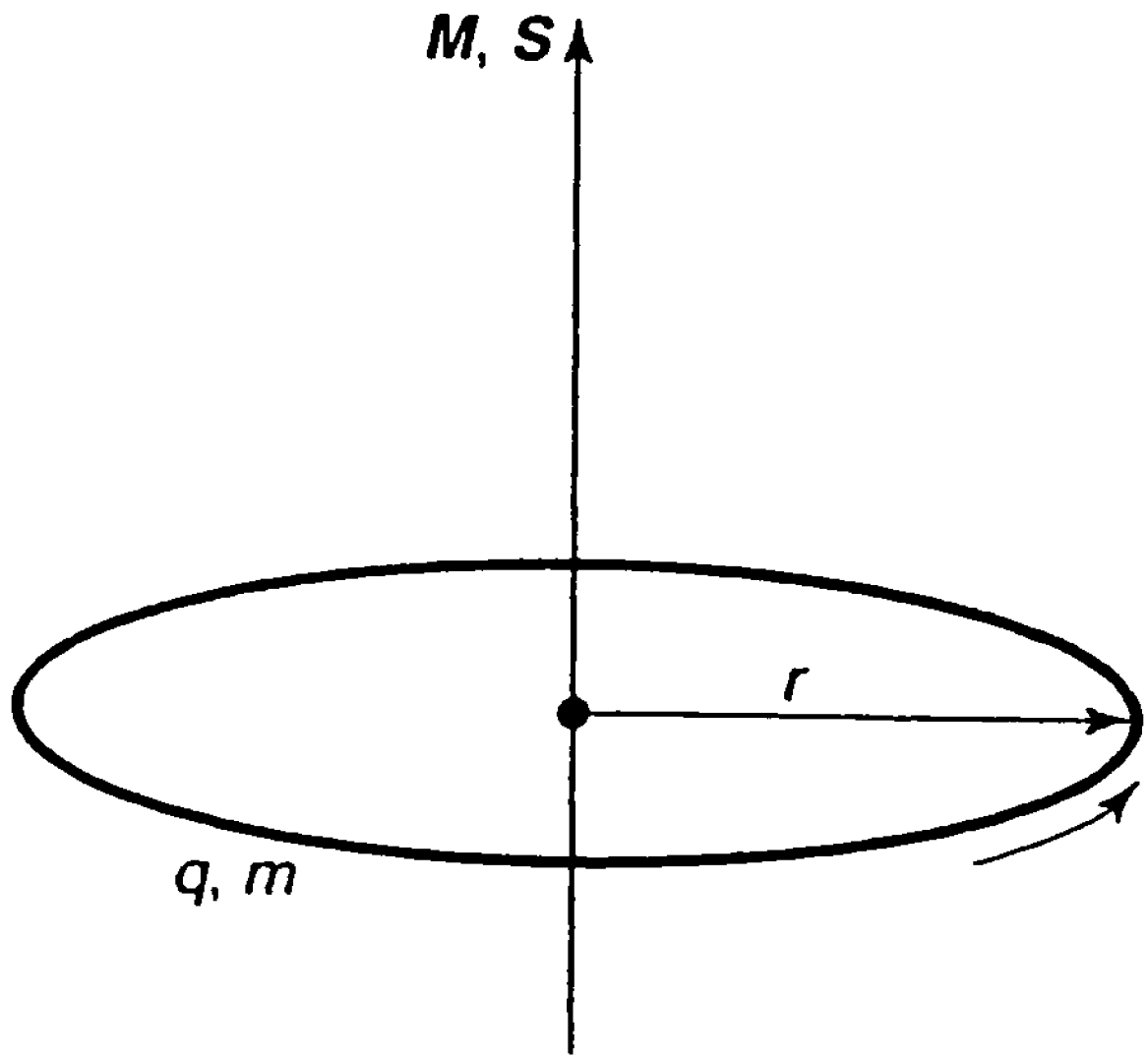
FIG. 1 shows a ring of charge rotating about its axis.
Figure 2:
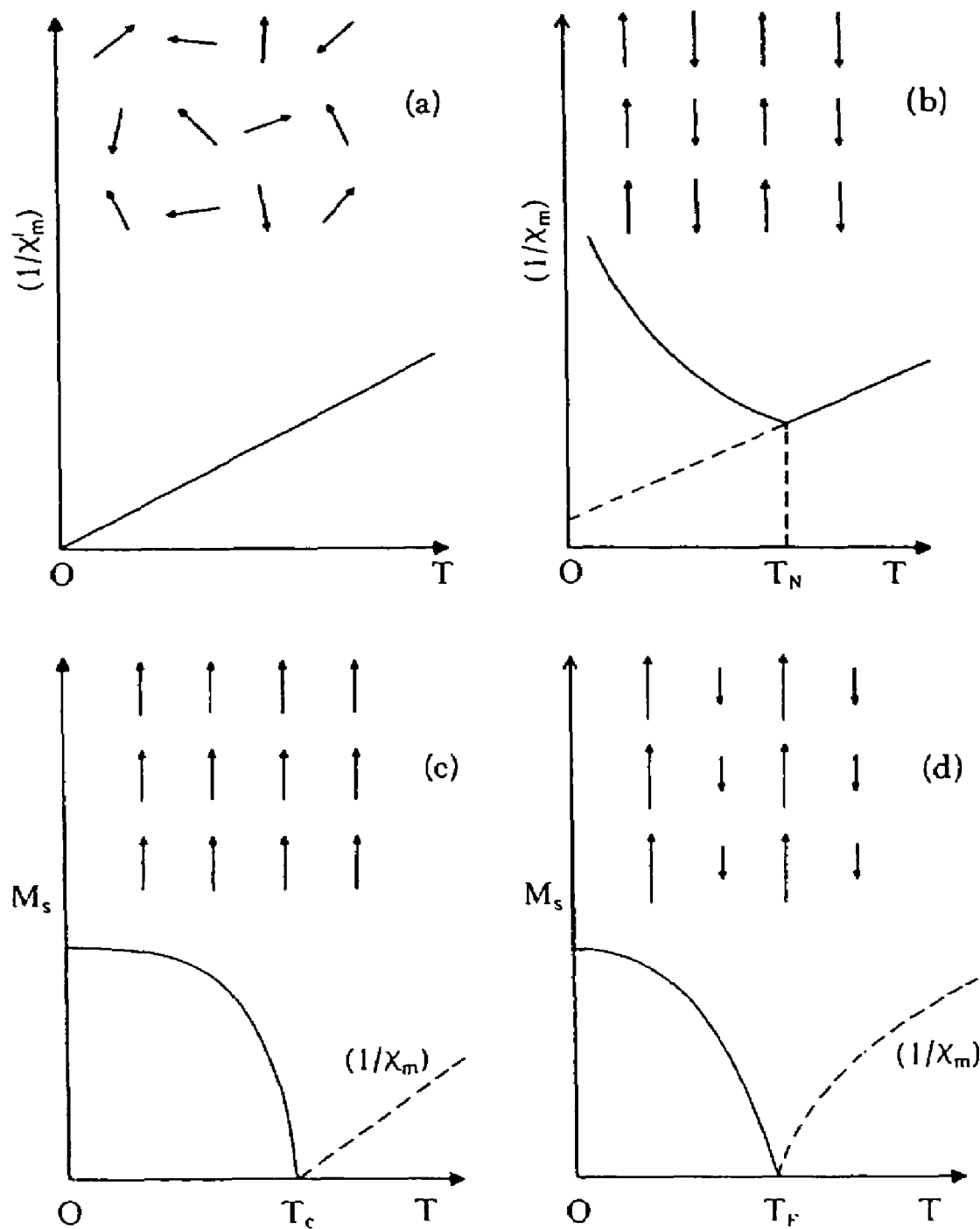
FIG. 2 shows the low temperature ordering, if any, of neighboring dipoles, and the consequent behavior of spontaneous magnetism and/or susceptibility, for (a), paramagnetism, (b) antiferromagnetism, (c) ferromagnetism, and (d) ferrimagnetism.
Figure 3:
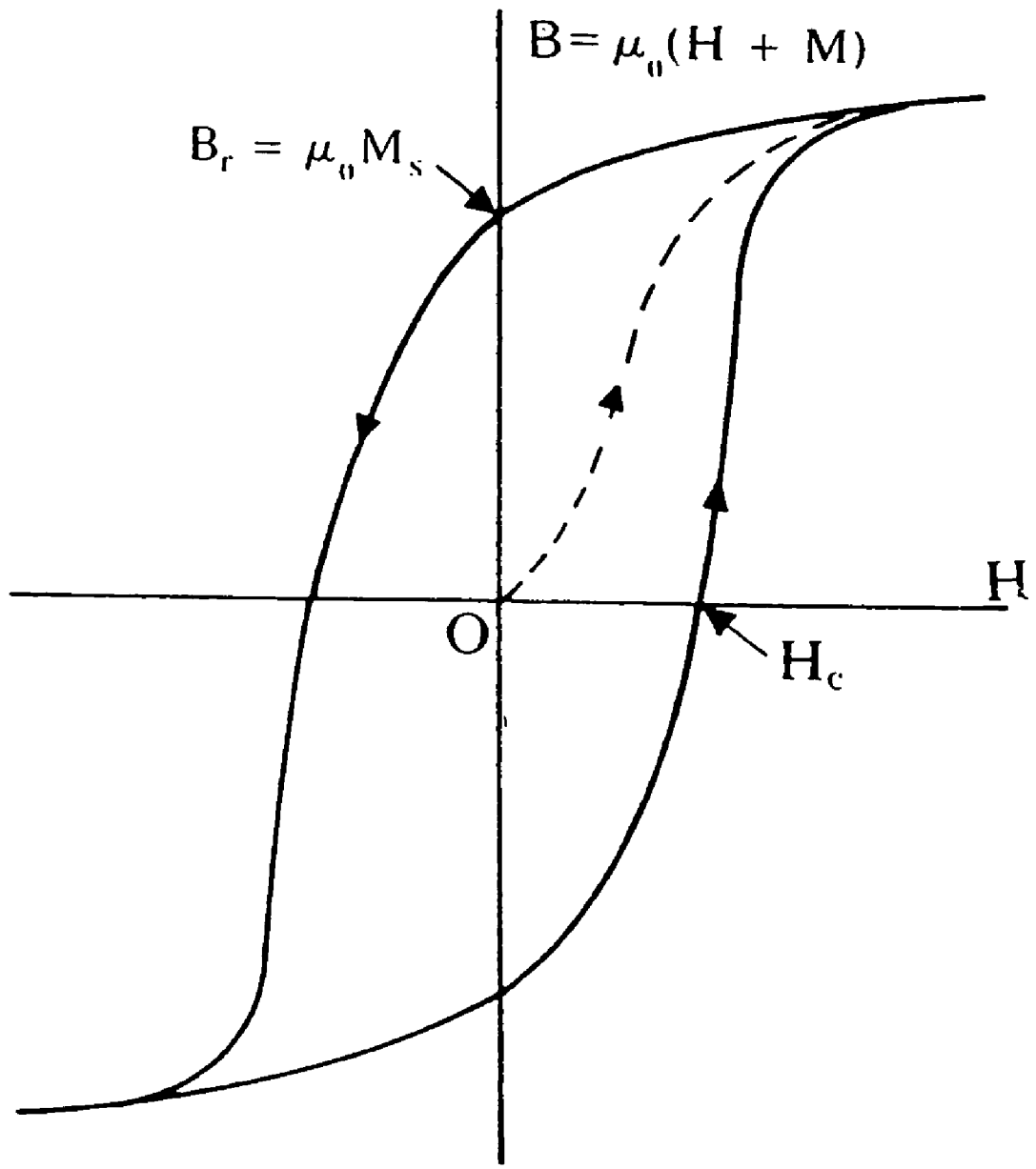
FIG. 3 shows a schematic magnetization loop for a multi-domain sample of a ferromagnetic solid. $H_c$ is the coercivity, and $B_r$ is the remanence of the sample. The dashed curve shows what happens when a nonmagnetized sample is first magnetized. The arrows on the solid curves show the course of a subsequent hysteresis loop.

I. The Materials Used in the Gas Sensing Process

The preferred embodiment is a powder comprising an oxide semiconductor that is transition-metal doped; preferably, the semiconductor is $SnO_2$. Impurities from other elements could be present and not significantly affect the magnetic properties of the composition. The invention does not have to be in powder form, as the composition manufactured by the preferred process can be converted into other forms, such as films. In the preferred embodiment, the transition metal is iron (Fe), the doping concentration is between 0.5% and 10%, the Curie temperatures is as high as 850K, the composition takes on a powder form with nanoscale particles of which 95% are believed to be less than 100 nm in length, there are no phases, or clusters of Fe, in the composition, meaning that the Fe is evenly distributed throughout the composition, and the composition is intrinsically ferromagnetic, meaning that the Fe atoms take the place of the Sn atoms in the lattice, and are substitutionally incorporated into the $SnO_2$ lattice at the Sn sites. Preparation conditions have a strong effect on the observed magnetic properties and might act as a useful control parameter.

The preferred embodiment, $Sn_{1-x}Fe_xO_2$, is manufactured by the following preferred process, which is less expensive than other methods of manufacturing ferromagnetic oxide semiconductors. Appropriate amounts of tin dichloride ($SnCl_2$) of minimum 99% purity, iron dichloride ($FeCl_2$) of minimum 99.5% purity, and $NH_4OH$ are added to de-ionized water to produce solutions with molarities of 1, 0.02, and 5M, respectively. All the samples are prepared by reacting the 0.02M $FeCl_2$ and 1 M $SnCl_2$ solutions at 80° C. {molar ratio of x=[Fe]/([Fe]+[Sn])} with a large amount (~1.5 times the precursor solution volume) of a 5M solution of $NH_4OH$. The resulting precipitate is washed to remove any water-soluble byproducts and annealed in air for three hours at 600° C. to obtain powder samples of $Sn_{1-x}Fe_xO_2$; in the case of the ratios of 0.02 M $FeCl_2$ and 1 M $SnCl_2$ in one embodiment, $Sn_{0.98}Fe_{0.02}O_2$ is obtained. Samples of $Sn_{0.95}Fe_{0.05}O_2$ have also been prepared by annealing the same precipitate at temperatures of 350, 450, 750, and 900° C. for the purpose of investigating the effect of the annealing temperature. When the precipitate is annealed at 200° C., iron-doped tin monoxide ($Sn_{1-x}Fe_xO$) results. Pure iron oxide samples have been prepared following identical synthesis procedures without using any $SnCl_2$ to obtain insight into possible Fe impurity phases that might form under these synthesis conditions.

In an alternative embodiment, cobalt-doped tin dioxide, $Sn_{1-x}Co_xO_2$, with x being 1% or less, exhibiting room-temperature ferromagnetism, has been developed. In this alternative embodiment, magnetic hysteresis loops are observed at 300 K (room-temperature) with coercivity $H_c$ ~630 Oe, saturation magnetization $M_s$ ~0.233 $\mu_B$/Co ion and about 31% remenance. $SnO_2$ samples doped with ≦1% Co showed RTFM with significantly high coercivity (~630 Oe), moderate remenance (~31%) and better squareness of the hysteresis loop, but had a lower magnetic moment of 0.133 $\mu_B$/Co ion. However, for x>0.01, this ferromagnetism was completely destroyed and the samples demonstrated paramagnetic behavior. Preferably, the Co is evenly distributed throughout the $SnO_2$ lattice, and the composite takes on a nanoscale particle form.

The $Sn_{1-x}Co_xO_2$ is preferably prepared using a wet chemical method by reacting 0.02 M $CoCl_2 \cdot 6H_2O$ and 1 M $SnCl_2$ with a molar ratio of x=[Co/(Co+Sn)]. A few drops of concentrated HCl are added to ensure dissolution. This solution is added to a 5M solution of $NH_4OH$, and the resulting mixture is heated to 80° C. for several hours. The precipitate is annealed in air at various temperatures for three hours to obtain $Sn_{1-x}Co_xO_2$. Chemically synthesized $Sn_{1-x}Co_xO_2$ powders have been shown to exhibit RTFM for x≦0.01 when prepared in the 350 to 600° C. range.

The sol-gel based wet chemistry used to manufacture the two preferred embodiments is preferred over other possible means because it is relatively inexpensive, it intrinsically excludes the segregation of transition metal nanoparticles, it has the ability to kinetically stabilize metastable phases (such as orthorhombic $SnO_2$) and extended solid solutions, and it is very efficient for the controlled syntheses of materials in the nanosize range.

For both Fe- and Co-doped $SnO_2$ with preparation temperatures of <300° C. and >750° C., there is no ferromagnetism and the particles are not nanoscale in size. It is believed that a ferromagnetic powder with nanoscale particles can be achieved with an annealing temperature above 300° C. and below 750° C.

A. Confirmation of Nominal Doping Concentrations

The nominal Fe doping concentrations of both $Sn_{1-x}Fe_xO_2$ and $Sn_{1-x}Fe_xO$ have been confirmed by PIXE measurements. The powder samples were first mixed with a very small amount of polyvinyl alcohol and then palletized using a hand-held press. The samples were then irradiated with a 2.0 MeV He+ ion beam and the x-rays emitted during the de-excitation process within the atoms were analyzed using an x-ray spectrometer.

Figure 4:
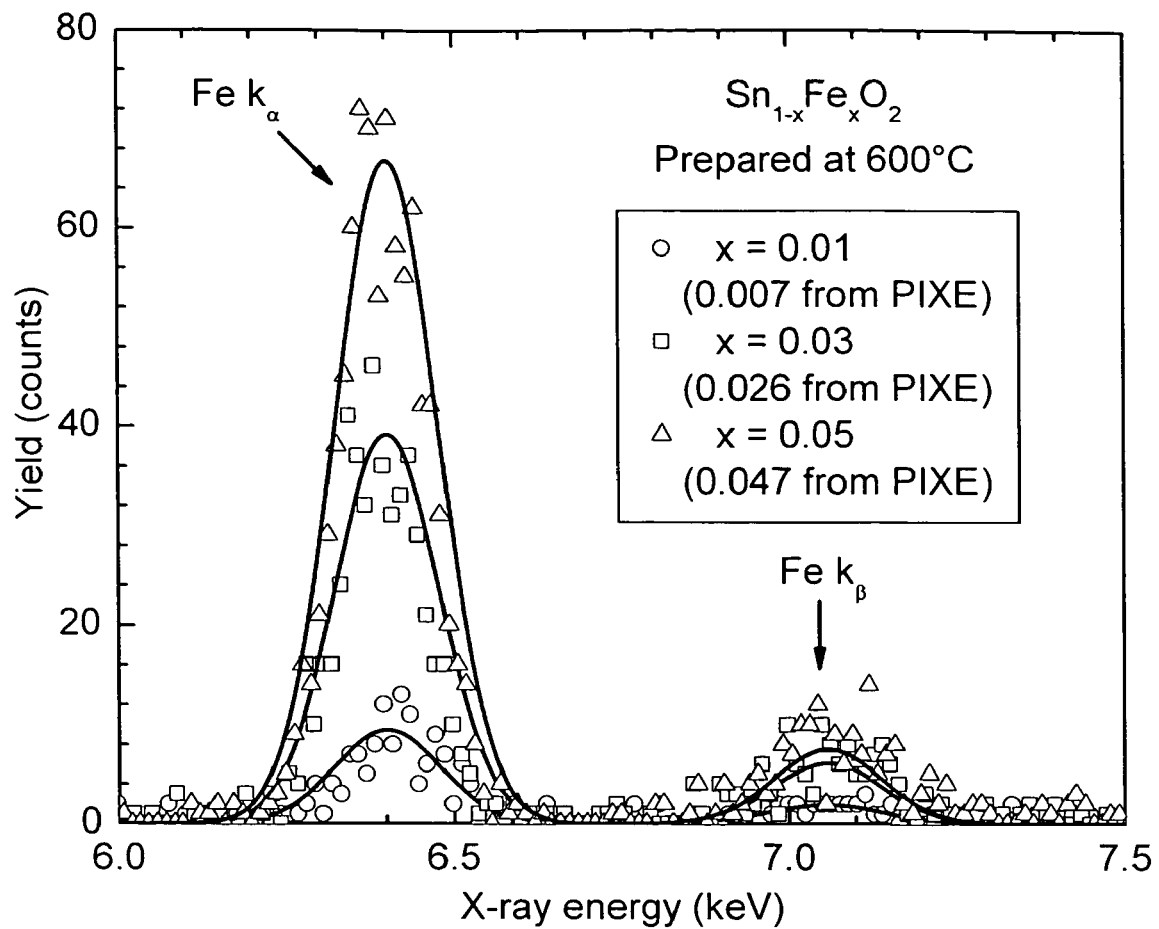
FIG. 4 shows typical PIXE spectra from the $Sn_{1-x}Fe_xO_2$ samples showing the Fe region. Fe concentrations (x) obtained by PIXE data simulation (solid lines) are given in parentheses.

The PIXE data obtained from selected samples of $Sn_{1-x}Fe_xO_2$ are shown in FIG. 4. The Fe concentrations shown in Table I, estimated by simulating the experimental PIXE spectra after removing the background due to bremsstrahlung, are in reasonable agreement with their nominal concentrations. This confirms that the ratio of Fe to Sn in the resulting product is substantially the same as the ratio of the $FeCl_2$ and $SnCl_2$ solutions that were reacted with $NH_4OH$.

The directly opposite changes in the lattice parameters observed in $Sn_{1-x}Fe_xO_2$ and $Sn_{1-x}Fe_xO$ with Fe doping concentration might reflect the effect of substituting $Fe^{3+}$ for $Sn^{4+}$ ions in $SnO_2$ and for $Sn^{2+}$ ions in SnO. This might require rearrangement of neighboring oxygen ions for charge neutrality.

When the 5% Fe-doped $Sn_{1-x}Fe_xO_2$ samples were prepared at different temperatures in the 200 to 900° C. range, the

TABLE I

Atomic concentration estimates of $Sn_{1-x}Fe_xO$ and $Sn_{1-x}Fe_xO_2$ obtained from PIXE and XPS measurements.

| Nominal Fe % | Fe % from PIXE | Preparation temperature (° C.) | Major XRD identified phase | Processing conditions | Estimated atomic % from XPS | | |
|---|---|---|---|---|---|---|---|
| | | | | | Fe | Sn | O |
| 0 | — | 200 | $Sn_{1-x}Fe_xO$ | As-prepared | — | 29.2 | 55.4 |
| 1 | 0.79 | 200 | $Sn_{1-x}Fe_xO$ | As-prepared | — | 30.1 | 61.0 |
| 3 | 3.07 | 200 | $Sn_{1-x}Fe_xO$ | As-prepared | — | — | — |
| 5 | 4.54 | 200 | $Sn_{1-x}Fe_xO$ | As-prepared | 1.2 | 29.2 | 61.0 |
| 0 | — | 600 | $Sn_{1-x}Fe_xO_2$ | As-prepared | — | 31.2 | 61.2 |
| 1 | 0.66 | 600 | $Sn_{1-x}Fe_xO_2$ | As-prepared | — | 31.7 | 62.2 |
| 3 | 2.66 | 600 | $Sn_{1-x}Fe_xO_2$ | As-prepared | — | — | — |
| 5 | 4.888 | 600 | $Sn_{1-x}Fe_xO_2$ | As-prepared | 3.1 | 27.7 | 59.7 |
| 5 | — | 350 | $Sn_{1-x}Fe_xO_2$ | As-prepared | 0.7 | 30.0 | 60.2 |
| 5 | — | 450 | $Sn_{1-x}Fe_xO_2$ | As-prepared | 1.1 | 31.8 | 64.2 |
| 5 | — | 750 | $Sn_{1-x}Fe_xO_2$ | As-prepared | 3.9 | 28.6 | 62.3 |
| 5 | 4.00 | 900 | $Sn_{1-x}Fe_xO_2$ | As-prepared | 6.2 | 23.1 | 56.3 |
| 5 | — | 900 | $Sn_{1-x}Fe_xO_2$ | 10 nm $Ar^+$ ion sputtered | 4.5 | 36.3 | 57.5 |
| 5 | — | 900 | $Sn_{1-x}Fe_xO_2$ | 20 nm $Ar^+$ ion sputtered | 3.4 | 39.7 | 56.2 |

Figures 5A, 5B, 5C, 5D, 5E, 5F:
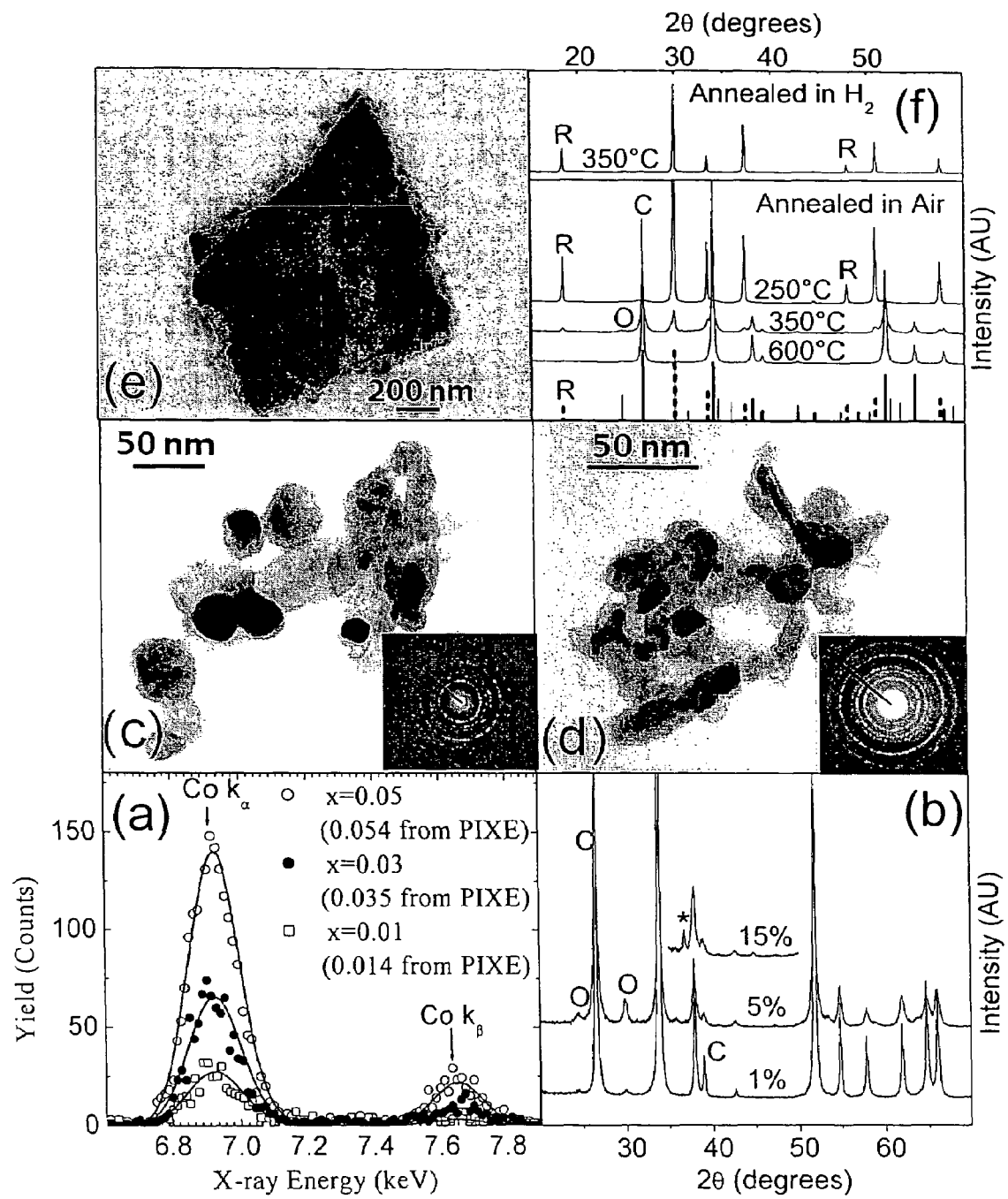
FIG. 5 shows (a) typical PIXE spectra from the $Sn_{1-x}Co_xO_2$ samples showing the Co region, with Co concentrations (x) obtained by data simulation (solid lines) also included; (b) XRD data of $Sn_{1-x}Co_xO_2$ powders prepared with different values of x; powder diffraction files of orthorhombic $SnO_2$ (solid thin lines, marked O), tetragonal $SnO_2$ (solid thick lines, marked C), and SnO (thick dashed lines, marked R) phases are also shown; the * indicates weak peaks of $Co_3O_4$ observed only in samples with x≧0.08; (c) TEM images of $Sn_{1-x}Co_xO_2$ prepared at 600° with x=0.01; the inset shows electron diffraction patterns taken from selected regions of the TEM images; (d) TEM images of $Sn_{1-x}Co_xO_2$ prepared at 600° with x=0.05; the inset shows electron diffraction patterns taken from selected regions of the TEM images; (e) TEM images of $Sn_{0.99}Co_{0.01}O_2$ prepared at 350° C.; (f) XRD data of $Sn_{1-x}Co_xO_2$ powders prepared with by annealing at different temperatures; the bottom and top panels show data from samples annealed in air and in flowing hydrogen (10% $H_2$ and 90% He) respectively; powder diffraction files of orthorhombic $SnO_2$ (solid thin lines, marked O), tetragonal $SnO_2$ (solid thick lines, marked C), and SnO (thick dashed lines, marked R) phases are also shown.

Typical PIXE spectra from $Sn_{1-x}Co_xO_2$ samples are shown in FIG. 5(a). The Co concentrations of 1.4, 3.5 and 5.4% estimated by simulating the experimental PIXE spectra after removing the background due to bremsstrahlung are in reasonable agreement with their nominal concentrations of 1, 3, 5% Co respectively.

B. Crystalline Structure of the Compositions

X-ray diffraction (XRD) studies utilizing the Debye-Scherrer technique were used to determine the crystalline structure of the compositions obtained. XRD spectra were recorded at room temperature on a Phillips X'Pert x-ray diffractometer with a $CuK_\alpha$ source ($\lambda=1.5418$ Å) is Bragg-Brentano geometry. The loose powder samples were leveled in the sample holder to ensure a smooth surface and mounted on a fixed horizontal sample plane. Data analyses were carried out using profile fits of selected XRD peaks.

Figures 6A, 6B:
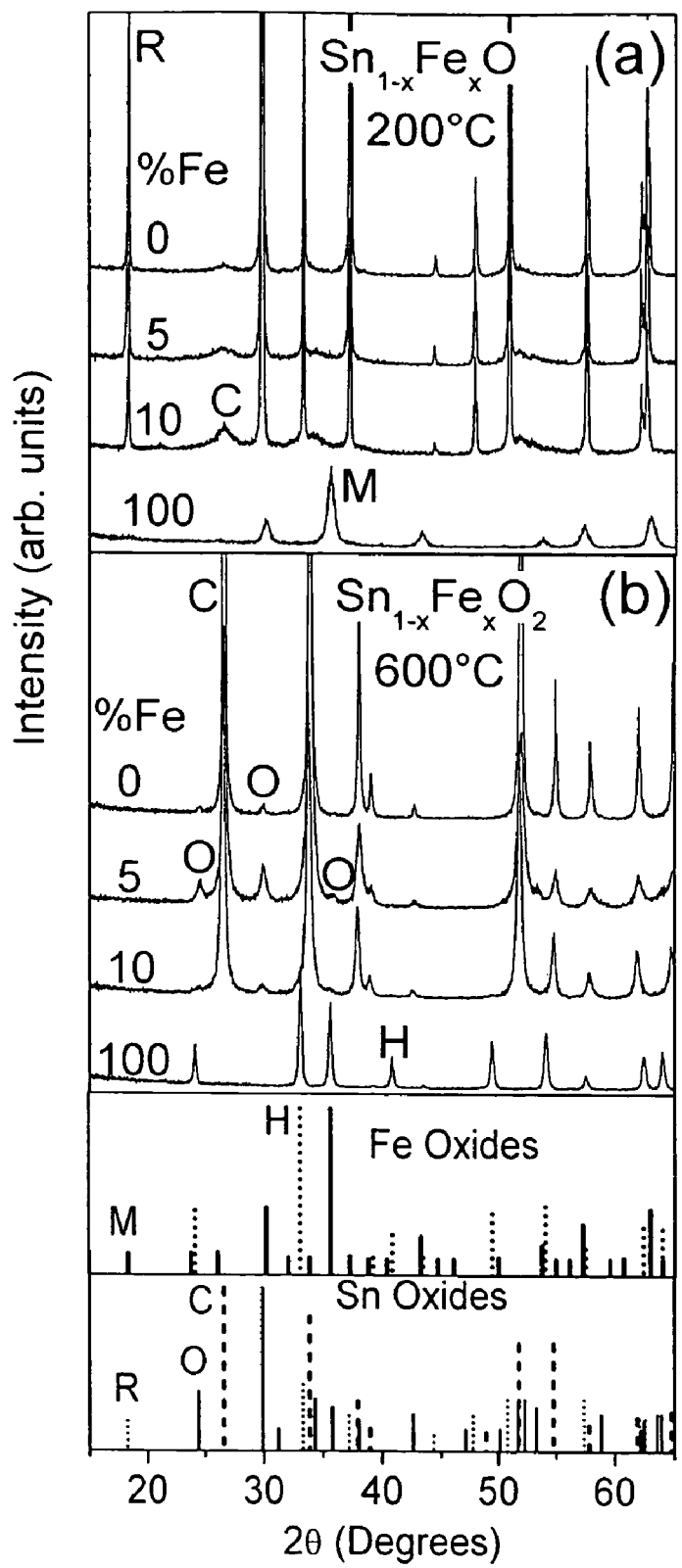
FIGS. 6(a) and 6(b) show XRD patterns of $Sn_{1-x}Fe_xO$ (prepared at 200° C.), and $Sn_{1-x}Fe_xO_2$ (prepared at 600° C.), respectively, along with reference lines of orthorhombic $SnO_2$ (solid lines, marked "O"), romarchite SnO (dotted lines, marked "R"), cassiterite $SnO_2$ (dashed lines, marked "C") phases, hematite (marked "H"), and maghemite (marked "M") phases of $Fe_2O_3$.
Figures 7A, 7B, 7C:
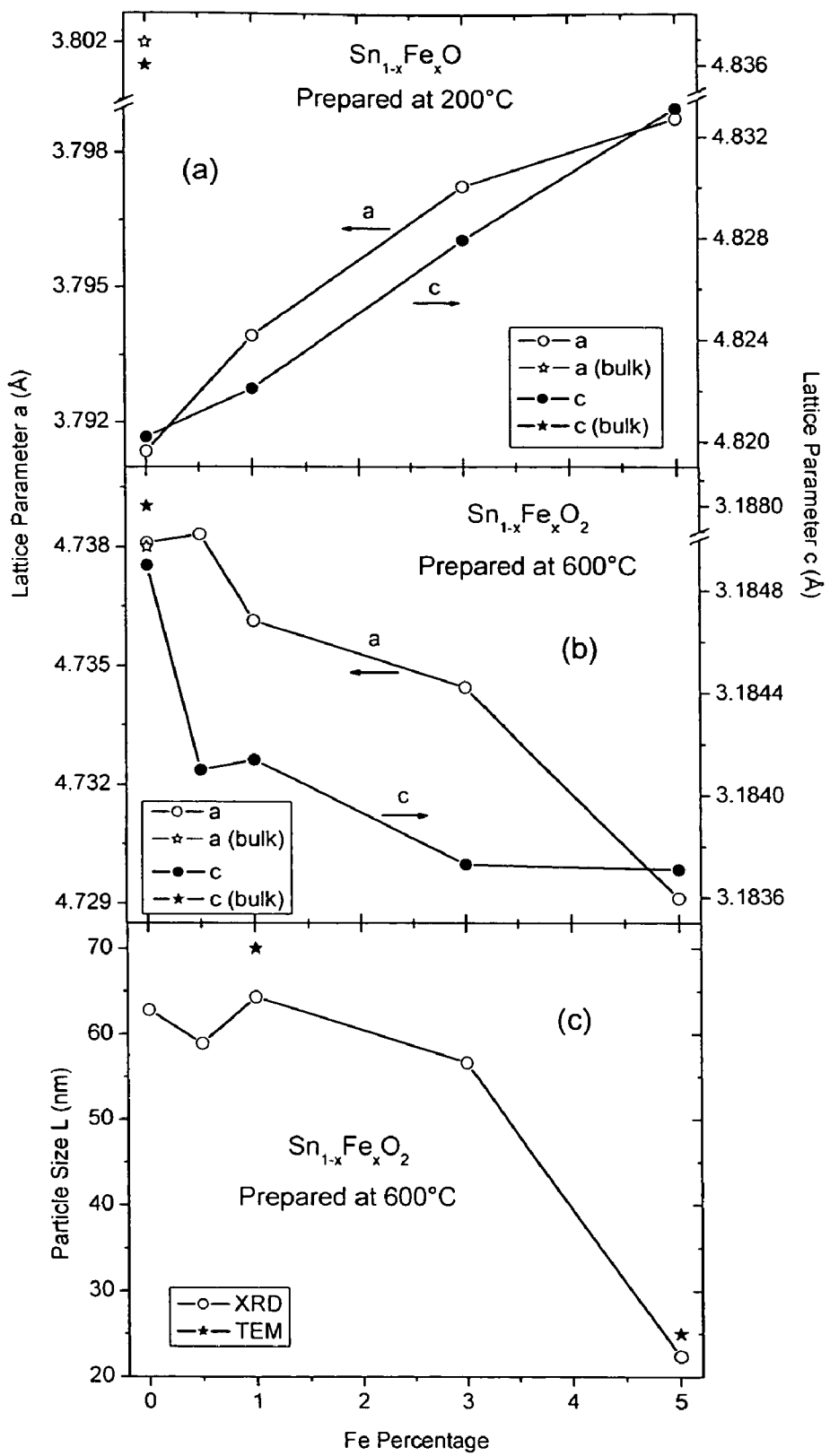
FIG. 7 shows (a) changes in the lattice parameters a and c of tetragonal SnO calculated using (101) and (110) peaks as a function of Fe percentage, as well as the reported magnitude of the lattice parameters of bulk SnO; (b) changes in the lattice parameters a and c of cassiterite $SnO_2$ calculated using the (110) and (202) peaks as a function of Fe percentage, as well as the reported magnitude of the lattice parameters of bulk $SnO_2$; (c) particle size of $Sn_{1-x}Fe_xO_2$ as a function of x calculated from the tetragonal cassiterite XRD peak (110), with particle sizes determined from TEM marked with stars.

As shown in FIG. 6(b), the powder $Sn_{1-x}Fe_xO_2$ samples showed strong XRD peaks due to the cassiterite phase of $SnO_2$, with much weaker peaks of the metastable orthorhombic $SnO_2$ phase. The peak intensities, positions, and widths of the XRD lines changed with x in $Sn_{1-x}Fe_xO_2$, as shown in FIG. 6(b). Lattice parameters a and c and the particle size L, as shown in FIGS. 7(b) and 7(c), estimated using the cassiterite (110) and (202) peaks of the nanoscale samples of $Sn_{1-x}Fe_xO_2$, decreased as x increased from 0.005 to 0.05.

Figures 8A, 8B:
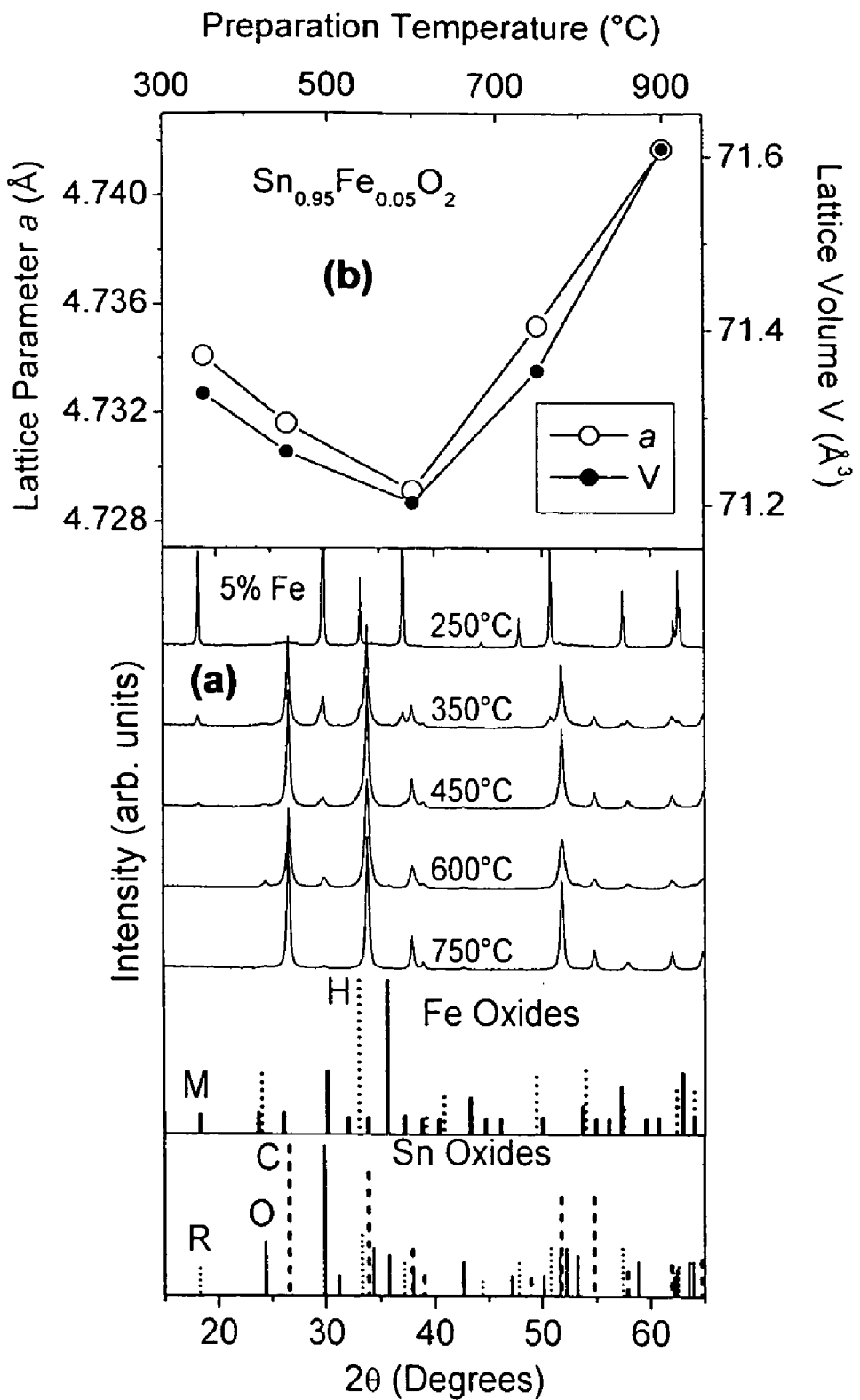
FIGS. 8 (a) and (b) show (a) XRD patterns of 5% Fe-doped samples prepared by annealing the reaction precipitate at different temperatures shown above, along with reference lines of orthorhombic $SnO_2$ (solid lines, marked "O"), romarchite SnO (dotted lines, marked "R") cassiterite $SnO_2$ (dashed lines, marked "C") phases, hematite (marked "H") and maghemite (marked "M") phases of $Fe_2O_3$; (b) Changes in the lattice parameter a and the lattice volume of cassiterite $Sn_{0.95}Fe_{0.05}O_2$ as a function of preparation temperature. The change in the lattice parameter c was minimal.

The XRD patterns of powder $Sn_{1-x}Fe_xO$ samples, on the other hand, showed strong peaks of tetragonal SnO with some weak $SnO_2$ traces, as shown in FIG. 6(a). The lattice parameters a and c, determined using the (101) and (110) peaks, showed an increase with x, as shown in FIG. 7(a). The experimentally determined lattice parameters of the pure SnO samples are lower than that reported for pure synthetic bulk romarchite; this may be due to changes in the oxygen stoichiometry and/or particle size effect.

tetragonal SnO phase was observed at 200° C. and showed a gradual conversion to the $SnO_2$ phase with increasing preparation temperature until its apparent disappearance at $\geq 450$° C., as illustrated in FIG. 8(a). The lattice parameter a and the unit cell volume V decreased, and the lattice parameter c increased with increased preparation temperature in the 350 to 600° C. range, as shown in FIG. 8(b). Above 600° C., these trends were reversed, and the lattice volume approached closer to the pure $SnO_2$ range.

Figures 9A, 9B, 9C, 9D:
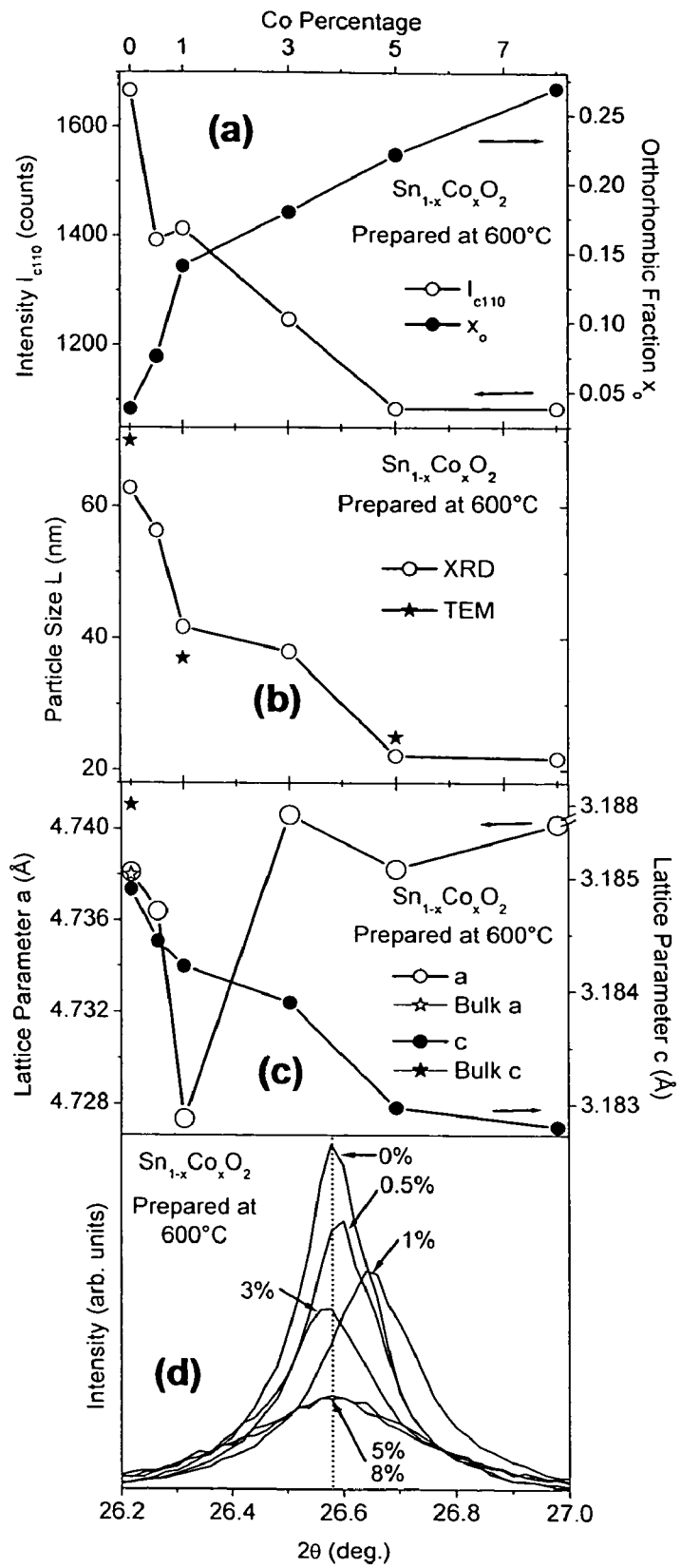
FIGS. 9 (a)-(d) show (a) intensity of the tetragonal cassiterite peak (110) and the orthorhombic fraction $x_0$ of $Sn_{1-x}Co_xO_2$ prepared at 600° C. as a function of Co percentage; (b) the particle size of $Sn_{1-x}Co_xO_2$ as a function of x calculated from the XRD tetragonal cassiterite peak (110). The particle sizes determined from TEM are marked with stars; (c) changes in the lattice parameters a and c of cassiterite $SnO_2$ as a function of Co percentage. Stars indicate the bulk values of the $SnO_2$ lattice parameters from XRD reference files; (d) changes in the (110) cassiterite peak position with Co concentration. The lattice parameters were calculated using (110) and (202) peaks of the tetragonal cassiterite phase.

XRD patterns of the $Sn_{1-x}Co_xO_2$ samples showed the formation of tetragonal cassiterite $SnO_2$ with a very small fraction of metastable orthorhombic phase. For $x \geq 0.08$, weak peaks of $Co_3O_4$ started appearing and gradually strengthened with increasing Co doping, suggesting a saturation limit of Co in $SnO_2$. It is noted that with increasing Co concentration, the intensity of the cassiterite $SnO_2$ phase decreased while the relative concentration of the orthorhombic phase gradually increased. Changes in the XRD peak intensity of the cassiterite phase ($I_{c110}$) and the orthorhombic phase fraction ($x_o$) of $SnO_2$ are shown in FIG. 9(a). The orthorhombic fraction $x_o$ was calculated using the method of standard additions, $$x_o = \frac{K}{K + (I_{c110}/I_{o111})},$$

using K=2.69. Formation of the high-temperature orthorhombic $SnO_2$ phase at ambient conditions has been observed in thin films and nanoscale powders. Nucleation of the metastable orthorhombic phase has been attributed to thin film strains and size-dependent internal pressures due to surface stresses in nanoparticles. Therefore, the increasing orthorhombic fraction of $SnO_2$ with Co concentration indicates that Co doping causes structural disorder and strain, and possible changes in the particle size. The growth of the orthorhombic fraction is fast up to 1% Co, above which a slower growth is observed, as shown in FIG. 9(a). This suggests that the intrinsic doping mechanisms active in the Co concentration regimes above and below 1% may be different.

Average particle size L of the tetragonal SnO₂ phase was calculated using the width of the (110) peak and the Scherrer relation, $$L = \frac{0.9\lambda}{B\cos\theta}$$

(where $\theta$ is the peak position, $\lambda$ is the x-ray wavelength and $B=(B_m^2-B_s^2)^{1/2}$ was estimated using the measured peak width $B_m$ and the instrumental width $B_s$). These estimates showed that the crystallite size decreased with increased Co doping, as shown in FIG. 9(b). This, combined with the TEM images discuss below, indicates that Co doping inhibits the growth of SnO₂ nanoparticles.

XRD peak positions showed significant changes with Co doping as shown in FIGS. 9(c) and 9(d). The tetragonal cassiterite SnO₂ peaks initially shifted to the higher 2θ angles as x increased to 0.01, as shown in FIG. 9(d). But for x=0.03, there is a dramatic shift to the lower angles followed by moderate changes in the peak positions at higher x. These changes revealed interesting variations in the lattice parameters a and c with Co concentration as shown in FIG. 9(c). The SnO₂ lattice parameter a initially decreased due to Co doping for x≦0.01. Such a rapid contraction of the lattice can be understood qualitatively considering the sizes of the ions and their local coordinations. Substitution of 0.69 Å sized Sn⁴⁺ ions with 0.58 Å sized Co²⁺ ions is expected to reduce the interatomic spacing significantly, justifying the initial contraction of the lattice for x≦0.01. The observed rapid expansion of the lattice for x=0.03 indicates a significantly different doping mechanism. At higher doping concentrations, the incorporation of dopant ions in interstitial sites has been reported in some host systems causing somewhat similar structural changes in the lattice parameters.

Interstitial incorporation of Co²⁺ ions might cause significant changes and disorder in the SnO₂ structure as well as many dramatic changes in the properties of the material, which is discussed in the following sections. The large difference in the charges and coordination numbers of Sn⁴⁺ and Co²⁺ ions will also contribute to the structural disorder in SnO₂ due to the removal of some oxygen ions that were attached to the octahedrally coordinated Sn⁴⁺. For x≧0.03, the observed expansion along the a-direction and continued contraction along the c-direction shown in FIG. 9(c) will contribute to changes in the shape of the SnO₂ lattice and the nanoparticles. This was indeed observed in the TEM measurements reported below. On increasing the Co concentration to 5%, the spherical SnO₂ particles (observed in the undoped as well as 1% Co doped samples) appeared as nanorods with an aspect ratio as high as 3.

In FIG. 5(b), x-ray diffractograms (XRD) of $Sn_{1-x}Co_xO_2$ samples prepared by annealing the dried precipitate at 600° C. for 6 hours are shown. All samples showed strong peaks due to the rutile-type cassiterite (tetragonal) phase of SnO₂ with relatively weaker peaks of metastable orthorhombic phase. Although cassiterite is the stable phase under ambient conditions, the orthorhombic phase also was observed in SnO₂ synthesized by various methods. The peak positions of the XRD lines of both phases did not show any measurable change, but the intensities of the peaks of the orthorhombic phase increased while that of the rutile (cassiterite) SnO₂ phase decreased with increasing x, as shown in FIG. 5(b). As x increases, the XRD peaks appeared wider, indicating possible changes in the crystallite size and/or strain. No trace of cobalt metal, oxides, or any binary tin cobalt phases, were observed in any of the samples doped with up to 5% Co, which is well above the detection limit (~1.5%) of the x-ray diffractometer used. At higher x, additional peaks of Co₃O₄ started appearing. The formation of $Sn_{1-x}Co_xO_2$ at high temperatures with x≦0.08 has been reported using a solid state reaction method, although at lower temperatures the solubility was ≦2%. The wet chemical process used in this work is expected to increase the solubility limit.

C. Optical Properties of the Cobalt-Doped Tin Dioxide

Room-temperature optical spectra in the ultraviolet and visible light wavelength ranges were collected for the $Sn_{1-x}Co_xO_2$ samples using a CARY 5000 spectrophotometer fitted with an integrating sphere diffuse reflectance accessory. The spectrophotometer measures reflectance relative to a background scatterer, which was powdered BaSO₄. These studies indicated that samples with x≦1 do not have any Co₃O₄ phases.

Figures 10A, 10B:
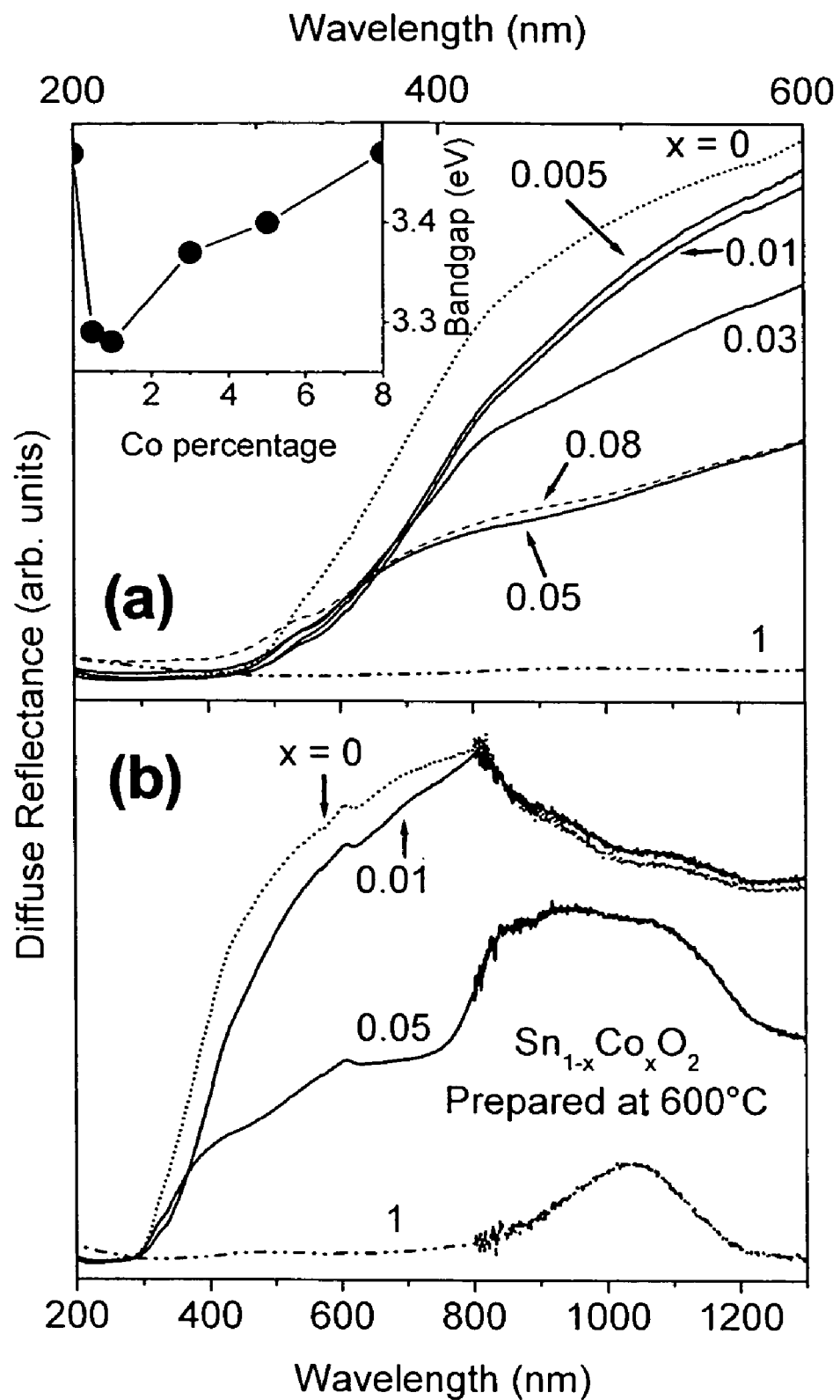
FIGS. 10 (a) and (b) show diffuse reflectance spectra of $Sn_{1-x}Co_xO_2$ samples prepared at 600° C. (a) The changes in the absorption edge with Co concentration; inset in panel (a) shows the changes in the band gap energy estimated from the reflectance data as a function of Co concentration and (b) shows the complete spectra indicating the extent of $Co_3O_4$ formation.

Preliminary optical characterization of the pure and Co doped SnO₂ powders were carried out by measuring the diffuse reflectance at room-temperature. FIG. 10(a) shows a shift of the absorption edge to longer wavelengths/lower energies and a decrease in the band gap of SnO₂ for x≦0.01. Increasing the Co doping above this level reversed the trend in that the band gap increased gradually and a reduction in the reflectance was observed with Co percentage. The diffuse reflectance, R, of the sample is related to the Kubelka-Munk function F(R) by the relation $F(R)=(1-R)^2/2R$, where R is the percentage reflectance. The spectra used for the band gap calculations are plotted in terms of F(R). The bandgap energies of the $Sn_{1-x}Co_xO_2$ powders were calculated from their diffuse-reflectance spectra by plotting the square of the Kubelka-Munk function, $F(R)^2$ vs. energy in electron volts. The linear part of the curve was extrapolated to $F(R)^2=0$ to get the direct bandgap energy.

Diffuse reflectance measurements carried out on a pure nanoscale Co₃O₄ reference sample prepared using an identical procedure (with x=1), showed prominent signatures at lower energies as shown in FIG. 10(b). Comparison of the optical spectra of $Sn_{1-x}Co_xO_2$ samples with this suggests that samples with x≦0.01 do not have any Co₃O₄ phase. However, evidence of its presence was observed in all samples with x≧0.03. This indicates that in samples with x=0.03 and 0.05, at least a fraction of the Co atoms precipitate as Co₃O₄, although XRD shows its formation only for x≧0.08. Since the detection limit of the x-ray diffractometer employed was 1.5% (determined from XRD measurements of the physical mixtures of SnO₂ (x=0) and Co₃O₄ (x=1) nanoparticles prepared under identical synthesis conditions), the fraction of Co forming Co₃O₄ in 3% and 5% Co doped SnO₂ should only be below this level. This explains why the lattice parameters, band gap, particle size, shape, and orthorhombic/tetragonal fractions continue to change for x>0.01 although the changes are relatively smaller in this range as illustrated in FIGS. 9 and 10.

D. Raman Spectra of the $Sn_{1-x}Co_xO_2$ Samples

Raman spectra were collected for the $Sn_{1-x}Co_xO_2$ samples using a Renishaw S2000 Raman microscope. Samples were all probed using identical instrument conditions: 783 nm diode laser, 1200 line/mm grating, over a Stokes Raman shift range of 50-1000 cm⁻¹. A line focus accessory was also employed, which permitted the collection of photon scatter data from an area ~2 μm by 60 μm, rather than a discreet 1-2 μm diameter spot. Incident laser power was not measured; however, power at the laser head was ~28 mW, which would be expected to produce ~2-4 mW at the sample. Sample preparation consisted of loosely packing the powder into a stainless steel die accessory, which was then mounted on the microscope stage for probing.

Figures 11A, 11B, 11C:
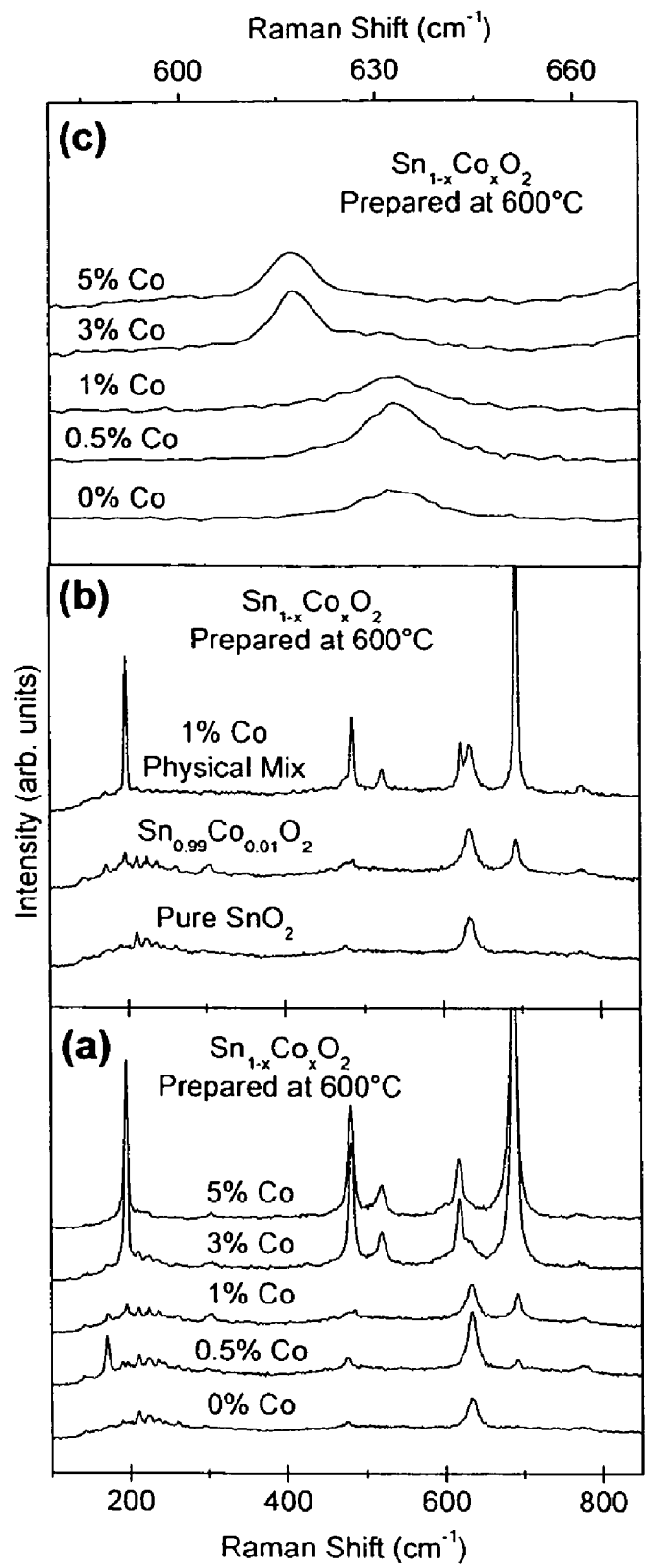
FIGS. 11 (a)-(c) show (a) Raman spectra of $Sn_{1-x}Co_xO_2$ prepared at 600° C. as a function of x; (b) Raman spectra of pure $SnO_2$, 1% Co-doped $SnO_2$ and a physical mixture of pure $SnO_2$ and $Co_3O_4$; (c) the apparent disappearance of $SnO_2$ Raman peak at 630 $cm^{-1}$ and the emergence of the 617 $cm^{-1}$ peak of $Co_3O_4$ for x>0.01.

FIG. 11 (a) shows the Raman spectra of $Sn_{1-x}Co_xO_2$ samples as a function of Co concentration. The pure $SnO_2$ spectrum shown in FIGS. 11 (a) and 11 (b) shows the classic cassiterite $SnO_2$ vibrations at 476 $cm^{-1}$, 630 $cm^{-1}$, and 776 $cm^{-1}$. Addition of 0.5 or 1.0 molar percent Co results in the appearance of two new peaks at 300 $cm^{-1}$ and 692 $cm^{-1}$. However, no significant change in the $SnO_2$ peak positions or widths were observed for these doping concentrations. These new Raman peaks at 300 $cm^{-1}$ and 692 $cm^{-1}$ may be due to the vibrational modes activated by local structural changes resulting from the substitution of $Co^{2+}$ ions at the $Sn^{4+}$ sites. Further addition of Co to 3 or 5 molar percent results in the appearance of peaks at 196 $cm^{-1}$, 480 $cm^{-1}$, 520 $cm^{-1}$, 617 $cm^{-1}$ and 688 $cm^{-1}$. These five peaks observed in the samples with $x \geq 0.03$ match well with published Raman data of $Co_3O_4$. The appearance of $Co_3O_4$ vibrational modes is in good agreement with the result from the optical data that predicts at least a fraction of the doped Co precipitates out as $Co_3O_4$ for $x \geq 0.03$ For $Sn_{1-x}Co_xO_2$ samples with $x \geq 0.03$, there is an apparent disappearance of the $SnO_2$ peaks. This disappearance is most obvious for the 630 $cm^{-1}$ $SnO_2$ peak as illustrated in FIG. 11 (c) and would suggest a loss of the $SnO_2$ phase. However, the 776 $cm^{-1}$ $SnO_2$ peak is still visible in the 3 and 5% Co doped samples. At best, its intensity has diminished by a factor of 2. The extensive peak broadening and the subsequent disappearance of the 630 $cm^{-1}$ peak and the loss in intensity of the 776 $cm^{-1}$ peak are indicative of significant structural modifications and disorder of the $SnO_2$ lattice for $x \geq 0.03$. Based on the drastic changes observed in the lattice parameter a, particle size and particle shape, this disappearance of the Raman peak also may be due to the interstitial incorporation of $Co^{2+}$ ions and the subsequent structural changes.

As discussed above, at 0.5 and 1 molar percent of Co, a small Raman peak is present at 692 $cm^{-1}$. However, when the Co molar percentage is increased to 3, an intense Raman peak at 688 $cm^{-1}$ appears. The width of the 688 $cm^{-1}$ peak precludes determination if the 692 $cm^{-1}$ is still present. Two obvious conclusions are possible: i) the 692 $cm^{-1}$ peak represents a very small amount of $Co_3O_4$, and ii) the 692 $cm^{-1}$ mode represents a vibrational mode of $Sn_{1-x}Co_xO_2$. FIG. 11 (b) compares the Raman spectra of undoped $SnO_2$ and 1% Co doped $SnO_2$ (both prepared at 600° C. through identical procedures) and the Raman spectrum of a physical mixture of $SnO_2$ and $Co_3O_4$ with 1 molar percent Co (both prepared separately at 600° C.). For the physical mixture, no annealing was performed following the mixing. The Raman spectrum of the physical mixture is clearly a superposition of a $SnO_2$ spectrum and a $Co_3O_4$ spectrum. It is also clear that the intensity of the $SnO_2$ peaks in the undoped $SnO_2$, the 1% Co doped $SnO_2$, and the physical mixture samples, are essentially the same. This indicates that the same percentage of $SnO_2$ in the cassiterite form is present in all three samples. The intensity of the 692 $cm^{-1}$ peak in the 1% doped sample is roughly 1/10 that of the 688 $cm^{-1}$ peak in the physical mixture. This disparity in intensity suggests that even if we assign the 692 $cm^{-1}$ peak to traces of $Co_3O_4$, then there is no more than 0.1% $Co_3O_4$ in the 1% Co doped sample.

E. Shape and Size of the Particles in the Compositions

The shape and size of the particles in the compositions were determined using transmission electron microscopy. This showed that the $Sn_{1-x}Fe_xO_2$ particles were all elongated with their average aspect rations changing from 1.25 and 70 nm long for x=0.01 to 1.7 and 25 nm long for x=0.05. It is estimated that for ferromagnetic $Sn_{1-x}Fe_xO_2$ in this preferred embodiment, 95% of the particles are shorter than 100 nm long. It is estimated that at least 95% of the $Sn_{1-x}Co_xO_2$ particles are less than 50 nm long.

High-resolution transmission electron microscopy (TEM) analysis was carried out on a JEOL JEM 2010 microscope with a specified point-to-point resolution of 0.194 nm. The operating voltage of the microscope was 200 kV. All images were digitally recorded with a slow scan CCD camera (image size 1024×1024 pixels), and image processing was carried out using the Digital Micrograph software from Gatan (Pleasant, Calif.). Energy dispersive x-ray spectroscopy (EDX) was carried out using the Oxford Link system attached to the TEM.

Figures 12A, 12B, 12C:
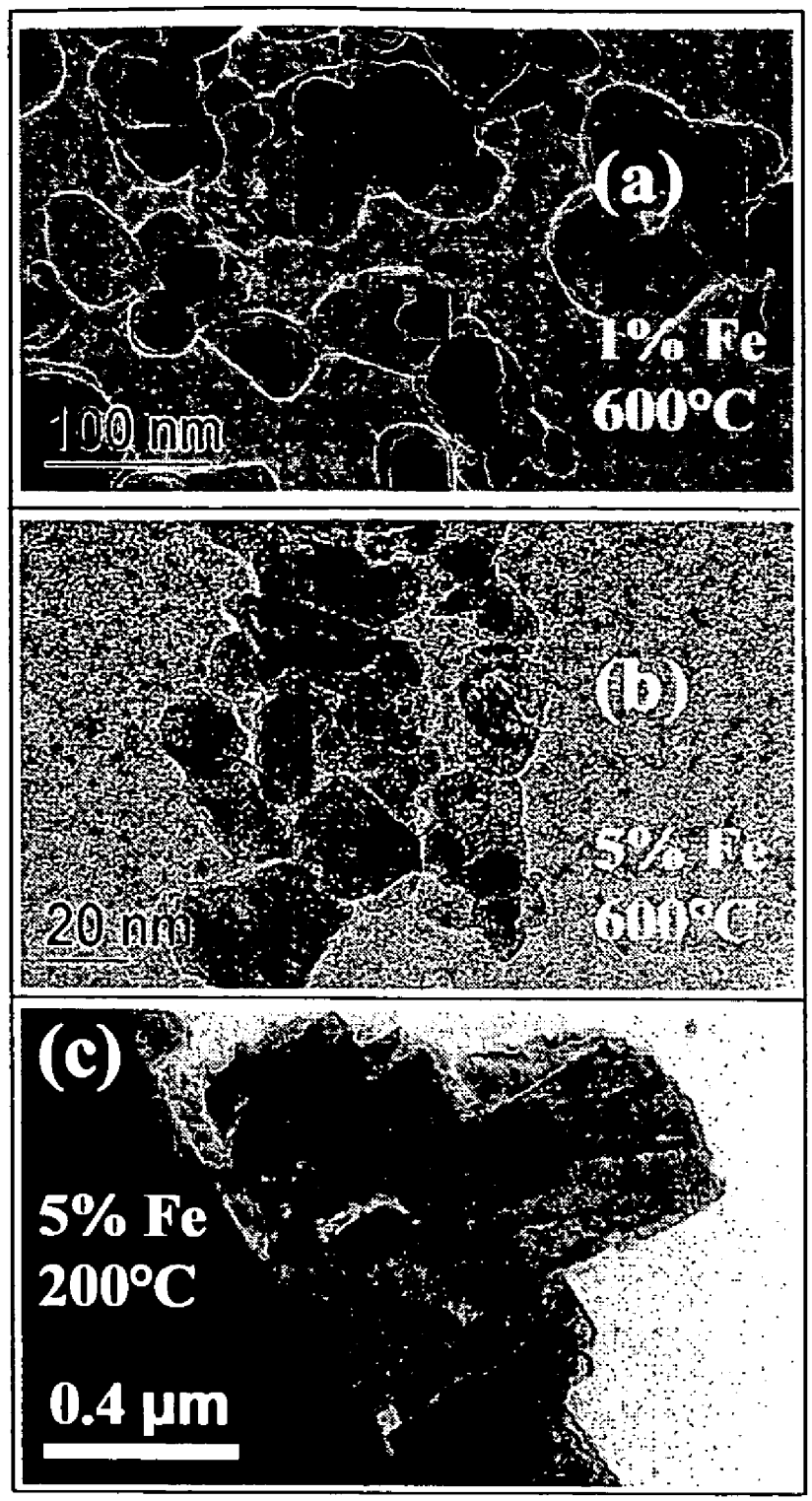
FIGS. 12 (a)-(c) show panels (a) and (b) which show transmission electron microscopy (TEM) images of $Sn_{1-x}Fe_xO_2$ prepared at 600° C. with x=0.01 and 0.05, respectively. Panel (c) shows the TEM image of $Sn_{1-x}Fe_xO_2$ prepared at 200° C. with x=0.05.
Figures 13A, 13B:
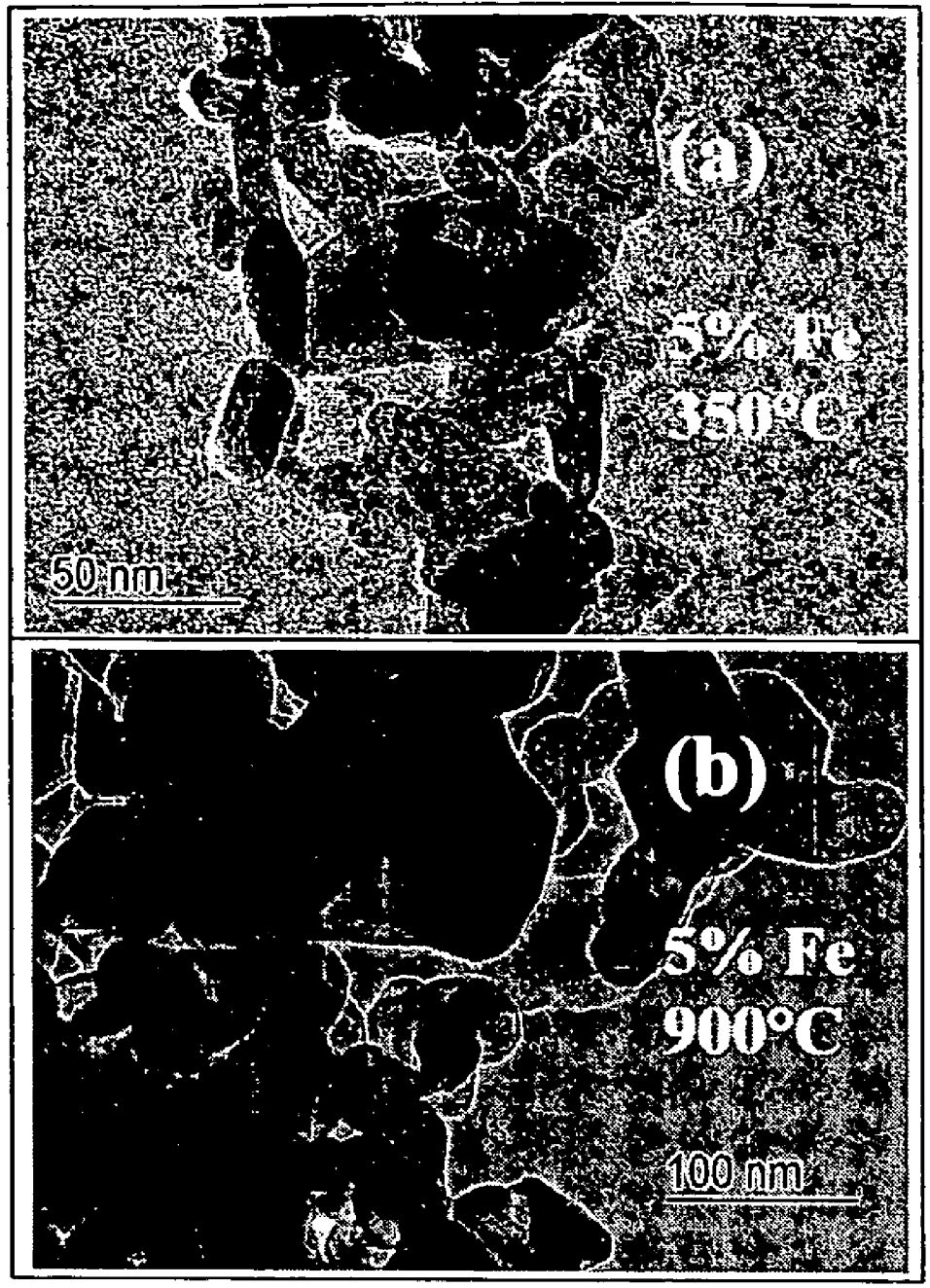
FIGS. 13 (a) and (b) show panels (a) and (b) which show TEM images of $Sn_{0.95}Fe_{0.05}O_2$ prepared at 350 and 900° C. respectively.

The transmission electron microscopy measurements showed significant changes in the shape and size of the $Sn_{1-x}Fe_xO_2$ particles depending on the level of Fe-doping and the preparation temperature. $Sn_{1-x}Fe_xO_2$ particles prepared at 600° C. are shown in FIGS. 12(a) and 12(b). These particles were all elongated with their aspect ratios and average length L changing from ~1.25 and 70 nm, for x=0.01, to 1.7 and 25 nm for x=0.05. $Sn_{0.95}Fe_{0.05}O_2$ particles annealed at 600° C. and 900° C. are shown in FIGS. 13(a) and 13(b). It is estimated that for ferromagnetic $Sn_{1-x}Co_xO_2$ in this preferred embodiment, 95% of the particles are shorter than 100 nm long. These crystallite sizes match very well with similar estimates obtained from the XRD data, shown in FIG. 7(c). The energy dispersive x-ray spectroscopy measurements carried out on 1% and 5% Fe-doped $SnO_2$ samples showed Fe concentrations in reasonable agreement with the estimates obtained from PIXE studies. The TEM images of the $Sn_{1-x}Fe_xO_2$ samples showed the presence of large micron-sized particles with a different shape, as shown in FIG. 12(c).

TEM images also revealed significant differences in the shape of the 600° C. prepared $Sn_{1-x}Co_xO_2$ particles doped with different percentages of Co. The $Sn_{0.99}Co_{0.01}O_2$ nanoparticles shown in FIG. 5(c) were equiaxed (nearly spherical in shape) with an average diameter of 37 nm, which is about half the average size of the pure $SnO_2$ particles (~70 nm) prepared under similar conditions. In contrast, the $Sn_{0.95}Co_{0.05}O_2$ particles shown in FIG. 5(d) were elongated into nanorods with an average aspect ratio of about 3. The $Sn_{0.99}Co_{0.01}O_2$ particles had a higher average volume of 25000 $nm^3$ in comparison to the $Sn_{0.95}Co_{0.05}O_2$ particles (average volume ~10000 $nm^3$). It is estimated that at least 95% of the particles are less than 50 nm long. Electron diffraction patterns taken from an aggregate of particles belonging to each of these samples, shown in the insets of FIGS. 5(c) and 5(d), revealed characteristic ring patterns that confirm the structure and phase purity measured by XRD. The differences in the particle sizes and shapes observed in the TEM data as well as the systematic changes in the linewidth and intensity of the XRD peaks with increasing Co % seem to be the result of Co incorporation into the $SnO_2$ lattice. The Co incorporation will most likely result in structural rearrangements to take care of the ionic size differences and charge neutrality. However, more detailed investigations are required to fully understand these structural changes.

F. Mossbauer Spectra of $Sn_{1-x}Co_xO_2$

Mossbauer spectroscopy measurements showed that $Sn_{0.95}Fe_{0.05}O_2$ exhibited ferromagnetically ordered $Fe^{3+}$ spins when prepared at 350° C., but that these ferromagnetically ordered $Fe^{3+}$ spins were converted to a paramagnetic spin system as the preparation temperature increased to 600° C. For these measurements, randomly oriented absorbers were prepared by mixing approximately 30 mg of sample with petroleum jelly in a 0.375 inch thick and 0.5 inch internal diameter Cu holder sealed at one end with clear tape. The holder was entirely filled with the sample mixture and sealed at the other end with tape. Spectra were collected using a 50 mCi (initial strength) $^{57}$Co/Rh source. The velocity transducer MVT-1000 (WissEL) was operated in constant acceleration mode (23 Hz, ∓12 mm/s). An Ar—Kr proportional counter was used to detect the radiation transmitted through the holder, and the counts stored in a multichannel scalar as a function of energy (transducer velocity) using a 1024 channel analyzer. Data were folded to 512 channels to give a flat background and a zero-velocity position corresponding to the center shift (CS or $\delta$) of a metallic iron foil at room temperature. Calibration spectra were obtained with a 20 μm thick α-Fe(m) foil (Amersham, England) placed in exactly the same position as the samples to minimize any errors due to changes in geometry. Sample thickness corrections were not carried out. The data were modeled with RECOIL software (University of Ottawa, Canada) using a Voigt-based spectral fitting routine.

Figures 14A, 14B, 14C:
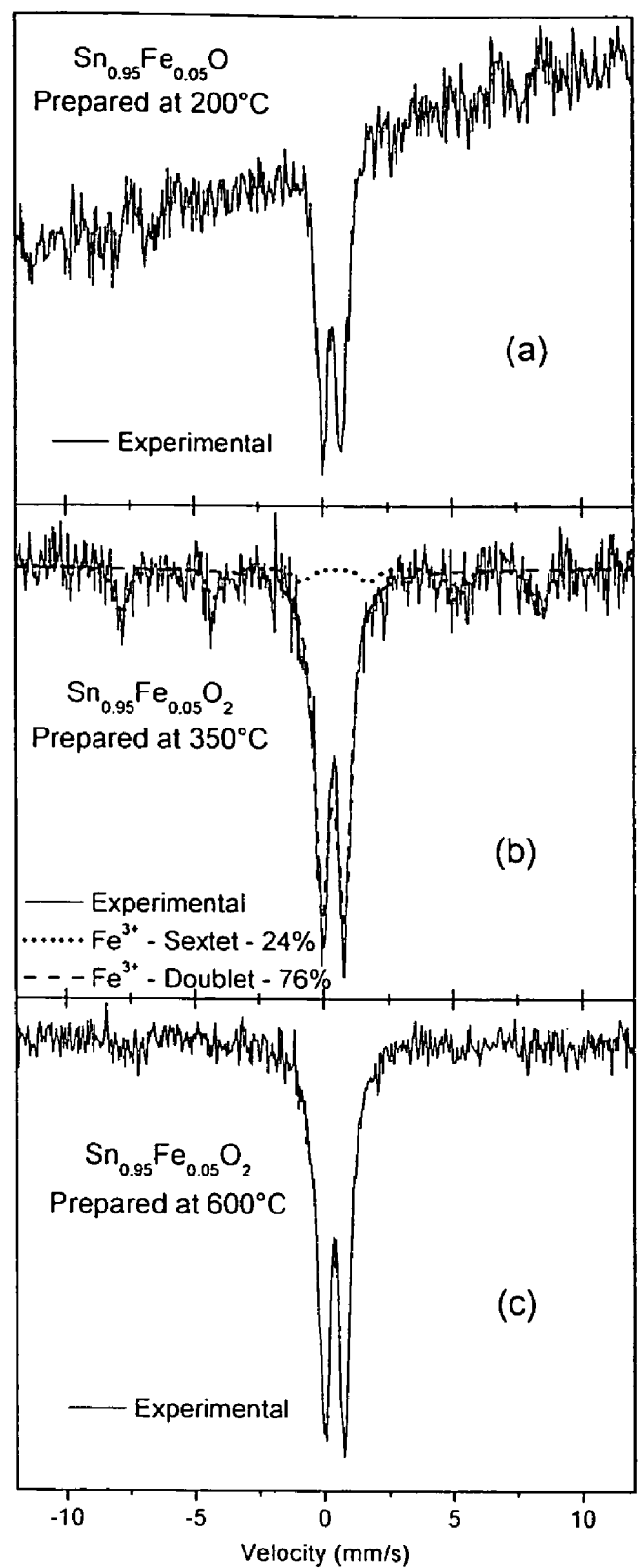
FIGS. 14 (a)-(c) show panel (a) which shows the room-temperature Mössbauer spectra of $Sn_{0.95}Fe_{0.05}O$. Panels (b) and (c) show the room-temperature Mössbauer spectra of $Sn_{0.95}Fe_{0.05}O_2$ prepared at 350 and 600° C., respectively.

Three selected samples, $Sn_{0.95}Fe_{0.05}O$ prepared at 200° C., $Sn_{0.95}Fe_{0.05}O_2$ prepared at 350° C., and $Sn_{0.95}Fe_{0.05}O_2$ prepared at 600° C., were investigated using Mossbauer spectroscopy, and their spectra are shown in FIG. 14. The $Sn_{0.95}Fe_{0.05}O$ sample prepared at 200° C. showed a well-defined doublet in FIG. 14(a), suggesting that the incorporated Fe is paramagnetic and in the 3+ oxidation state in an octahedral environment. No evidence of any $Fe^{2+}$ ions was detected in this sample.

Experimental and fit-derived RT Mossbauer spectra of the $Sn_{0.95}Fe_{0.05}O_2$ sample prepared at 350° C. are shown in FIG. 14(b). The spectrum displayed a well-defined sextet (magnetic component spanning 24% of the spectral area) and a central doublet (paramagnetic component spanning 76% of the spectral area). The fit-derived parameters of the Fe sextet are center shift $\delta=0.38$ mm/s, quadrupole shift parameter $\epsilon=-0.1$ mm/s, and hyperfine magnetic field $B_{hf}=50.3$ T, whereas the parameters of the doublet are $\delta=0.37$ mm/s and quadrupole shift $\epsilon=-0.1$ mm/s.

FIG. 14(b) shows that the sextet feature (magnetic component of the sample) of the $Sn_{0.95}Fe_{0.05}O_2$ prepared at 350° C. is not due to crystalline bulk Fe oxides such as magnetite, hematite, goethite, or maghemite. Magnetite, a mixed oxide of $Fe^{2+}$ and $Fe^{3+}$, displays two well-defined sextets in its RT Mossbauer spectrum because of the presence of Fe in both tetrahedral ($Fe^{3+}$) and octahedral sites ($Fe^{2+}$ and $Fe^{3+}$ at a 1:1 ratio displays a sextet peak due to $Fe^{2.5+}$ because of Verwey transition): A and B sites of the inverse spinel structure. Hematite, on the other hand, displays a well-defined sextet with $B_{hf}=51.8$ T, $\delta=0.37$ mm/s, and $\epsilon=-0.20$ mm/s, which is not shown in FIG. 14(b). Goethite displays a well-defined sextet with $B_{hf}=38$ T, $\delta=0.37$ mm/s, and $\epsilon=-0.26$ mm/s, which is also not shown in FIG. 14(b). The sextet feature shown in FIG. 14(b) is also unlikely to be due to maghemite, which has $B_{hf}=50$ T, $\delta=0.23$ to 0.35 mm/s, and $\epsilon=-0.02$ mm/s. The experimental conditions employed to synthesize the binary oxides in this research also implied nonformation of maghemite.

The derived Mossbauer parameters of the central doublet, which is due to contribution from paramagnetic Fe site(s) to the sample, do not favor the formation of small particle magnetite and goethite. Small-particle Fe oxides such as magnetite (<10 mm), goethite (<15 nm), and hematite (<8 nm) display a doublet at room temperature (well below their magnetic ordering temperature) due to superparamagnetism. The parameters of the doublet in FIG. 14(b), however, are inconsistent with superparamagnetic iron oxides. The derived Mossbauer parameters of magnetite and hematite are $\delta=0.22$ mm/s, and $\epsilon=0$ 0.6 mm/s, and $\delta=0.35$ mm/s, and $\epsilon=0.49$ mm/s, respectively, while the quadrupole splitting of goethite is around $\epsilon=0.48$ mm/s. Moreover, any such iron oxides, if present in the superparamagnetic nanoparticle form, cannot produce the hysteresis loops with a finite coercivity (~60 Oe) observed in the magnetic studies. This observation, along with the nonformation of "large" particle magnetite, hematite, and goethite in the sample, implies an absence of conditions that would dictate their formation. Therefore, it is believed that iron oxide does not exist in the preferred embodiment of iron-doped tin dioxide.

Thus, the Mossbauer data shown in FIG. 14(b), showing the Mossbauer spectra of room-temperature $Sn_{0.95}Fe_{0.05}O_2$ prepared at 350° C., suggest that the sextet results from magnetically ordered $Fe^{3+}$, which constitutes 24% of the incorporated Fe ions. The Mossbauer spectra of room-temperature $Sn_{0.95}Fe_{0.05}O_2$ prepared by annealing the precipitate at 600° C. shown in FIG. 14(c), on the other hand, shows mainly a doublet structure (corresponding to paramagnetic $Fe^{3+}$) with very weak traces of the sextet lines. This clearly suggests that the ferromagnetically ordered $Fe^{3+}$ spins are converted to a paramagnetic spin system as the preparation temperature increased from 350 to 600° C.

E. The Distribution of the Dopant Throughout the Crystallite

1. Confirmation by X-Ray Diffraction Studies of $Sn_{1-x}Fe_xO_2$

X-ray diffraction (XRD) studies utilizing the Debye-Scherrer technique have also shown that the Fe is evenly distributed throughout the $SnO_2$, meaning that there are no phases or clusters of the Fe. The pure iron oxide samples (prepared under identical synthesis conditions, but with no $SnCl_2$) showed maghemite [$\gamma$-$Fe_2O_3$, FIG. 6(a) and hematite [$\alpha$-$Fe_2O_3$, FIG. 6(b) phases, with average particle sizes of 22 and 53 nm at 200 and 600° C. preparations, respectively. No trace of iron metal, oxides, or any binary tin-iron phases were observed in any of the doped samples with $x \leq 0.10$. This is consistent with the reported solubility limit of up to 10% Fe in $SnO_2$ (this, along with the fact that the x-ray diffractometer employed can detect only phases that are $\geq 1.5$%, is why experimental data has been reported only for samples with $x \leq 0.05$). The lack of any observable phases shows that the Fe is evenly distributed throughout the $SnO_2$.

2. Confirmation by X-Ray Photoelectron Spectroscopy Studies

X-ray photoelectron spectroscopy studies (XPS) showed that $Sn_{1-x}Fe_xO_2$ and $Sn_{1-x}Co_xO_2$ prepared according to the methods disclosed herein produce a uniform distribution of the dopant in the entire crystallite. XPS measurements for both Fe-doped and Co-doped $SnO_2$ were performed on powder samples using a Physical Electronics Quantum 2000 Scanning ESCA Microprobe. The system used a focused monochromatic $AlK_\alpha$ x-ray (1486.7 eV) source and a spherical section analyzer. The instrument had a 16 element multichannel detector. The x-ray beam used was a 105 W, 100 μm diameter beam that was rastered over a 1.4 mm×0.2 mm rectangle on the sample. The powder samples were mounted using a small amount of double-coated carbon conductive tape. The x-ray beam was incident normal to the sample and the photoelectron detector was at 45° off-normal. Data were collected using a pass energy of 46.95 eV. For the Ag $3d_{5/2}$ line, these conditions produce full width at half-maximum of better than 0.98 eV. Although the binding energy (BE) scale was calibrated using the Cu $2p_{3/2}$ feature at 932.62∓0.05 eV and Au 4f feature at 83.96∓0.05 eV for known standards, both the Fe-doped and Co-doped $SnO_2$ surfaces experienced variable degrees of charging. Low-energy electrons at ~1 eV, 21 μA, and low-energy $Ar^+$ ions were used to minimize this charging. The BE positions were referenced using the 486.7 eV position for the Sn $3d_{5/2}$ feature for the $Sn_{1-x}Fe_xO_2$ samples and for the $Sn_{1-x}Co_xO_2$ samples, and the 486.9 eV position for the $Sn_{1-x}Fe_xO$ samples. XPS spectra were also collected after $Ar^+$ ion sputtering using a 4 kV $Ar^+$ ion beam rastered over a 4 mm×4 mm sample area. The sputter rates were calibrated using a $SiO_2$ standard with known thickness.

Figure 15:
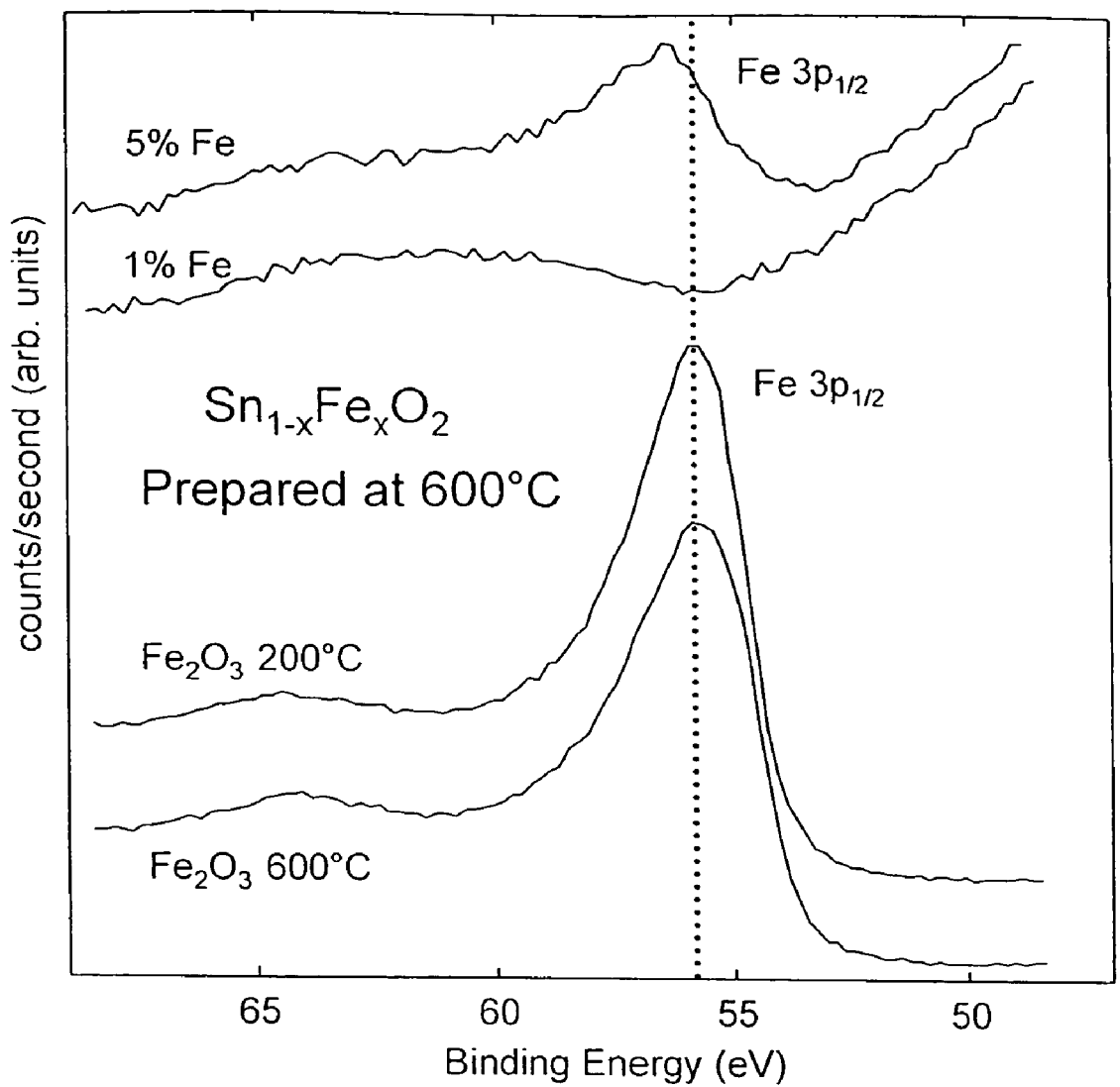
FIG. 15 shows XPS spectra of $Sn_{1-x}Fe_xO_2$ prepared at 600° C. with different values of x as indicated. Reference data obtained from maghemite and hematite forms of $Fe_2O_3$ prepared under identical synthesis conditions (but with no Sn precursors) are also shown.
Figure 16:
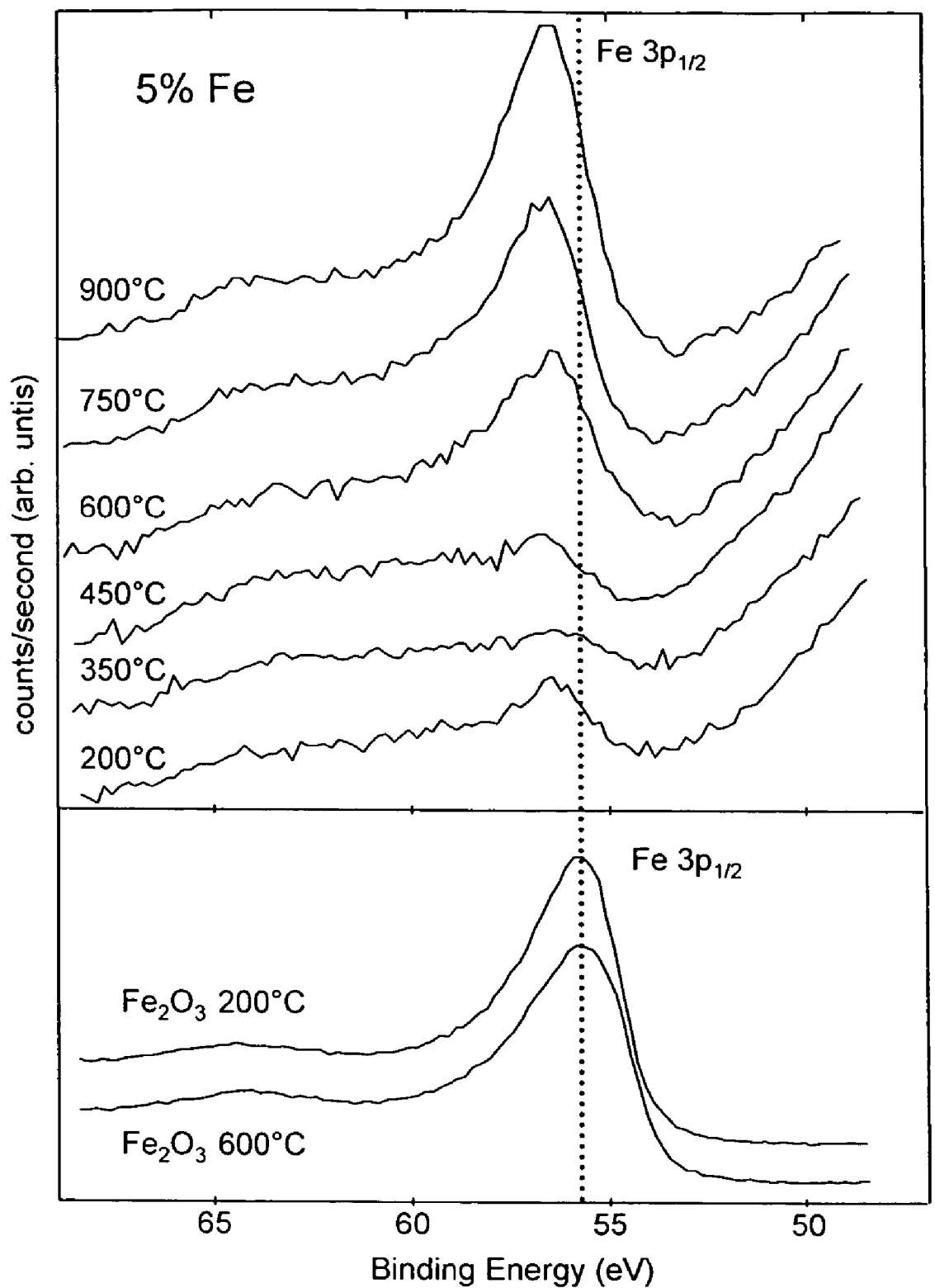
FIG. 16 is a plot showing the XPS spectra of 5% Fe-doped samples as a function of the annealing temperature. Reference data obtained from maghemite and hematite forms of $Fe_2O_3$ prepared at 200 and 600° C., respectively, under identical synthesis conditions (but with no Sn precursors) are also shown.

The Fe $3p_{1/2}$ XPS spectral region of $Sn_{1-x}Fe_xO_2$ (prepared by annealing the precipitate at 600° C.) samples with x=0.01 and 0.05 are shown in FIG. 15. Similar data obtained from hematite and maghemite phases of pure $Fe_2O_3$ prepared under identical conditions are also shown for comparison. The XPS peaks are not clearly visible in the 1% Fe-doped samples; however, clear peaks were observed in $Sn_{0.95}Fe_{0.05}O_2$. This discrepancy may be related to the limited Fe detection ability of the XPS system. The XPS peaks of both hematite and maghemite phases occur at ~55.7 eV, which matches well with literature reports. However, the core level peak of Fe in $Sn_{1-x}Fe_xO_2$, as shown in FIG. 15, and $Sn_{1-x}Fe_xO$, as shown in FIG. 16, 200° C. data, showed a slight shift to higher binding energies (~56.5 eV) compared to the Fe oxides, indicating the difference in the atomic environment surrounding the incorporated Fe ions. Fe $3p_{1/2}$ has a reported binding energy of 53.9 eV for the magnetite ($Fe_3O_4$) form of iron oxide. Thus, the XPS data clearly suggest that the Fe peaks observed from the $Sn_{1-x}Fe_xO_2$ and $Sn_{1-x}Fe_xO$ samples are not arising from any maghemite, hematite, or magnetite inclusions in the samples. The relative peak positions of the Sn and O peaks in the samples did not show any measurable change with Fe concentration, suggesting that their chemical environments did not change significantly. Atomic percentages of Sn, Fe, and O calculated using the Sn $3d_{5/2}$, Fe $3p_{1/2}$, and O 1s peaks are given in Table 1.

FIG. 16 shows the XPS data obtained from the $Sn_{1-x}Fe_xO$ and $Sn_{1-x}Fe_xO_2$ samples prepared by annealing the same reaction precipitate at 200, 350, 450, 600, 750, and 900° C. In all these samples, the core level Fe peak was observed at ~56.5 eV and no measurable shifts towards the binding energies expected for magnetite (53.9 eV), hematite (55.7 eV), and maghemite (55.7 eV) were observed when the preparation temperature varied in the 350 to 900° C. range. Although the Fe doping concentration was 5%, the Fe XPS peaks systematically intensified with increasing preparation temperature. Atomic percentages of Sn, Fe, and O, calculated using the XPS peaks as a function of preparation temperature, are given in Table I. Notwithstanding the difference between the atomic concentrations obtained from PIXE and XPS, the XPS estimates from $Sn_{0.95}Fe_{0.05}O_2$ showed a systematic increase in the Fe concentration from 0.7% to 6.2% as the annealing temperature increased from 350 to 900° C. As mentioned above, the lower Fe estimates from the XPS data may be due to the relatively lower detectability of Fe using XPS. In the PIXE measurements discussed above, the Fe concentration of the $Sn_{1-x}Fe_xO_2$ samples prepared in the entire temperature range was always between 4% and 4.88%, and no systematic variation with preparation temperature was observed. Compared to PIXE, which is responsive to the entire bulk of the sample, XPS is a surface-sensitive technique. Therefore, the increasing differences between the Fe concentrations obtained from these two techniques clearly suggest a gradual and systematic surface diffusion of the doped Fe ions with increasing preparation temperature. This suggests that the $Sn_{1-x}Fe_xO_2$ samples prepared at lower temperature produce a more uniform distribution of Fe in the entire crystallite. On the other hand, samples prepared at higher temperatures showed significant diffusion of the incorporated Fe ions towards the particle surface as preparation temperature increases to 900° C.

Figure 17:
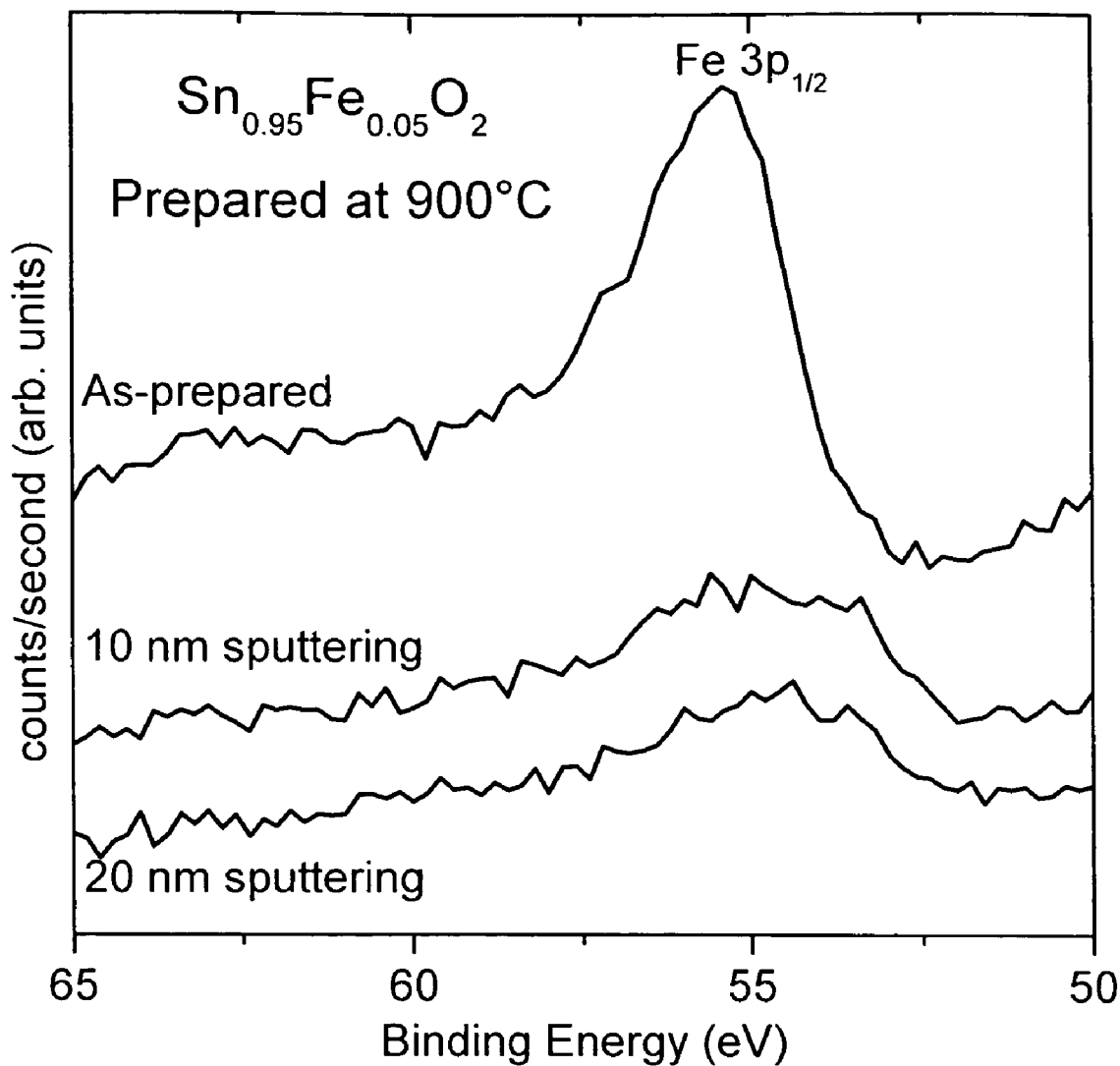
FIG. 17 is a plot showing the XPS spectra of $Sn_{0.95}Fe_{0.05}O_2$ prepared at 900° C. along with that obtained from the same sample after removing 10 and 20 nm of surface layer by $Ar^+$ ion sputtering.

To further confirm the Fe surface diffusion possibility, XPS spectra were collected from the 900° C. prepared $Sn_{1-x}Fe_xO_2$ sample employing $Ar^+$ ion sputtering to remove surface layers from the powder samples mounted on carbon conductive tape, as shown in FIG. 17. These measurements showed a gradual decrease in the Fe concentration from 6.23% in the as-prepared sample to 3.43% when a 20 nm surface layer is removed by $Ar^+$ ion sputtering (see Table I). This fully supports the above conclusion that the higher XPS estimates of Fe concentration obtained from $Sn_{1-x}Fe_xO_2$ samples prepared at higher temperatures (≧600° C.) are indeed due to Fe surface diffusion.

Figures 18A, 18B:
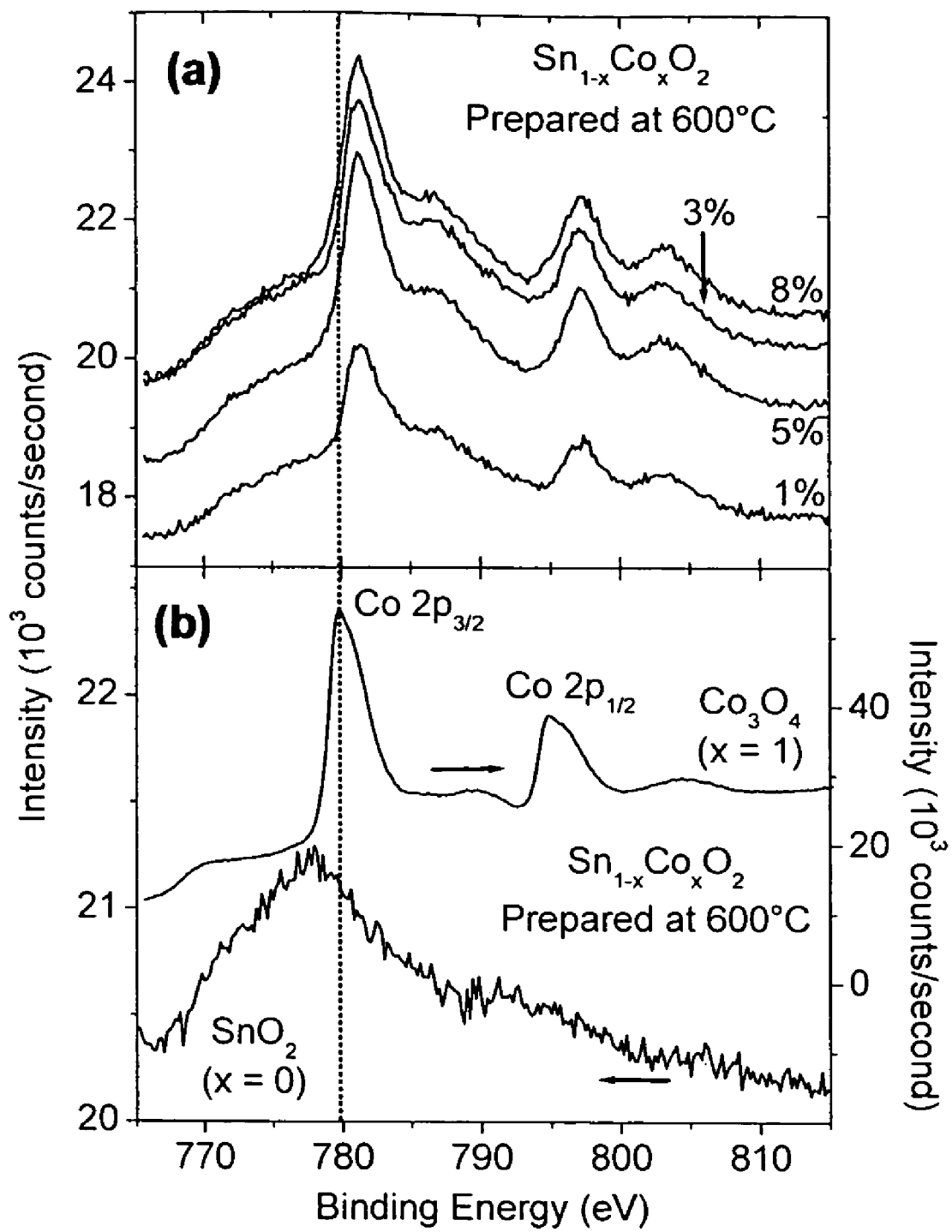
FIGS. 18 (a) and (b) show (a) XPS spectra of $Sn_{1-x}Co_xO_2$ prepared at 600° C. as a function of Co percentage and (b) shows similar data of $Co_3O_4$ (x=1) and $SnO_2$ (x=0) reference samples prepared under identical synthesis conditions.

The Co $2p_{3/2}$ and Co $2p_{1/2}$ XPS spectral region of the $Sn_{1-x}Co_xO_2$ samples are shown in FIG. 18. Comparing the binding energies of the Co primary and satellite XPS peaks with that observed for Co(0) in Co metal, $Co^{2+}$ in CoO and $Co^{3+}$ in δ-$Co_2O_3$, the electronic state of Co in $Sn_{1-x}Co_xO_2$ samples is found to be $Co^{2+}$ and that it is not bonded to oxygen as CoO or $Co_3O_4$. It also rules out any metallic Co clusters in the samples, a result well expected for chemically synthesized samples prepared and processed in air. These results agree well with the 2+ oxidation state of Co with S=3/2 determined from magnetization measurements of paramagnetic samples of $Sn_{1-x}Co_xO_2$. The ≧1 eV shift of the Co $2p_{3/2}$ peak in the $Sn_{1-x}Co_xO_2$ samples compared to that observed from the $Co_3O_4$ reference sample suggests that Co is indeed incorporated in the $SnO_2$ lattice and not forming any significant amount of Co oxides. However, no significant change in the Co binding energy is observed with increasing Co doping concentration. Careful analysis of the peak positions of the Sn $3d_{5/2}$ (486.7 eV) and O 1s (530.65 eV) peaks also did not show any noticeable change in the binding energy with increasing Co concentration.

Figures 19A, 19B:
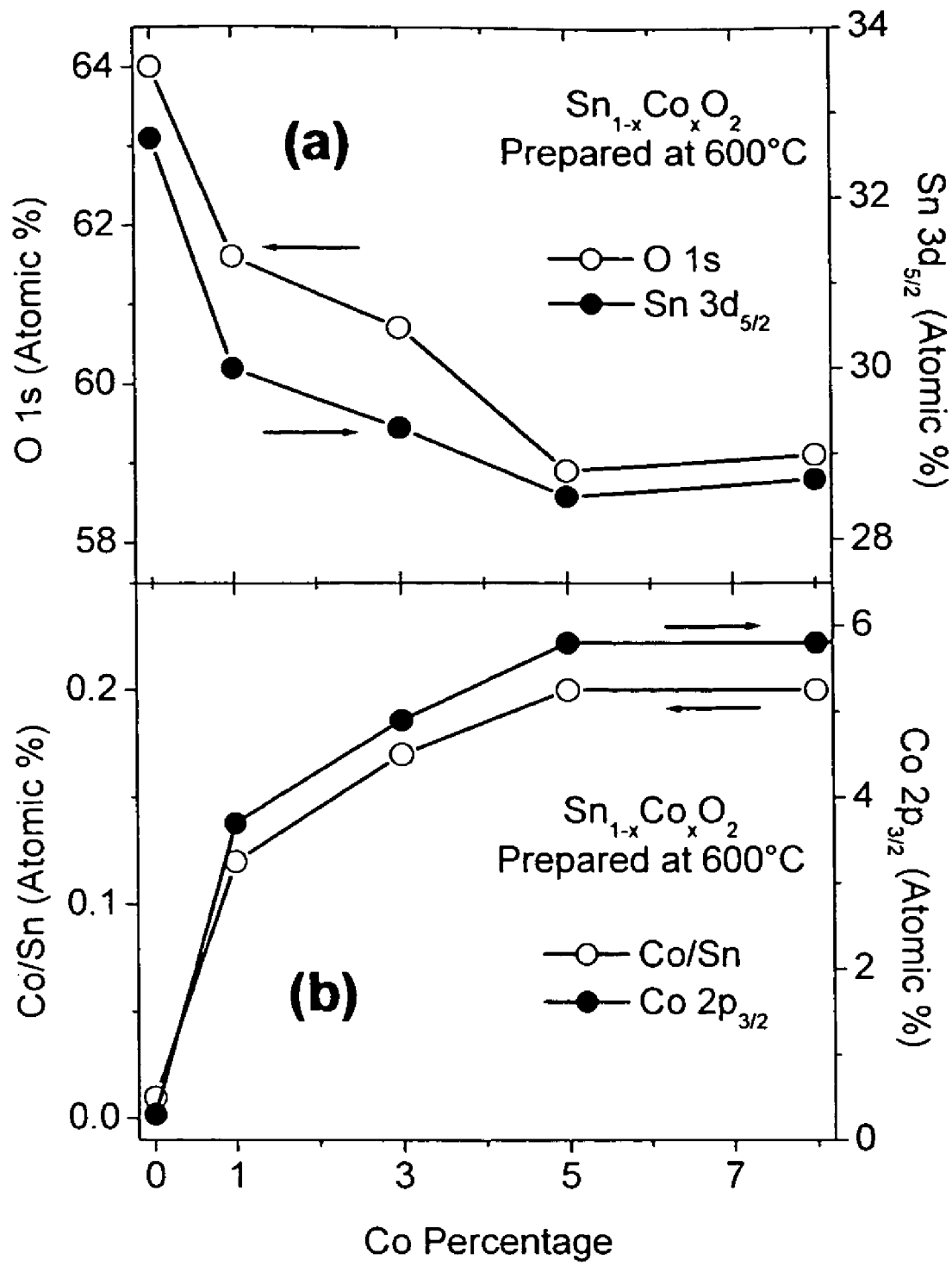
FIGS. 19 (a) and (b) show the variation of the atomic percentages of Co, Sn, and 0 and the Co/Sn ratio as a function of Co concentration calculated using the corresponding XPS peak intensities.

Atomic percentages of Sn, Co, and O calculated using the Sn $3d_{5/2}$ (486.7 eV), O 1s (530.65 eV), and Co $2p_{3/2}$ (781.4 eV) peaks are shown in FIG. 19. In these plots, three well defined regions are present. A rapid increase in the atomic percentage of Co and the Co/Sn ratio, and a decrease in the Sn atomic percentage for x≦0.01, indicate substitutional incorporation of Co at Sn sites. In the 0.01≦x≦0.05 range, a relatively slower variation is observed suggesting more interstitial incorporation and/or $Co_3O_4$ precipitation in agreement with results from XRD, Raman, and optical studies, discussed above. In the case of substitutional Co incorporation, Co ions remove Sn ions from the $SnO_2$ structure. However, in the case of interstitial incorporation or $Co_3O_4$ precipitation, there is no Sn removal. For x>0.05, changes in the Co/Sn atomic percentage ratio are minimal, indicating lack of further Co incorporation into the $SnO_2$ lattice. Estimation of the oxygen content in the samples using the O 1s (530.65 eV) peak indicated almost stoichiometric Sn/O ratio for the undoped sample. Co doping decreases the oxygen content of the sample, as shown in FIG. 19(a). Removal of oxygen atoms from the $SnO_2$ lattice is well expected if $Co^{2+}$ replaces $Sn^{4+}$ ions due to charge neutrality requirements. It has been argued that substitutional $Co^{2+}$ and oxygen vacancies in excess of those necessary for charge neutrality are essential to produce ferromagnetism in $Ti_{1-x}Co_xO_2$. A rapid loss in oxygen content, indicated by relatively larger changes in the oxygen atomic percentage, for samples with x≦0.01 (FIG. 19(a)), may be crucial for the ferromagnetism observed only in this narrow Co percentage range of ≦1%.

3. Shown by Absence of Iron Oxide Phases in the $Sn_{1-x}Fe_xO_2$

The even distribution of Fe throughout the ferromagnetic $Sn_{1-x}Fe_xO_2$ powder has been shown by the absence of iron oxide phases in the samples. The origin of ferromagnetism in dilute magnetic semiconductor oxides has been extensively studied recently because of the possible presence of weaker secondary phases. This is particularly important when the ferromagnetic component is weak. The fact that the sol-gel preparation of the samples and their subsequent drying and annealing processes were all conducted in air intrinsically eliminates the possibility of forming metallic Fe particles.

The possibility was investigated that the ferromagnetism observed in $Sn_{1-x}Fe_xO_2$, when prepared in the 350 to 600° C. range, may be due to weak traces of maghemite or magnetite phases of iron oxide formed in the sample. The pure iron oxide samples prepared under identical synthesis conditions showed the formation of pure maghemite when prepared at 200° C. and pure hematite at 600° C. However, no ferromagnetism was observed in the $Sn_{1-x}Fe_xO$ sample prepared by annealing the precipitate at 200° C., which rules out the presence of any maghemite phase undetected in the XRD data. Therefore, it is unlikely that this phase will appear when the $Sn_{1-x}Fe_xO_2$ sample is prepared by annealing the same precipitate in the 350 to 600° C. range. Investigation of the phase transition of pure iron oxide samples prepared under identical conditions showed that the maghemite phase converted to the hematite phase when annealed at temperatures above 350° C. Thus, it is very unlikely that the maghemite phase of iron oxide is present in the $Sn_{1-x}Fe_xO_2$ samples prepared by annealing at temperatures ≧350° C.

Figures 20A, 20B, 20C:
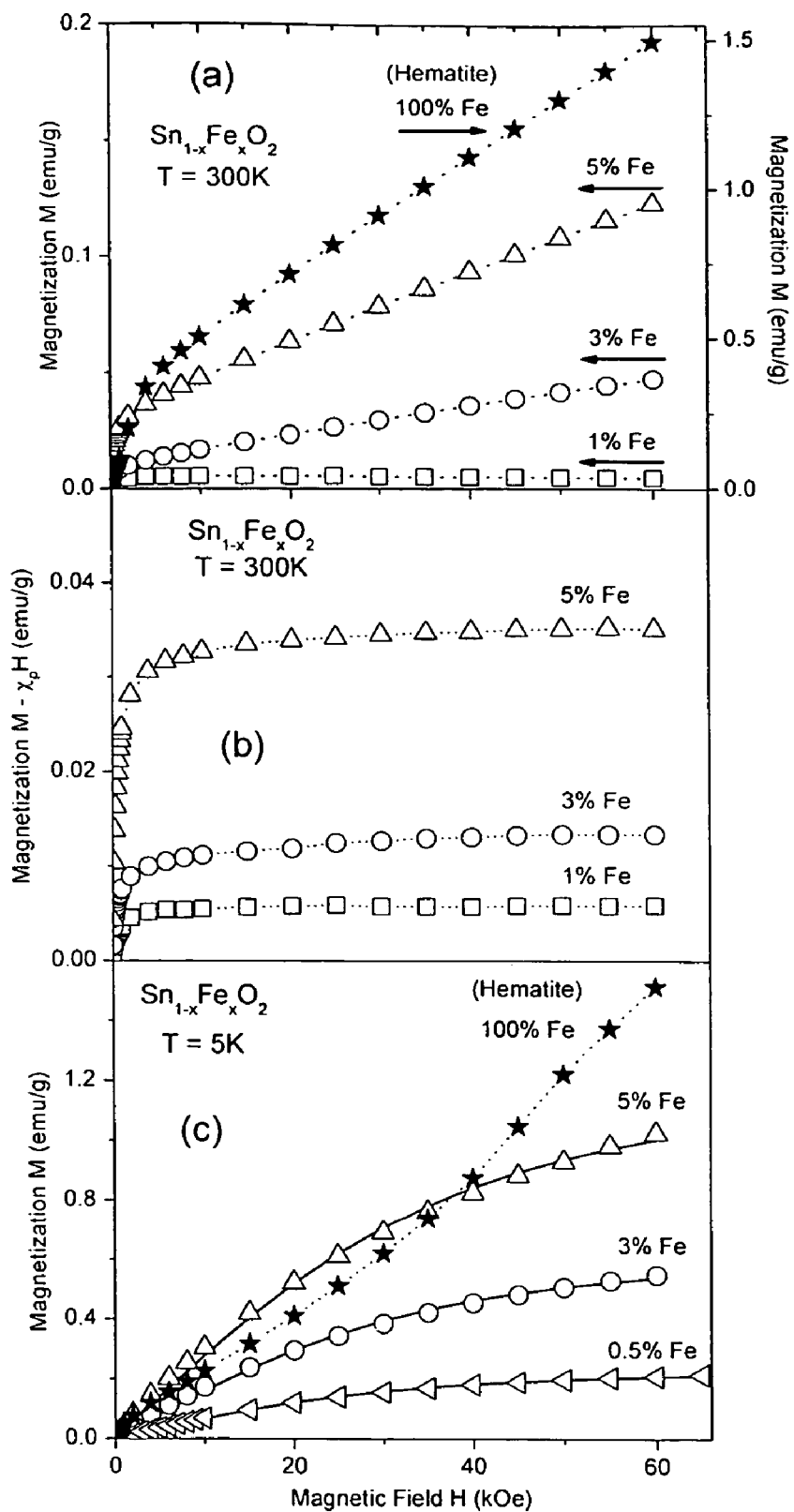
FIGS. 20 (a)-(c) show (a) and (c) M vs H data of $Sn_{1-x}Fe_xO_2$ measured at 300 and 5K, respectively; (b) M-$\chi_p$H as a function of H for the $Sn_{1-x}Fe_xO_2$ samples measured at 300K. Solid lines through the data points in (c) are theoretical fits using the modified Brillouin function for a paramagnetic system.
Figure 21:
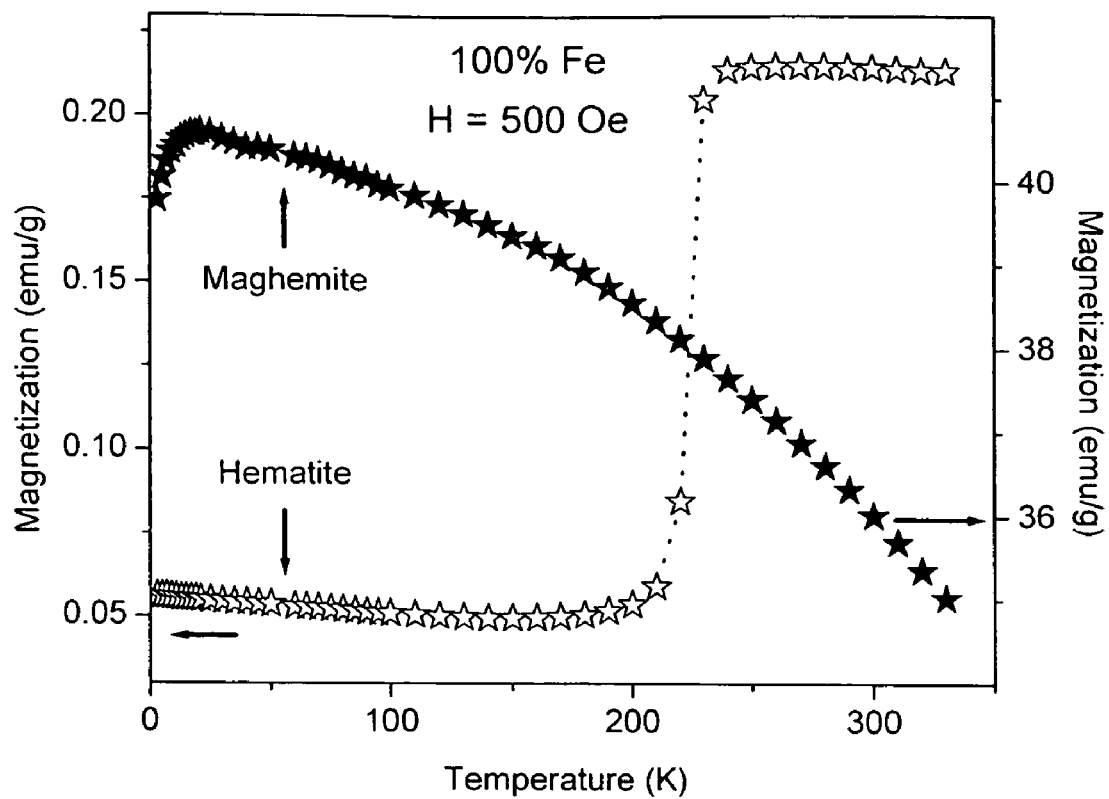
FIG. 21 shows M vs T data measured with H=500 Oe for pure iron oxide samples prepared at 200° C. (maghemite) and 600° C. (hematite).
Figure 22:
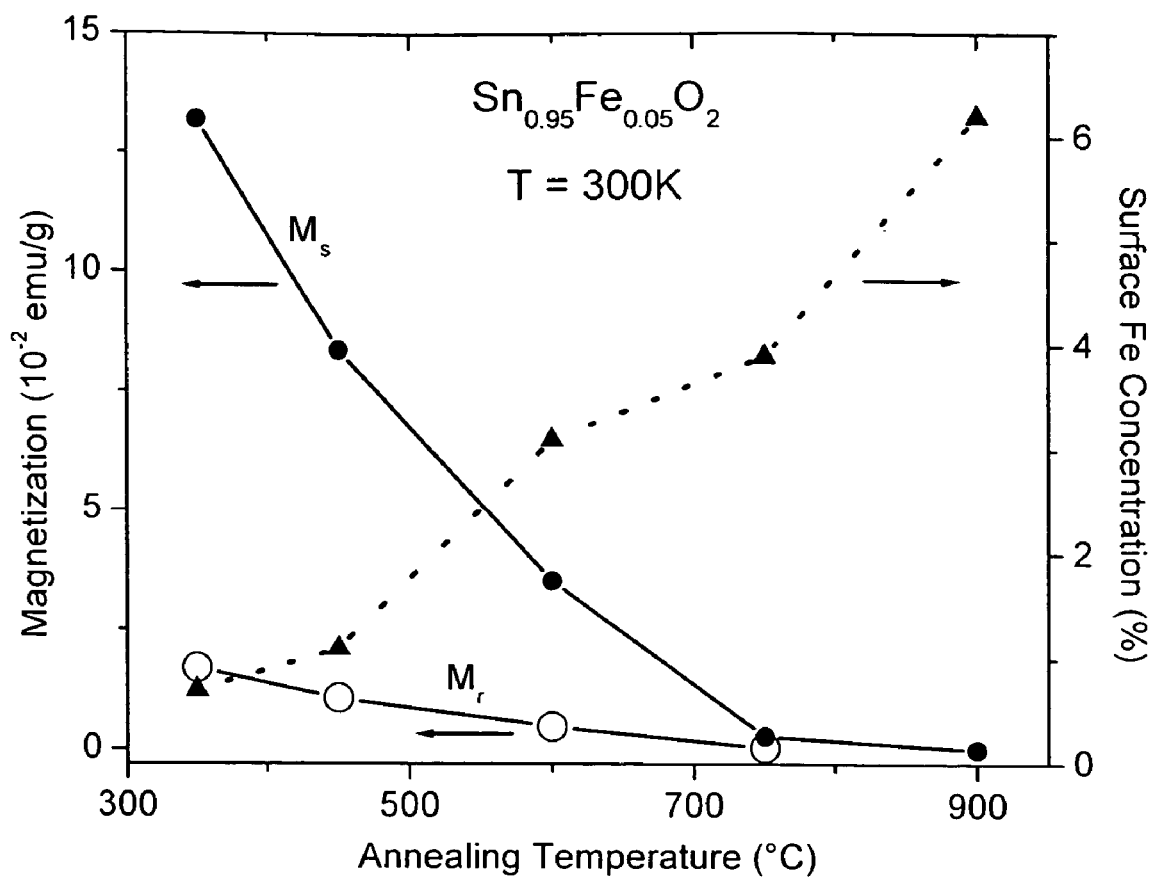
FIG. 22 shows changes in the saturation magnetization $M_s$ and remanence $M_r$, along with the XPS estimate of surface Fe concentration of the $Sn_{0.95}Fe_{0.05}O_2$ samples as a function of their preparation temperature.

The M versus H data shown in FIG. 20(c), obtained from measuring $Sn_{1-x}Fe_xO_2$ at 5 K, and M versus T data shown in FIG. 21, obtained from measuring pure iron oxide samples prepared at 200° C. and 600° C. with an applied magnetic field H=500 Oe, ruled out the presence of hematite due to the absence of spin-flop and the strong Morin transitions. The hematite phase is thermally the most stable phase and it undergoes a thermal reduction to the magnetite ($Fe_3O_4$) phase only above 1200° C. Thus, thermodynamically, the possible formation of the magnetite phase can also be ruled out. Even if the magnetite phase were formed, the observed disappearance of ferromagnetism when prepared at temperatures above 600° C., as shown in FIG. 22, would be difficult to understand.

Further, careful analysis of the samples using XRD, TEM, and selected area diffractions experiments has ruled out the presence of any iron oxide phases in the $Sn_{1-x}Fe_xO_2$ samples. Finally, the Mossbauer data, XPS spectra, and hysteresis loop parameters obtained from the $Sn_{1-x}Fe_xO_2$ samples clearly ruled out the presence of any bulk or nanoscale magnetite, hematite, maghemite, or goethite phases of iron oxide in the samples.

Figures 23A, 23B:
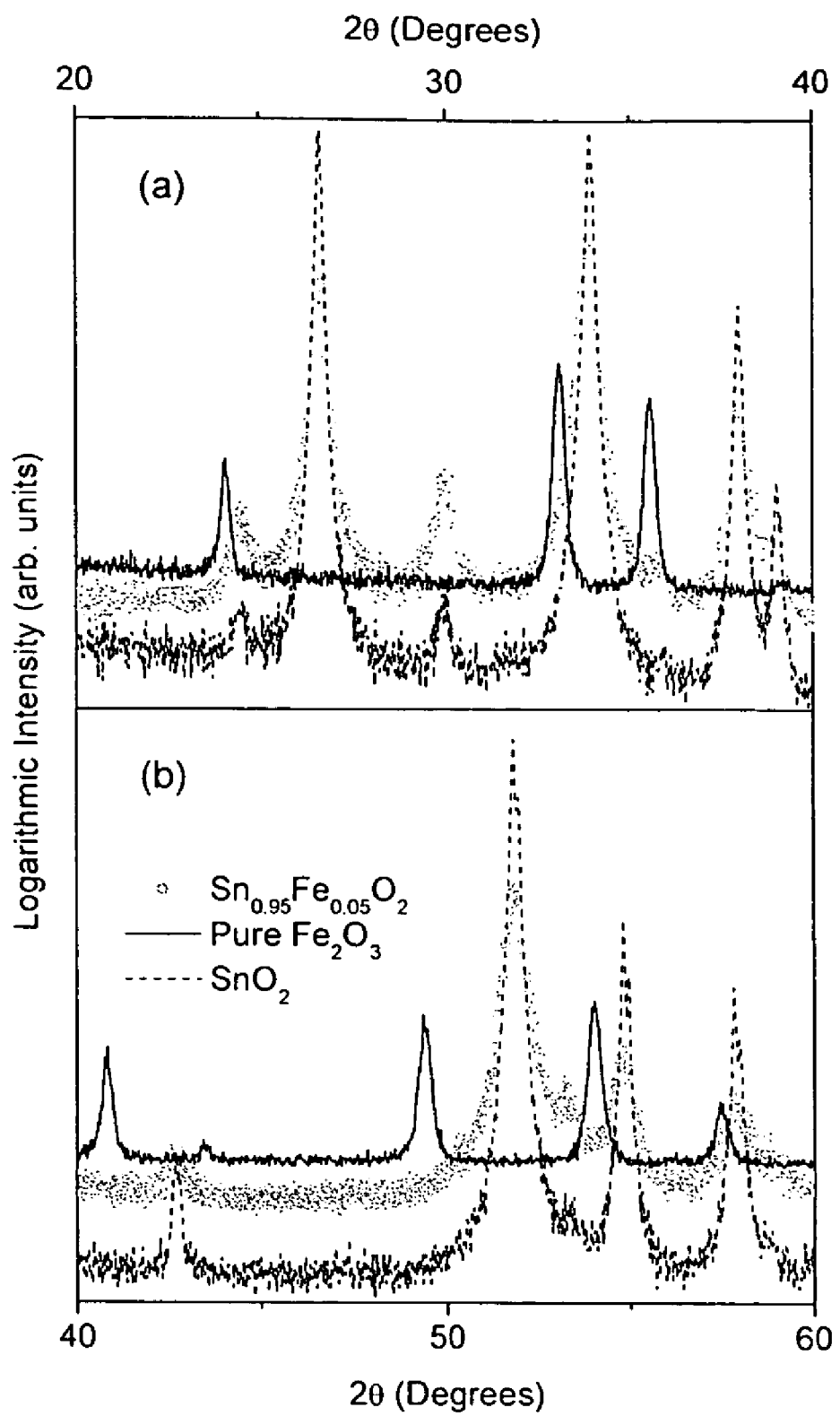
FIGS. 23 (a) and (b) show XRD data collected from separate angular regions for $Sn_{0.95}Fe_{0.05}O_2$ (data points), pure $SnO_2$ (dashed line), and pure $Fe_2O_3$, all prepared at 600° C. following identical synthesis procedures. The intensity is plotted on a log scale.

Room-temperature ferromagnetism observed in a Mn-doped ZnO system has been shown to result from a metastable $Mn_{2-x}Zn_xO_3$-d type phase formed by the diffusion of Zn into Mn oxides. In these studies, peaks due to pure and/or doped manganese oxides were clearly observed in the XRD measurements (plotted on a log scale). In the present work, although the saturation magnetization increases by about four times as Fe concentration increases to 5%, no indication of pure or doped iron oxides or other impurities is observed in the XRD measurements (shown on log scale), as illustrated in FIG. 23. In the selected area electron diffraction, XPS, or Mossbauer spectroscopy studies as well, no evidence for the presence of any such mixed phases in $Sn_{1-x}Fe_xO_2$ in the entire ranges of Fe concentration and preparation temperatures were observed. The sol-gel-based chemical synthesis employed to manufacture the $Sn_{1-x}Fe_xO_2$ is well known to provide a uniform distribution of the dopant in the host system at lower temperatures, as compared to the solid state reaction used in the preparation of Mn-doped ZnO.

4. Incorporation of Fe into the $SnO_2$ and SnO Lattices

The systematic changes in the lattice parameters, particle size, and shape observed in XRD and TEM studies strongly support the progressive incorporation of Fe into the $SnO_2$ and SnO lattices with increasing x. The one-to-one match in the relative changes in the saturation magnetization M, and lattice volume V, shown in FIG. 24, observed in the $Sn_{1-x}Fe_xO_2$ samples, is very strong evidence against any impurity being the origin of the observed ferromagnetism. The one-to-one match also suggests a strong structure-magnetic property relationship in these samples. The striking agreement between the estimated magnetically ordered $Fe^{3+}$ spins (~24%) in the powder samples of $Sn_{0.95}Fe_{0.05}O_2$ and a similar estimate of ferromagnetic $Fe^{3+}$ spins (~23%) in pulsed-laser-deposited thin films of $Sn_{0.95}Fe_{0.05}O_2$ further supports the conclusion that the observed ferromagnetism in $Sn_{1-x}Fe_xO_2$ is not due to impurity iron oxide phases formed under the different preparation conditions employed.

The conclusion that the Fe is incorporated into the $SnO_2$ and SnO lattices is also supported by the role of the host system. It is well known that the p-type semiconducting behavior SnO results from an excess of oxygen, whereas the existence of oxygen vacancies in $SnO_2$ make it an excellent n-type semiconductor. The XPS data obtained for 1% and 5% Fe-doped SnO showed identical oxygen atomic percentages (see Table I), whereas the oxygen concentration decreased in $Sn_{1-x}Fe_xO_2$ with Fe concentration. The Sn—O distance of 2.057 Å in $SnO_2$ is lower than the 2.223 Å in SnO, and this might influence the overlap of the electron orbitals. Thus, in $Sn_{1-x}Fe_xO$, Fe doping might favor the formation of antiferromagnetic $Fe^{3+}$—$O^{2-}$—$Fe^{3+}$ groups, whereas $Sn_{1-x}Fe_xO_2$ will have a large number of ferromagnetic $Fe^{3+}$-[oxygen vacancies]-$Fe^{3+}$ groups because of the oxygen vacancies. This might explain the observed antiferromagnetic interaction in $Sn_{1-x}Fe_xO$ and ferromagnetism in $Sn_{1-x}Fe_xO_2$.

Figures 24A, 24B, 24C:
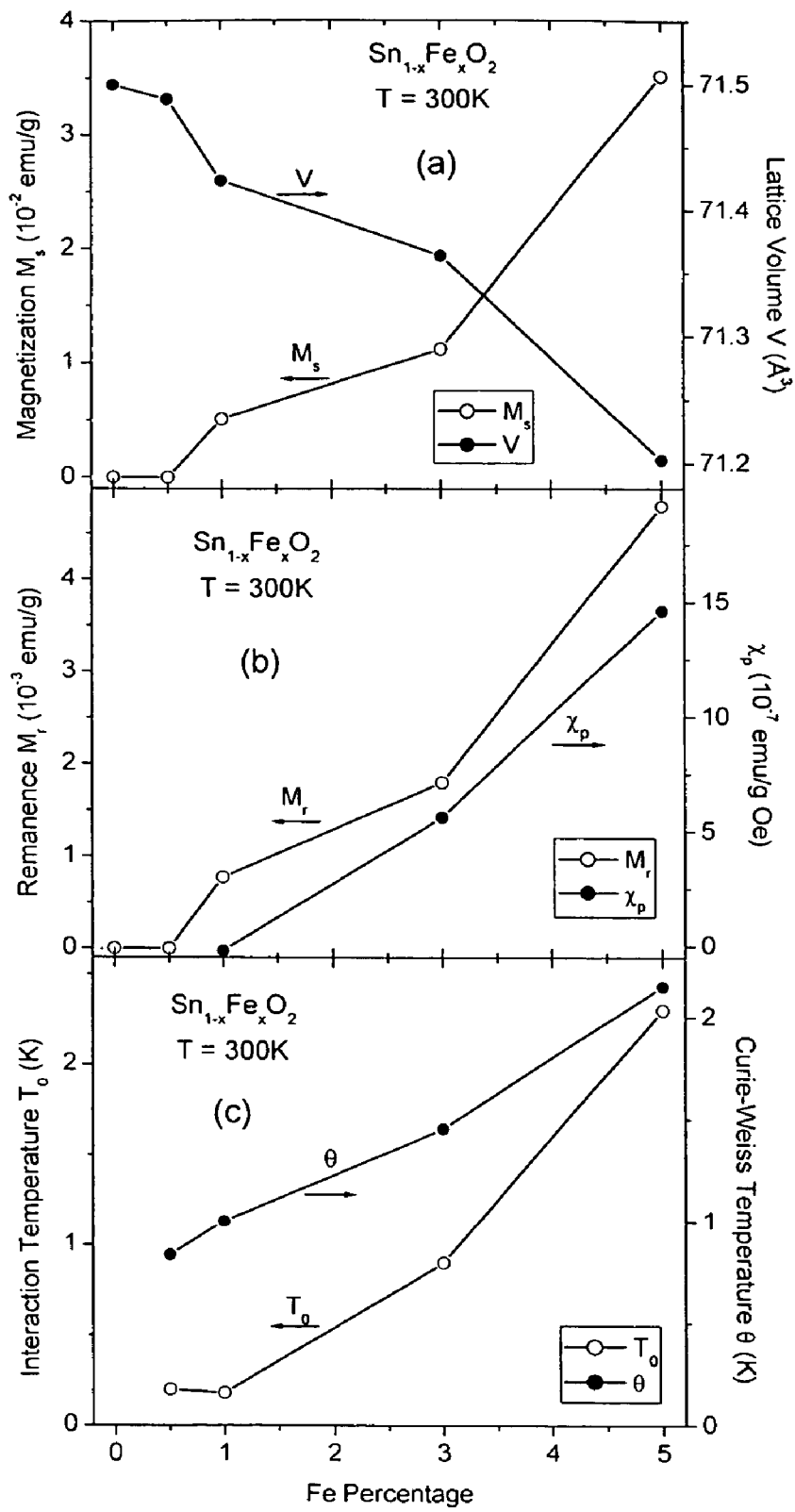
FIGS. 24 (a)-(c) show changes in (a) saturation magnetization $M_s$ and lattice volume V, (b) remanence $M_r$ and the linear paramagnetic component $\chi_p$, and (c) interaction parameter $T_0$ and Curie-Weiss temperature θ (obtained from the paramagnetic component in FIG. 25) of the $Sn_{1-x}Fe_xO$ samples as a function of x.

The $Sn_{1-x}Fe_xO_2$ composition showed a strong structure-magnetic property relationship, as shown in FIG. 24(a), where the increase in the saturation magnetization with Fe concentration matches with the increase in the lattice concentration. $Sn_{1-x}Fe_xO$, on the other hand, showed an expansion of the lattice with increasing Fe concentration, and here no ferromagnetism is observed. Changes in the internal or external lattice volume/pressure have been reported to produce ferromagnetism in itinerant electron metamagnets. Thus, more investigation is required to understand the exact role of structural changes and internal pressure differences in the observed ferromagnetism/paramagnetism of $Sn_{1-x}Fe_2O_2$/$Sn_{1-x}Fe_xO$.

F. Magnetic Properties of the Compositions

The $Sn_{1-x}Fe_xO_2$ showed ferromagnetic behavior with a Curie temperature of up to 850 K, well above room-temperature, for the 1% Fe-doped sample. All of the $Sn_{1-x}Fe_xO_2$ samples show well-defined hysteresis loops at 300 K, room-temperature, with remanence $M_r$ and saturation magnetization $M_s$ increasing gradually with the level of Fe-doping. The ferromagnetic property is stronger when prepared at lower annealing temperatures, and it gradually declines with increasing preparation temperature and eventually disappears completely for preparation temperatures greater than 600° C. In the preferred embodiment, the $Sn_{1-x}Fe_xO_2$ powder is free of any hematite particles.

Magnetic measurements for both $Sn_{1-x}Fe_xO_2$ and $Sn_{1-x}Co_xO_2$ were carried out as a function of temperature (4 to 350 K) and magnetic field (0 to ~65 kOe) using a commercial magnetometer (Quantum Design, PPMS) equipped with a superconducting magnet. Measurements were carried out on tightly packed powder samples placed in a clear plastic drinking straw. The data reported were corrected for the background signal from the sample holder (clear plastic drinking straw) with diamagnetic susceptibility $\chi=-4.1\times10^{-8}$ emu/Oe.

1. Iron Concentration Dependence
   a. $Sn_{1-x}Fe_2O_2$

Figure 25:
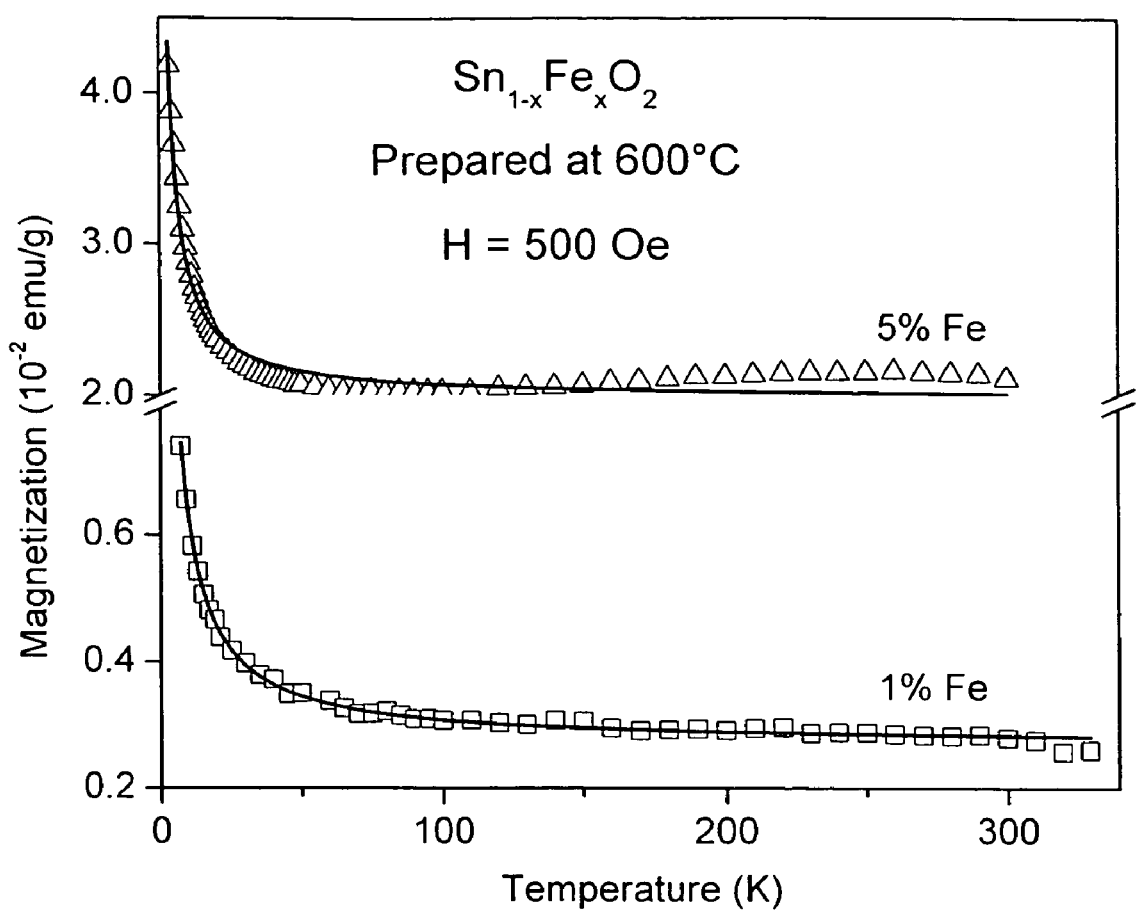
FIG. 25 shows M vs T data measure with H=500 Oe from $Sn_{1-x}Fe_xO_2$ samples. Solid lines are theoretical fits using the modified Curie-Weiss law.
Figure 26:
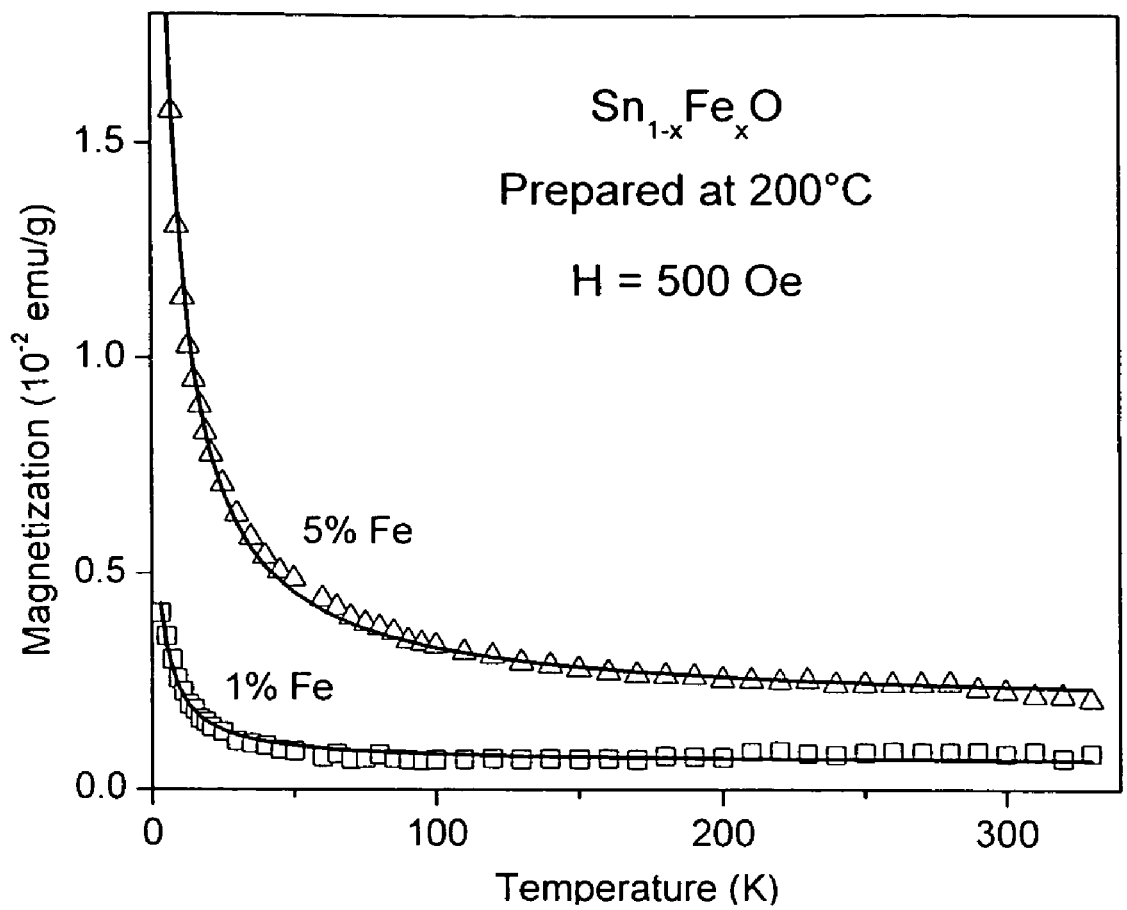
FIG. 26 shows M vs T data measured with H=500 Oe from $Sn_{1-x}Fe_xO$ samples. Solid lines are theoretical fits using the modified Curie-Weiss law.

The room-temperature M versus H data of $Sn_{1-x}Fe_xO_2$, shown in FIG. 20(a), show a linear component superimposed on a saturating ferromagnetic-like magnetization. If this linear component $\chi_p$ is subtracted, the M-$\chi_p$ data show saturation of M expected for a ferromagnetic phase, as shown in FIG. 20(b). FIG. 20(c) shows that at 5 K, the ferromagnetic component is overwhelmed by a paramagnetic-like component. Variations of the saturation magnetization $M_s$ and $\chi_p$ obtained from the M versus H data as a function of the Fe-doping are shown in FIGS. 24(a) and 24(b). These data fit reasonably well with the modified Brillouin function, assuming that J=5/2. This indicates that a fraction of the doped Fe is not participating in the ordered magnetic state, in excellent agreement with the Mossbauer results previously shown in FIG. 14(b). The exact nature of this component becomes more evident from the M versus T data shown in FIG. 25. This showed a paramagnetic variation described by the modified Curie-Weiss law similar to their $Sn_{1-x}Fe_xO$ counterparts as shown in FIG. 26, but offset by an amount $\chi_0$; this offset is most likely due to the ferromagnetic component. This also confirms that the linear component $\chi_p$ observed in the room-temperature M versus H data shown in FIG. 20(a) is also due to this paramagnetic contribution present in the sample. $T_0$ and $\theta$ data, shown in FIG. 24(c), obtained from the M versus H and M versus T data respectively, indicate that the interaction between the disordered (paramagnetic-like) $Fe^{3+}$ spins present in $Sn_{1-x}Fe_xO_2$ is antiferromagnetic (AF) in nature.

Figure 27:
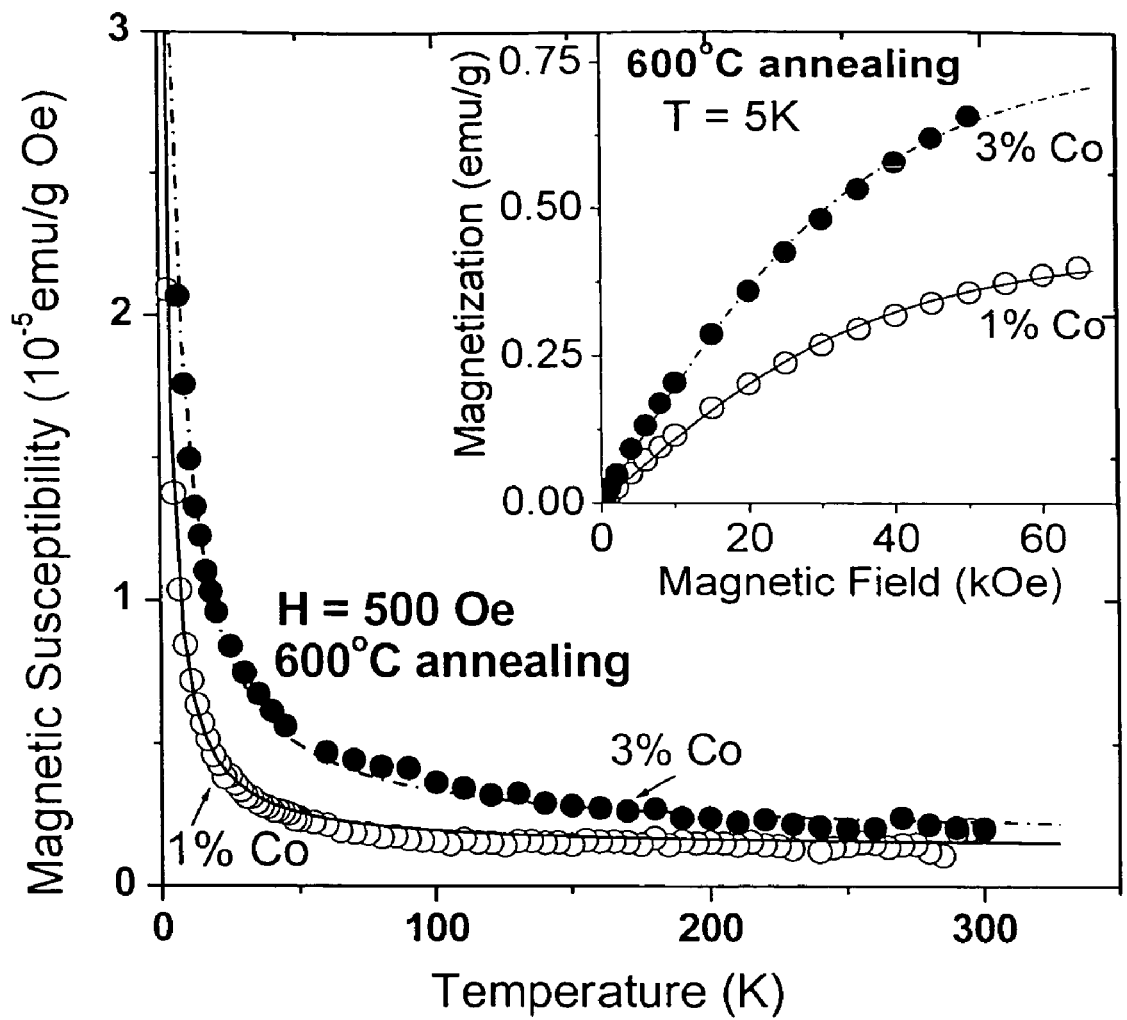
FIG. 27 shows temperature variations of the magnetic susceptibility χ, measured with an applied field H=500 Oe, for the 1% and 3% Co doped samples prepared at 600° C. Lines through the data points are theoretical fits using the modified Curie-Weiss law. The inset shows the magnetization of the same samples, measured at 5K as a function of magnetic field. Lines through the data points are theoretical fits using the Brillouin-function-based form for a paramagnetic system.

Measurements of the sample magnetization M as a function of magnetic field H and temperature T were carried out using a commercial magnetometer (Quantum Design, PPMS) equipped with a superconducting magnet. The data reported were corrected for the background signal from the sample holder. In the inset of FIG. 27, M vs. H plots of $Sn_{1-x}Co_xO_2$ samples (with x=0.01 and 0.03) prepared at 600° C. and measured at 5K are shown along with their theoretical estimates obtained using the Brillouin-function-based form for a paramagnetic system, given by $$M=M_0\{[(2J+1)/2J]\coth[(2J+1)y/(2J)]-(1/2J)\coth(y/2J)\}$$

Where $y=(g\mu_BJH)/(kT)$, $M_0$ is the saturation magnetization, g is the spectroscopic splitting factor (g=2.0023 for free electrons), $\mu_B$ is the Bohr magneton and k is the Boltzmann constant. M vs. H data of the $Sn_{1-x}Co_xO_2$ samples fit very well with their theoretical estimates yielding a total angular momentum J=1.81±0.1. These values are in good agreement with experimental magnitudes (~4.8) reported for paramagnetic $Co^{2+}$ ions with spin S=3/2 [13].

Magnetic susceptibility $\chi=M/H$ of the samples measured as a function of temperature at a constant H=500 Oe also showed the expected paramagnetic behavior. In FIG. 27, X vs. T data of the 1 and 3% Co doped samples are shown along with theoretical fits obtained using the modified Curie-Weiss law $$X=X_0+[C/(T+\theta)]$$

Where $X_0=1.5(0.2)\times10^{-6}$ emu/g Oe represents weak non-paramagnetic contribution, Curie constant $C=N\mu^2/3k$ is a measure of the paramagnetic ion concentration (N=number of magnetic ions/g, μ=magnetic moment of the ion) and θ is the Curie-Weiss temperature which represents the magnetic exchange interactions between the spins. These fits yield θ=0.18 and 1.55K, and $C=0.63\times10^{-4}$ and $1.6\times10^{-4}$ emu K/g Oe for x=0.01 and 0.03 respectively.

The pure hematite form of iron oxide, prepared at 600° C. following an identical synthesis procedure but with no Sn precursor, showed a weak magnetization, as shown in FIGS. 20(a), 20(c), and 21. The most striking characteristics of bulk hematite include the sharp Morin transition near 263 K in the M versus T data and a spin-flop (SF) transition at $H_{SF}$ ~67.5 kOe in the M versus H data. Both of these transitions were indeed present in our pure hematite as shown in FIGS. 20(a) and 21, albeit with reduced magnitudes which are presumably due to a smaller particle size of ~53 nm. These transitions were clearly absent in all of the $Sn_{1-x}Fe_xO_2$ samples, ruling out the presence of any hematite particles.

Figure 28:
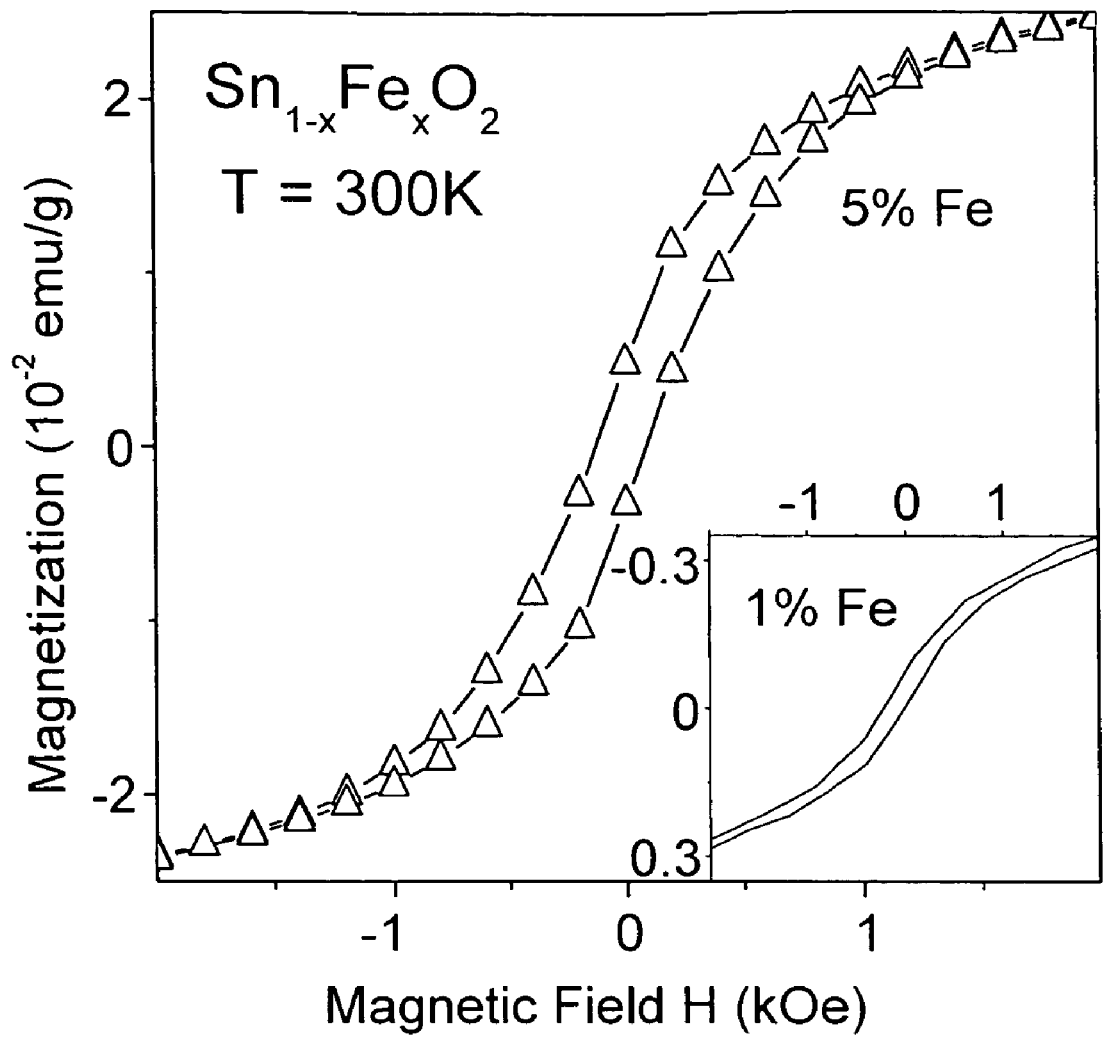
FIG. 28 shows room-temperature hysteresis loops of $Sn_{1-x}Fe_xO_2$ prepared at 600° C. with x=0.05 (main panel) and 0.01 (inset). The lines joining the points are for visual aid.
Figure 29:
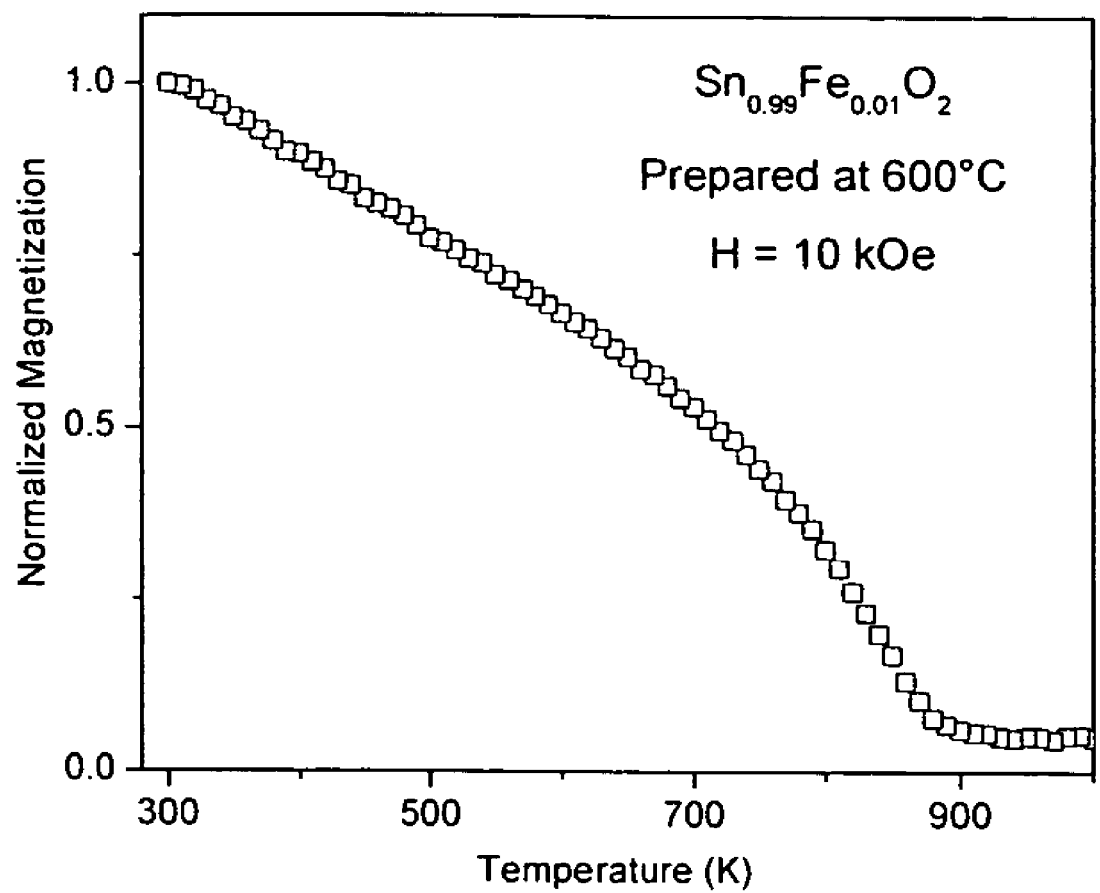
FIG. 29 is a plot of the normalized sample magnetization M of a $Sn_{0.99}Fe_{0.01}O_2$ sample measured with H=10 kOe as a function of temperature, indicating a Curie temperature $T_C$ ~850K.

The $Sn_{1-x}Fe_xO_2$ samples showed well defined hysteresis loops at 300 K, as shown in FIG. 28, with remanence $M_r$ and saturation magnetization $M_s$ increasing gradually with the percentage of Fe-doping, as shown in FIGS. 24(a) and 24(b). The coercivity $H_c$ was in the range of 60 Oe, which is significantly different from the value of $H_c=1844$ Oe obtained for the pure hematite sample prepared under identical conditions. The existence of a significant coercivity in $Sn_{1-x}Fe_xO_2$ samples clearly rules out their possible origin from nanoscale superparamagnetic particles of iron oxides because when magnetic materials are prepared in nanoscale sizes, they demonstrate superparamagnetic behavior characterized by hysteresis loops with zero coercivity above their blocking temperatures. Absence of bulk iron oxides (or nonsuperparamagnetic particles) was confirmed from the Mossbauer data discussed above. Finally, a Curie temperature $T_c=850$ K was obtained for the 1% Fe-doped $SnO_2$ sample by measuring M up to 1000 K, as shown in FIG. 29. This Curie temperature is among the highest Curie temperatures reported for transition-metal-doped oxide semiconductors.

Some of the samples with 0.5 and 1% Co doping annealed at 600° C. showed a ferromagnetic behavior. In the inset (a) of FIG. 30, a hysteresis loop measured at 300 K from a 1% Co doped $SnO_2$ sample prepared by annealing the precipitate at 600° C. is shown. The magnetization saturates very well for H>3 kOe with a saturation magnitude of 0.133 $\mu_B$/Co ion. However, the data did not show any significant coercivity or remenance.

The systematic growth of both ferromagnetic and paramagnetic contributions in $Sn_{1-x}Fe_xO_2$ with increasing x, as shown in FIGS. 24(a) and 24(b), suggests that the ferromagnetic component is not growing at the expense of the paramagnetic $Fe^{3+}$ ions as Fe doping increases. Other researchers have proposed a ferromagnetic exchange mechanism involving oxygen vacancies, which form F-centers with trapped electrons, for the observed ferromagnetism in Fe-doped $SnO_2$ thin films. Overlap of the F-center electron orbitals with the d-orbitals of the neighboring $Fe^{3+}$ spins to form $Fe^{3+}$-[oxygen vacancies]-$Fe^{3+}$ groups is crucial for the proposed ferromagnetic coupling. It has been argued that doped $Fe^{3+}$ spins might also exist as isolated paramagnetic spin systems wherever the F-center mediated ferromagnetic coupling is not achieved due to lack of $Fe^{3+}$ neighbors and/or oxygen vacancies. In addition, any $Fe^{3+}$—$O^{2-}$—$Fe^{3+}$ superexchange interactions will be antiferromagnetic in nature. As Fe doping concentration increases, both ferromagnetic and paramagnetic/antiferromagnetic components will increase leading to the observed variations shown in Figures (FIGS. 15(a) and 15(b)). It is believed that $Sn_{1-x}Fe_xO_2$ will exhibit ferromagnetism for any value of x up to the solubility limit of Fe in $SnO_2$, or 10%.

b. $Sn_{1-x}Fe_xO$

Figures 31A, 31B:
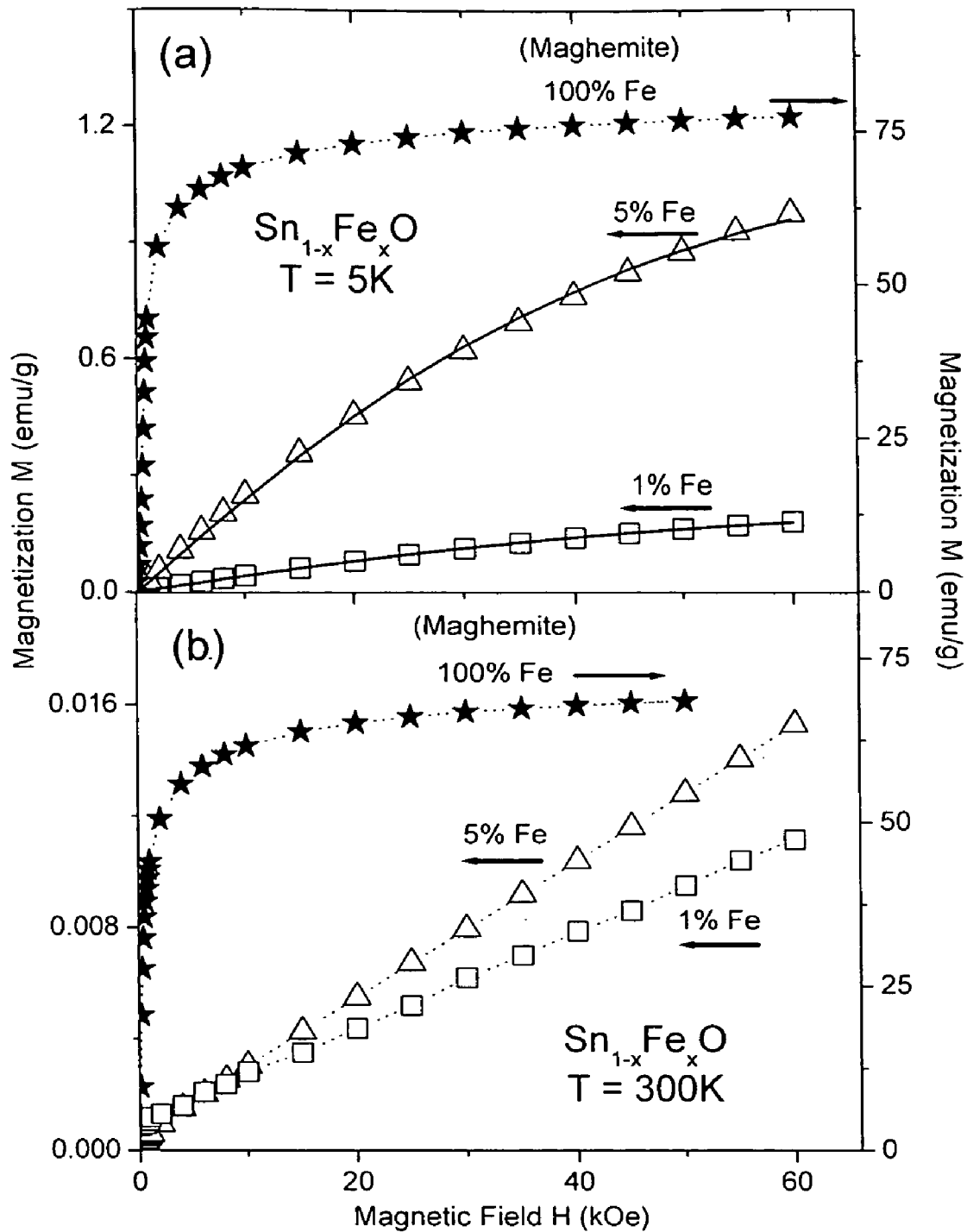
FIGS. 31 (a) and (b) show M vs H data for $Sn_{1-x}Fe_xO$ samples measured at 5 and 300K, respectively. Similar M vs H data collected from pure iron oxide (maghemite) prepared under identical conditions (but with no Sn precursors) are also shown. Solid lines through the data points are theoretical fits using the modified Brillouin-function-based form for a paramagnetic system.

FIG. 31 (a) shows the magnetization M of the $Sn_{1-x}Fe_xO$ samples measured at 5 K as a function of applied magnetic field H along with their theoretical estimates obtained using the modified Brillouin-function-based form for a paramagnetic system, given by $$M=M_0\{[(2J+1)/2J]\coth[(2J+1)y/(2J)]-(1/2J)\coth(y/2J)\}$$

where $y=g\mu_B JH/k(T+T_0)$, $M_0$ is the saturation magnetization, $g=2.0023$ is the spectroscopic splitting factor, $\mu_B$ is the Bohr magneton, and k is the Boltzman constant. Based on the Mossbauer data discussed above, this analysis was carried out assuming that $J=5/2$ (which is expected for $Fe^{3+}$). Here, $T_0$ is included as a measure of the magnetic interaction between the Fe spins, which prevents complete alignment of the spins even at the highest magnetic fields employed. A larger $T_0$ indicates stronger antiferromagnetic (AF) interactions between the disordered Fe spins. Magnitudes of $M_0$ and $T_0$ obtained from this analysis are shown in Table II. M versus H plots of $Sn_{1-x}Fe_xO$ samples measured at 300 K showed a linear variation owing to the paramagnetic behavior, as shown in FIG. 31 (b).

TABLE II

Variations of magnetization $M_0$, interaction temperature $T_0$, Curie constant C, and Curie-Weiss temperature θ of $Sn_{1-x}Fe_xO$ as a function of x.

| | $Sn_{1-x}Fe_xO$ | | | |
| --- | --- | --- | --- | --- |
| Fe percentage | Magnetization $M_0$ (emu/g) | Interaction temperature $T_0$ (K) | Curie constant ($10^{-4}$ emu K/g Oe) | Curie-Weiss Temperature θ (K) |
| 1 | 0.25 | 4.50 | 0.55 | 4.17 |
| 5 | 1.24 | 3.10 | 2.81 | 3.00 |

Magnetization M of the $Sn_{1-x}Fe_xO$ samples measured as a function of temperature T at a constant field H=500 Oe also showed the expected paramagnetic behavior, as shown in FIG. 26, following the modified Curie-Weiss law $\chi=\chi_0+C/(T+\theta)$, where $\chi_0=4(3)\times10^{-6}$ emu/g Oe represents weak non-paramagnetic contributions, Curie constant $C=N\mu^2/3k$ (N=number of magnetic ions/g, μ=magnetic moment of the ion), and θ is the Curie-Weiss temperature. These fits showed an increase in C (as well as $M_0$) with x, as shown in Table II, confirming the progressive doping of Fe ions. The positive values of θ indicate AF interactions between the Fe spins as observed in other systems as well. Both θ and $T_0$ decrease with x, as shown in Table II, indicating that the AF interaction decreases with increasing Fe doping. This may suggest that there are competing AF and ferromagnetic interactions as x increases.

The pure iron oxide sample prepared under identical conditions as $Sn_{1-x}Fe_xO$ was strongly ferromagnetic, as shown in FIGS. 31 (a) and 31 (b). M versus T data, shown in FIG. 21, of this sample indicated a blocking temperature $T_B$ ~21 K, suggesting the presence of nanoscale ferromagnetic particles. These observations match very well with the XRD data showing the formation of nanoscale maghemite. This also rules out the presence of this phase in the $Sn_{1-x}Fe_xO$ samples, which are all paramagnetic for $x \leq 0.05$.

2. Cobalt Concentration Dependence

Figures 32A, 32B, 32C:
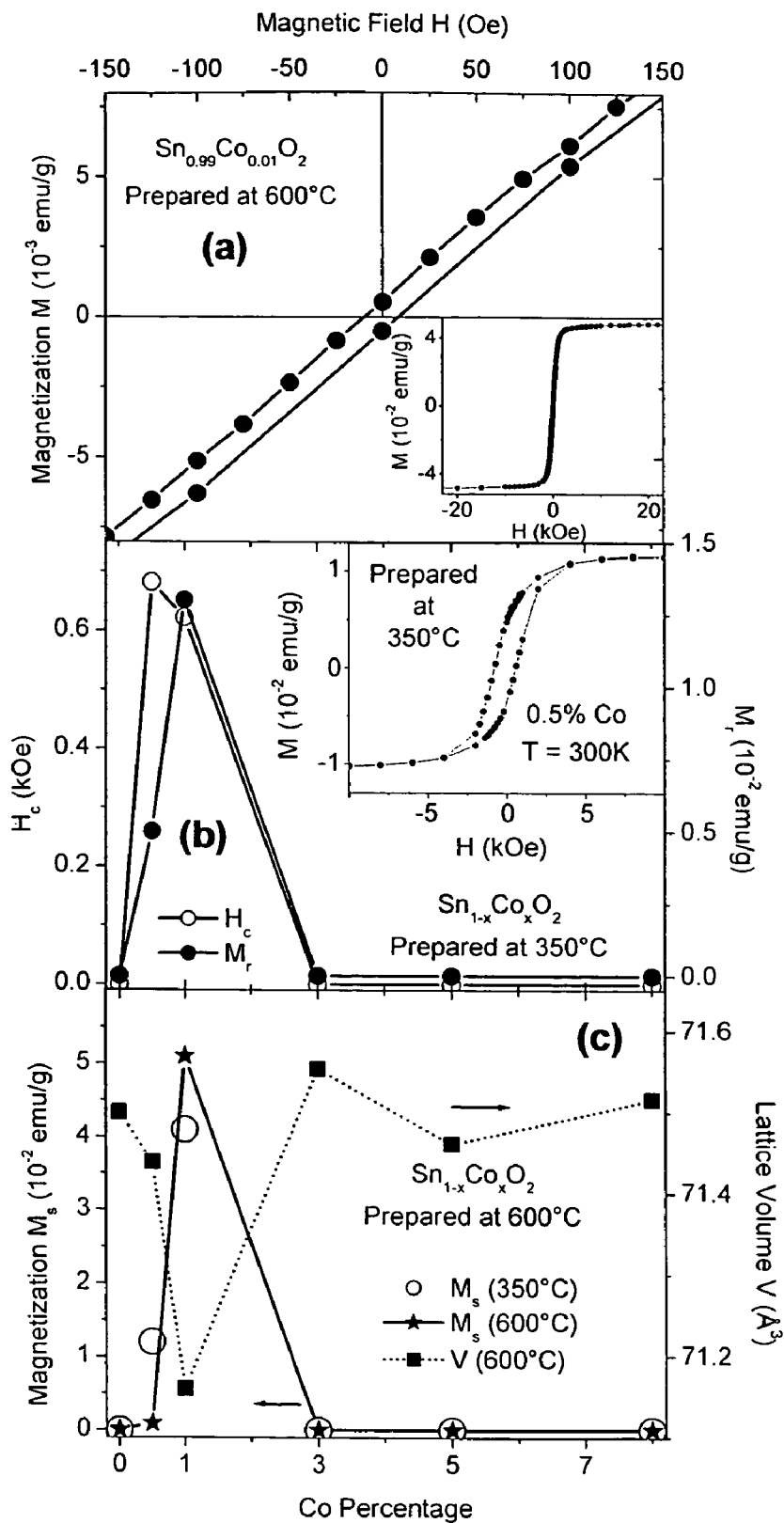
FIGS. 32 (a)-(c) show (a) the low field region of the room-temperature hysteresis loop of 600° C. prepared $Sn_{0.99}Co_{0.01}O_2$ sample showing a coercivity of 9 Oe; the inset in (a) shows the complete hysteresis loop of 600° C. prepared $Sn_{0.99}Co_{0.01}O_2$ showing saturation of the sample magnetization expected for a ferromagnetic system; (b) variation of the room-temperature coercivity $H_c$ and remanence $M_r$ of $Sn_{1-x}Co_xO_2$ prepared at 350° C. as a function x; inset in (b) shows the expanded view of the low-field region of the hysteresis loop of 350° C. prepared $Sn_{0.995}Co_{0.005}O_2$ sample; and, (c) variation of the saturation magnetization M, with x of $Sn_{1-x}Co_xO_2$ samples prepared at 350 (open circles) and 600° C. (solid stars), and the lattice volume V calculated using the a and c values of FIG. 9 (c) (shown with solid squares) as a function of Co-doping concentration for the 600° C. prepared $Sn_{1-x}Co_xO_2$.

Magnetic measurements carried out on pure $SnO_2$ nanoparticles showed the expected diamagnetism with a negative magnetic susceptibility. Applicant has shown that the $Sn_{1-x}Co_xO_2$ samples with $x \leq 0.01$ were all ferromagnetic at room-temperature when prepared in the 350 to 600° C. temperature range. FIG. 32(a) shows the room temperature hysteresis loop measured from a $Sn_{0.99}Co_{0.01}O_2$ sample prepared at 600° C. illustrating a clear ferromagnetic behavior with a coercivity $H_c=9$ Oe. In FIG. 32(b), the variations of the room-temperature coercivity $H_c$ and remanence $M_r$ of 350° C. prepared $Sn_{1-x}Co_xO_2$ as a function of Co concentration are shown. The observed coercivities of ~630 Oe and remanences as high as 31% are among the highest reported for dilute magnetic semiconductors. The observed variation of the saturation magnetization $M_s$ with Co concentration measured from the $Sn_{1-x}Co_xO_2$ samples prepared at 350 and 600° C. were comparable as illustrated in FIG. 6c. However, the coercivities of the $Sn_{0.99}Co_{0.01}O_2$ samples decreased from 630 Oe to 9 Oe as the preparation temperature increased from 350 to 600° C. (see FIGS. 32(a) and 32(b)). This most likely indicates a change in the magnetocrystalline anisotropy due to reasons that are unclear at present. More importantly, irrespective of the preparation temperature, all $Sn_{1-x}Co_xO_2$ samples prepared in the 350 to 600° C. showed complete destruction of the ferromagnetism above 1% Co doping and only a paramagnetic behavior was observed in this range, as shown in FIG. 32(b). This disappearance of ferromagnetism cannot be explained by assuming a 1% solubility limit for Co in $SnO_2$ because— (i) the ferromagnetic component due to the soluble part of the doped Co should not be destroyed or overwhelmed by the weak paramagnetic component of the segregated $Co_3O_4$ formed for x>0.01, (ii) the orthorhombic $SnO_2$ fraction in the samples, lattice parameters, band gap energy, particle size, and shape of the $Sn_{1-x}Co_xO_2$ particles (shown in FIGS. 9 and 10) continued to change with x for x>0.01, indicating >1% Co solubility in $SnO_2$, (iii) the observed disappearance of the Raman peaks (FIG. 11 (c)) for x>0.01 is unlikely to happen if additional Co doping is not taking place, and (iv) no evidence of any change in the oxidation state of Co or Sn is observed in the XPS measurements for $x \geq 0.01$.

The appearance of ferromagnetism in $Sn_{1-x}Co_xO_2$ samples with $x \leq 0.01$ and its complete absence at higher Co concentrations can be qualitatively understood by comparing the changes in the magnetic and structural properties noticed in the XRD, Raman, and TEM studies of the 600° C. prepared samples. As shown in the previous sections, for $x \leq 0.01$ the $SnO_2$ lattice contracts, resulting in the reduction of the distance between nearby $Co^{2+}$ spins, and possibly triggering a ferromagnetic coupling. Substitution of $Sn^{4+}$ ions (octahedrally coordinated with six nearest oxygen neighbors) in $SnO_2$ with $Co^{2+}$ ions will result in the creation of oxygen vacancies and additional charge carriers. It is not clear if this ferromagnetic ordering is carrier mediated or via other mechanisms such as based on localized defects (F-centers). Increasing the Co doping to $\geq 3\%$ results in a rapid expansion of the $SnO_2$ lattice and significant structural disorder indicated by the rapid broadening and disappearance of the Raman peaks, as shown in FIG. 11 (b). Such enormous structural changes might have destroyed the ferromagnetic ordering since the magnetic exchange interaction is extremely sensitive to the distance between the interacting spins.

It may be noted that the ferromagnetic regime of $Sn_{1-x}Co_xO_2$ with $x \leq 0.01$ corresponds to the compositions for which the $SnO_2$ lattice contracts (see FIGS. 32(b) and 32(c)). This might suggest that the observed ferromagnetism may be related to internal pressure changes. Changes in the internal or external lattice volume/pressure have been reported to produce ferromagnetism in itinerant electron metamagnets.

3. Temperature Dependence in $Sn_{1-x}Fe_xO_2$

Figure 33:
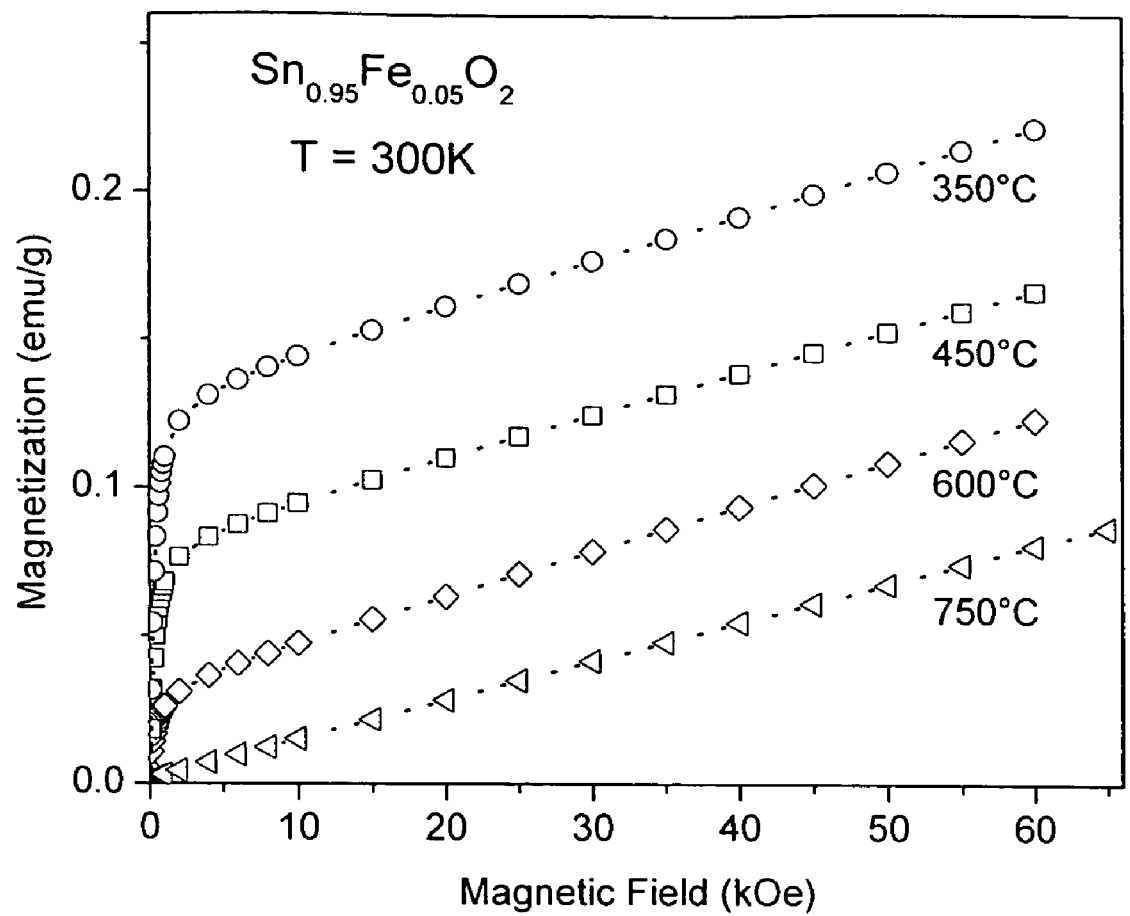
FIG. 33 shows M vs H data of $Sn_{0.95}Co_{0.05}O_2$, prepared at the different temperatures indicated, measured at 300K.

The ferromagnetic component of $Sn_{1-x}Fe_xO_2$ gradually declines and subsequently disappears as the preparation temperature increases, as shown in FIGS. 14, 22, and 33. Annealing the reaction precipitate at temperatures between 350 and 900° C. produces the $Sn_{1-x}Fe_xO_2$ phase. The M versus H data measured from the $Sn_{1-x}Fe_xO_2$ prepared by annealing the same reaction precipitate at different temperature, shown in FIG. 33, clearly shows the presence of a ferromagnetic component in samples annealed at 350, 450, and 600° C. Only a linear variation indicating a purely paramagnetic behavior was observed in the sample prepared by annealing at 750 and 900° C. The saturation magnetization $M_s$, estimated after subtracting the linear paramagnetic component $\chi_p$, is plotted in FIG. 22. This clearly establishes the fact that the ferromagnetic component is stronger when prepared at lower annealing temperatures and it gradually decreases with increasing preparation temperature, eventually disappearing completely for preparation temperatures >600° C., which is in excellent agreement with the Mossbauer data discussed above. The remanence $M_r$ obtained from the hysteresis loops, shown in FIG. 22, also decreases with preparation temperature. This figure also shows that for $Sn_{1-x}Fe_xO_2$ prepared at or below 600° C., the surface concentration of Fe is less than 4%.

Based on the observed changes in the Fe XPS peak intensity shown in FIG. 16 and the comparison of the concentrations estimated from the PIXE and XPS data listed in Table I, it was concluded that the Fe ions diffuse towards the particle surface as the preparation temperature increases. The lattice volume plotted in FIG. 8(b) shows a gradual contraction of the lattice as preparation temperature increases, presumably due to the outward diffusion and rearrangement of the doped Fe ions in the $SnO_2$ lattice as evidenced from the XPS data. However, above 600°, the lattice expands, approaching the undoped $SnO_2$ range, and this may be due to the expulsion of some of the doped Fe ions out of the $SnO_2$ lattice. This suggests that low preparation temperatures provide a relatively uniform distribution of the Fe dopant ions in the host $SnO_2$ lattice, and this favors ferromagnetism. The high surface diffusion of the dopant atoms in samples annealed above 600° C. causes the gradual disappearance of this ferromagnetic behavior.

4. Temperature Dependence in $Sn_{1-x}Co_xO_2$

To further investigate the role of synthesis parameters on the ferromagnetic behavior of 1% Co doped $SnO_2$, new samples were prepared by annealing the precipitate at temperatures of 250, 350, 450, 600 and 830° C. in air, taking a fresh portion of the dried precipitate each time. The sample annealed at 830° C. showed only the cassiterite phase of $SnO_2$, but those annealed at 600, 450, and 350° C. showed cassiterite and orthorhombic phases, as shown in FIG. 5(f). However, the sample annealed at 250° C. showed very strong peaks due to SnO and much weaker peaks of cassiterite $SnO_2$. This indicates that lower annealing temperatures present a much weaker oxidizing environment, leading to the formation of SnO and presumably oxygen deficient $SnO_2$. Some support for this possibility was obtained from the XRD pattern of a fresh dried precipitate annealed in flowing $H_2$ at 350° C., FIG. 5(f), which looks very similar to the sample prepared in air at 250° C. Based on this result, it is inferred that the lower annealing temperatures reduce the oxygen stoichiometry of $SnO_2$ and eventually converts to SnO at annealing temperatures <350° C.

Figure 30:
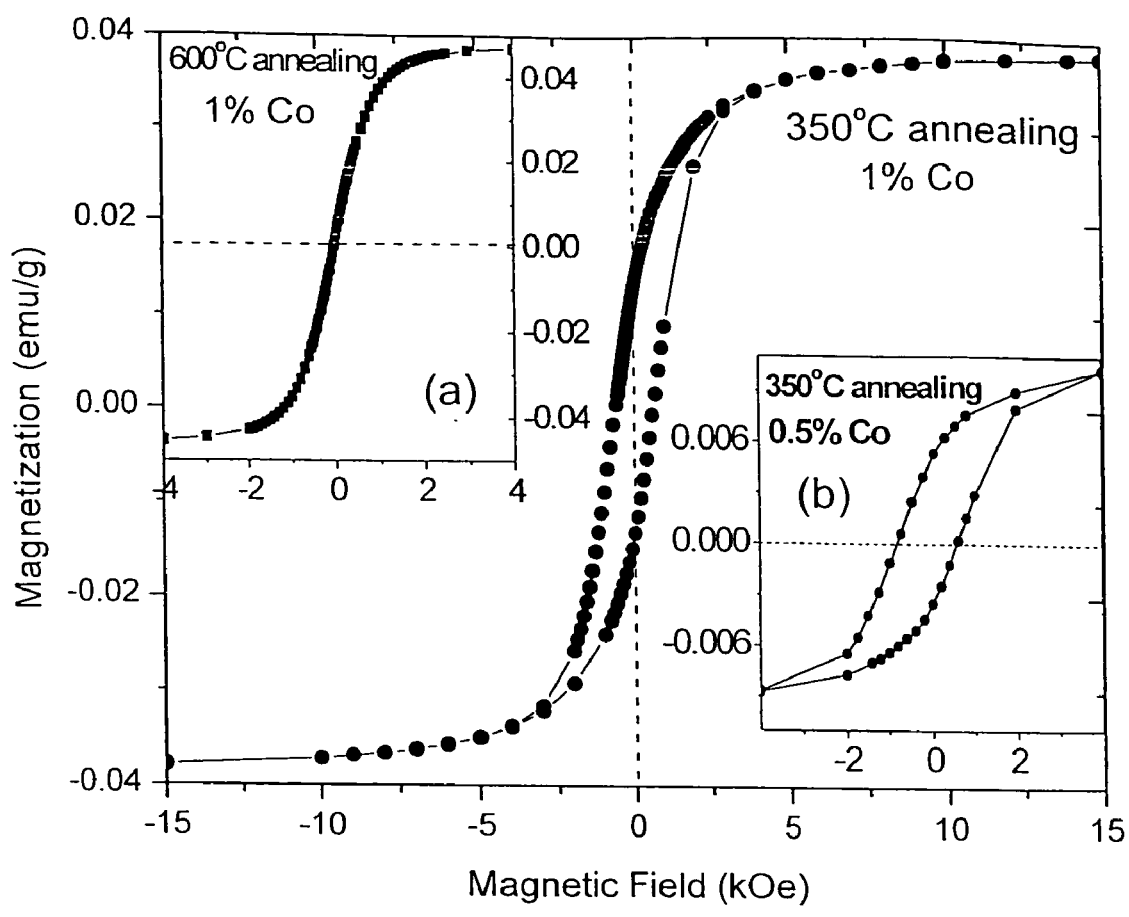
FIG. 30 shows a room temperature hysteresis loop obtained from $Sn_{0.99}Co_{0.01}O_2$ prepared at 350° C. The insets (a) and (b) show the hysteresis loops of $Sn_{0.99}Co_{0.01}O_2$ prepared at 600° C. and $Sn_{0.995}Co_{0.005}O_2$ prepared at 350° C. The lines joining the points are for visual aid.

In the main panel of FIG. 30, the hysteresis loop measured from the 1% Co doped $SnO_2$ prepared by annealing the dried precipitate at 350° C. is shown. The saturation magnetization is close to that observed for the 600° C. annealed samples, but the loop now exhibits a very large coercivity of ~630 Oe with good remanence and squareness. These observations were verified on several batches of samples prepared under identical conditions. Such large coercivities and squareness of the loop are seldom observed in DMS's at room temperature. Similar reproducible hysteresis loops were also observed in samples annealed at 450° C. However, no substantial ferromagnetic behavior was detected in samples annealed in air at 250° C. or in $H_2$ at 350° C. presumably due to extensive oxygen loss and transformation to the SnO phase. TEM data obtained from the $Sn_{0.99}Co_{0.01}O_2$ sample prepared at 350° C., FIG. 5(e), showed large micrometer sized particles compared to the ~37 nm sized particles, FIG. 5(c), observed in samples prepared at 600° C. Since the magnetizations of the samples prepared at these two temperatures are comparable, as shown in FIG. 30, the observed magnetic properties may not be due to nanoscale size effect. The fact that the samples prepared by annealing at 350 and 450° C. showed strong ferromagnetism with excellent reproducibility—as compared to the lower (~20%) reproducibility observed when annealed at 600° C. and its complete absence in samples annealed at 830° C.—may be closely linked to the differences in oxygen stoichiometry of these samples. Theoretically, carrier-mediated ferromagnetism in n-type oxide semiconductors is strongly related to the concentration of oxygen vacancies.

In conclusion, it has been shown that powder samples of chemically synthesized $Sn_{1-x}Co_xO_2$ powders with $x \leq 0.01$ exhibit RTFM. These samples exhibit significantly high coercivity (~630 Oe) and good squareness of the loop, but with low magnetic moment of 0.133 $\mu_B$/Co ion. Based on the XRD, PIXE, TEM and magnetic data, the observed ferromagnetic interactions seem to be controlled by the oxygen stoichiometry.

II. The Gas Sensing Process

Figure 34:
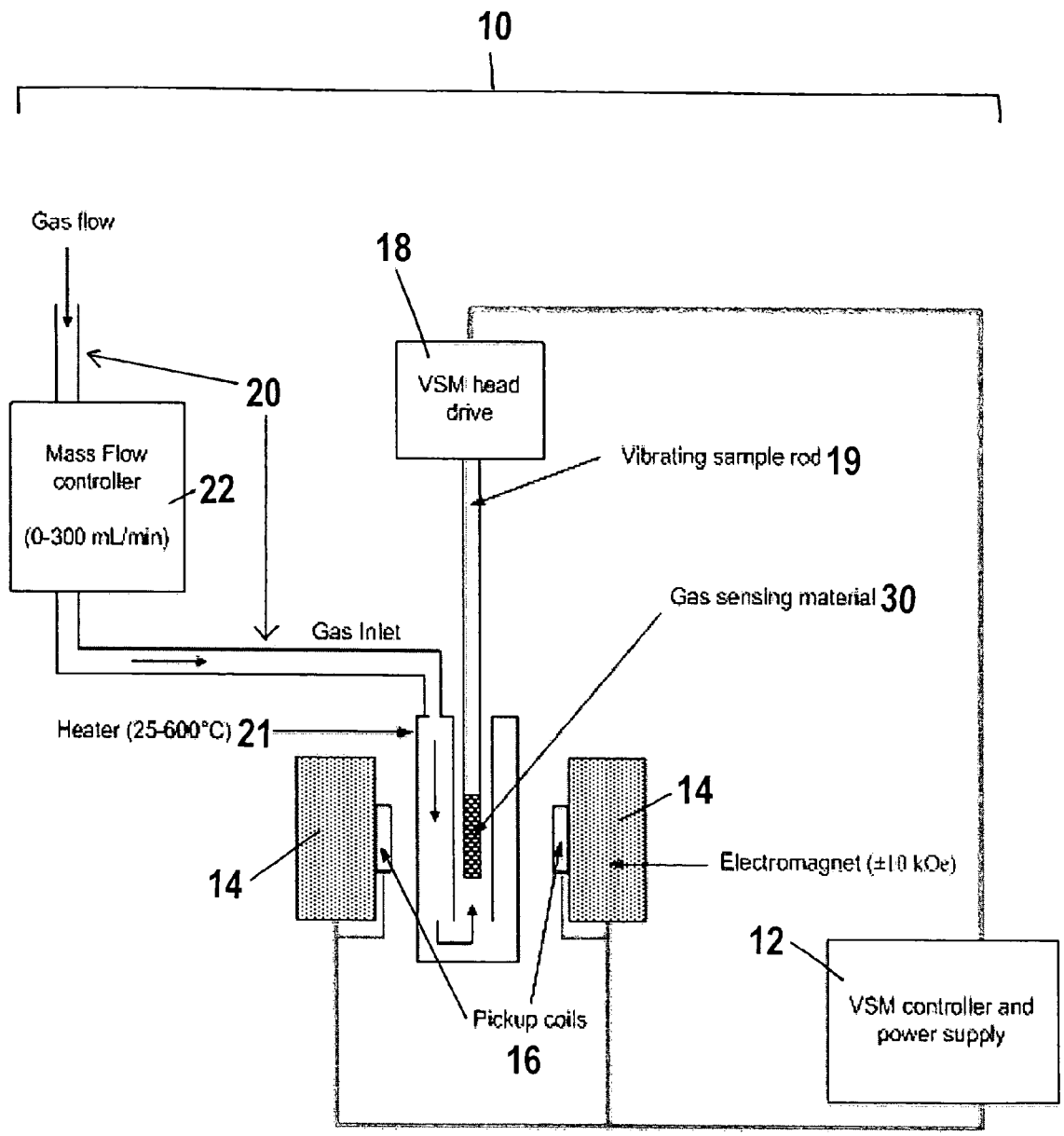
FIG. 34 shows an embodiment of a gas sensing apparatus using an embodiment of the invented process for detecting a gas.

The inventor has developed the ability to detect a gas by causing the gas to flow across a material and measuring the change in a magnetic property, preferably magnetization, of the material. Changes in the magnetic properties of a material by flowing a gas has never been used as a sensing method. The preferred material for the process is $Sn_{0.95}Fe_{0.05}O_2$, the manufacture and properties of which have been described above. However, other magnetic materials could be used, so long as their magnetic properties change as a gas flows across them. A gas detected using this process is molecular oxygen, $O_2$. However, any gas capable of oxidizing or reducing the magnetic material could be used. The preferred apparatus for detecting a gas using this method is shown in FIG. 34. The gas sensor 10 is made from taking an industry-standard vibrating sample magnetometer (VSM) and adding a gas inlet 20 and mass flow controller (0-300 mL/minute) 22. The VSM and gas sensor 10 comprise a VSM controller and power supply 12, a pair of electromagnets 14 of ∓10 kOe, a pair of pickup coils 16, and a VSM head drive 18. The gas-sensing material 30, preferably $Sn_{0.95}Fe_{0.05}O_2$, is placed at the end of the vibrating sample rod 19 connected to the VSM head drive. The gas flows out of the gas inlet 20 into a heater (25-600° C.) 21, then passes by the gas sensing material 30, and escapes into the atmosphere. The pickup coils 16 measure the magnetization of the gas sensing material 30; the magnetization changes as a function of the flow rate.

Figure 35:
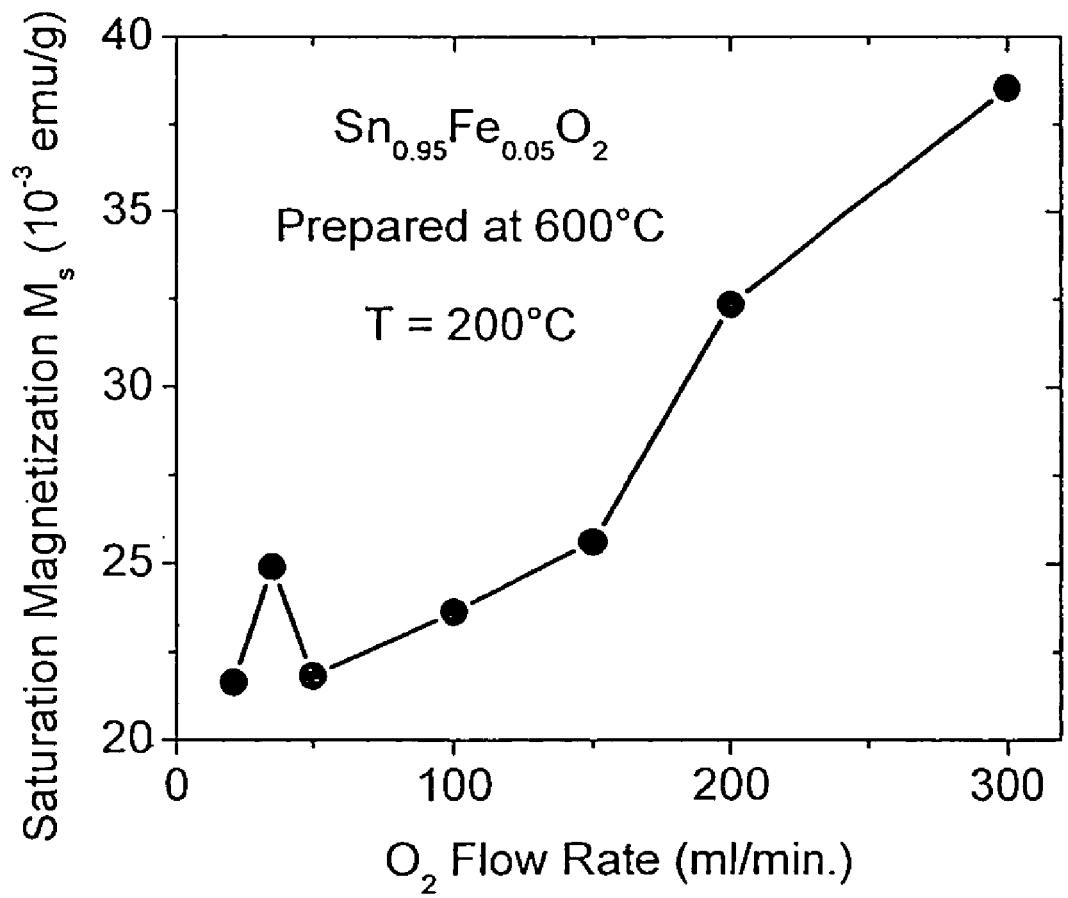
FIG. 35 shows changes in the saturation magnetization of $Sn_{0.95}Fe_{0.05}O_2$ versus flow rate of molecular oxygen at 200° C. for a sample prepared at 600° C.

To make the gas sensor 10 usable to detect unknown gases, it must first be calibrated with known gases. The saturation magnetization of $Sn_{0.95}Fe_{0.05}O_2$ is shown in FIG. 35 as a function of the flow rate of molecular oxygen. Then, an unknown quantity of gas can flow through the gas sensor 10, and the measured magnetization compared to a graph similar to that in FIG. 35 to determine the quantity and type of gas flowing through the sensor.

The magnetic properties of the gas sensing material 30 change because the carrier-mediated ferromagnetism of $Sn_{0.95}Fe_{0.05}O_2$ can be tailored by exposing it to reducing or oxidizing gaseous atmospheres. Thus, carrier-mediated ferromagnetism has been developed as a new, efficient gas sensing parameter.

Compared to their semiconductor gas sensor counterparts which measure changes in electrical properties, a magnetic gas sensor is much more attractive because no electrical contacts are required to detect the response, the detection process requires only a moderate magnetic field to magnetize the sample and a pickup coil to collect the magnetic response of the material, powder samples when used offer a very large surface area and higher sensitivity, magnetic responses are much faster than electrical responses, the lack of electrical contacts and the high magnetic response due to ferromagnetism will further add to the sensitivity of the gas-sensor device, and the operation range can be as high as the Curie temperature $T_c$.

Since the oxygen stoichiometry in $SnO_2$, the sensing material (before doping), is a surface driven property, the gas-sensing and magnetic properties of a doped oxide semiconductor, when used as the material, are expected to vary significantly with crystalline size, and therefore depend on the doping concentrations and preparation temperatures.

Although this invention has been described above with reference to particular means, materials and embodiments, it is to be understood that the invention is not limited to these disclosed particulars, but extends instead to all equivalents within the scope of the following claims.

What is claimed is:

1. A powder comprising cobalt-doped tin dioxide exhibiting room-temperature ferromagnetism, wherein the powder consists of nanoparticles.

2. The powder of claim 1 having no tin cobalt phases.

3. The powder of claim 1 having no $Co_3O_4$ phases.

4. The powder of claim 1 having no cobalt clusters.

5. The powder of claim 1 wherein the cobalt is incorporated into the tin dioxide lattice.

6. The powder of claim 1 wherein the cobalt is substitutionally incorporated into the tin dioxide lattice at the tin sites.

7. The powder of claim 1 comprising no significant amount of cobalt oxides.

8. The powder of claim 1 wherein the percentage of cobalt-doping is no greater than one percent.

9. The powder of claim 1 wherein the particles comprising the powder are nearly spherical in shape.

10. A powder comprising cobalt-doped tin dioxide exhibiting room-temperature ferromagnetism, wherein 95% of the particles comprising the powder are no more than fifty nanometers long.

11. The powder of claim 10 having no tin cobalt phases.

12. The powder of claim 10 having no $Co_3O_4$ phases.

13. The powder of claim 10 having no cobalt clusters.

14. The powder of claim 10 wherein the cobalt is incorporated into the tin dioxide lattice.

15. The powder of claim 10 wherein the cobalt is substitutionally incorporated into the tin dioxide lattice at the tin sites.

16. The powder of claim 10 comprising no significant amount of cobalt oxides.

17. The powder of claim 10 wherein the percentage of cobalt-doping is no greater than one percent.

18. A powder comprising cobalt-doped tin dioxide nanoparticles exhibiting room-temperature ferromagnetism.

19. The powder of claim 18 having no tin cobalt phases.

20. The powder of claim 18 having no $Co_3O_4$ phases.

21. The powder of claim 18 having no cobalt clusters.

22. The powder of claim 18 wherein the cobalt is incorporated into the tin dioxide lattice.

23. The powder of claim 18 wherein the cobalt is substitutionally incorporated into the tin dioxide lattice at the tin sites.

24. The powder of claim 18 comprising no significant amount of cobalt oxides.

25. The powder of claim 18 wherein the percentage of cobalt-doping is no greater than one percent.

26. The powder of claim 18 wherein 95% of the nanoparticles are no more than fifty nanometers long.

27. The powder of claim 18 wherein the particles comprising the powder are nearly spherical in shape.

28. Cobalt-doped tin dioxide nanoparticles exhibiting room-temperature ferromagnetism.

29. The nanoparticles of claim 28, wherein the cobalt is incorporated into the tin dioxide lattice.

30. The nanoparticles of claim 28, wherein the cobalt is substitutionally incorporated into the tin dioxide lattice at the tin sites.

31. The nanoparticles of claim 28, wherein the percentage of cobalt-doping is no greater than one percent.

32. The nanoparticles of claim 28, wherein 95% of the nanoparticles are no more than fifty nanometers long.

33. The nanoparticles of claim 28, wherein the particles comprising the powder are nearly spherical in shape.

* * * * *

UNITED STATES PATENT AND TRADEMARK OFFICE
CERTIFICATE OF CORRECTION

PATENT NO. : 7,582,222 B2  Page 1 of 1
APPLICATION NO. : 11/195573
DATED : September 1, 2009
INVENTOR(S) : Alex Punnoose It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1061 days.

Signed and Sealed this

Fourteenth Day of September, 2010

David J. Kappos
*Director of the United States Patent and Trademark Office*